(12) United States Patent
Okada et al.

(10) Patent No.: US 9,777,138 B2
(45) Date of Patent: Oct. 3, 2017

(54) LATENT ADDITIVE AND COMPOSITION CONTAINING LATENT ADDITIVE

(71) Applicant: ADEKA CORPORATION, Tokyo (JP)

(72) Inventors: Mitsuhiro Okada, Tokyo (JP); Tomoyuki Ariyoshi, Tokyo (JP)

(73) Assignee: ADEKA CORPORATION, Tokyo (JP)

( * ) Notice: Subject to any disclaimer, the term of this patent is extended or adjusted under 35 U.S.C. 154(b) by 0 days.

(21) Appl. No.: 14/405,159

(22) PCT Filed: Jun. 21, 2013

(86) PCT No.: PCT/JP2013/067091
§ 371 (c)(1),
(2) Date: Dec. 3, 2014

(87) PCT Pub. No.: WO2014/021023
PCT Pub. Date: Feb. 6, 2014

(65) Prior Publication Data
US 2015/0291772 A1 Oct. 15, 2015

(30) Foreign Application Priority Data

Jul. 31, 2012 (JP) ................. 2012-170676

(51) Int. Cl.
| | | |
|---|---|---|
| *C07C 69/96* | (2006.01) | |
| *C09K 15/04* | (2006.01) | |
| *C08K 5/134* | (2006.01) | |
| *C08K 5/3492* | (2006.01) | |
| *C07C 243/32* | (2006.01) | |
| *C09B 11/24* | (2006.01) | |
| *C09B 23/06* | (2006.01) | |
| *C09B 23/08* | (2006.01) | |
| *C09B 29/08* | (2006.01) | |
| *C09B 29/50* | (2006.01) | |
| *C09K 15/20* | (2006.01) | |
| *C07D 249/20* | (2006.01) | |
| *C07D 251/24* | (2006.01) | |
| *C07D 251/32* | (2006.01) | |
| *C07D 493/10* | (2006.01) | |
| *C08K 5/04* | (2006.01) | |
| *C08K 5/11* | (2006.01) | |
| *C08K 5/1545* | (2006.01) | |
| *C08K 5/1575* | (2006.01) | |

(Continued)

(52) U.S. Cl.
CPC .......... *C08K 5/34924* (2013.01); *C07C 69/96* (2013.01); *C07C 243/32* (2013.01); *C07D 249/20* (2013.01); *C07D 251/24* (2013.01); *C07D 251/32* (2013.01); *C07D 493/10* (2013.01); *C08K 5/04* (2013.01); *C08K 5/109* (2013.01); *C08K 5/11* (2013.01); *C08K 5/1545* (2013.01); *C08K 5/1575* (2013.01); *C08K 5/175* (2013.01); *C08K 5/18* (2013.01); *C08K 5/20* (2013.01); *C08K 5/315* (2013.01); *C08K 5/3417* (2013.01); *C08K 5/3435* (2013.01); *C08K 5/3462* (2013.01); *C08K 5/3475* (2013.01); *C08K 5/3492* (2013.01); *C08K 5/34922* (2013.01); *C08K 5/41* (2013.01); *C08K 5/521* (2013.01); *C08K 5/5333* (2013.01); *C09B 11/02* (2013.01); *C09B 11/04* (2013.01); *C09B 11/24* (2013.01); *C09B 23/06* (2013.01); *C09B 23/083* (2013.01); *C09B 23/105* (2013.01); *C09B 29/081* (2013.01); *C09B 29/0808* (2013.01); *C09B 29/366* (2013.01); *C09K 15/06* (2013.01); *C09K 15/20* (2013.01); *C07C 2601/14* (2017.05)

(58) Field of Classification Search
CPC .......... C07C 69/96; C09K 15/20; G03F 7/004
USPC .................. 568/579; 524/111, 375
See application file for complete search history.

(56) References Cited

U.S. PATENT DOCUMENTS 4,775,707 A * 10/1988 Slongo ................. C07D 249/20
524/91
5,194,653 A * 3/1993 Yamada .................. C07C 69/96
558/268

(Continued)

FOREIGN PATENT DOCUMENTS

JP 06-43630 2/1994
JP 06-51519 2/1994

(Continued)

OTHER PUBLICATIONS

JP 7-271037, Oct. 20, 1995; English Machine Translation.*

(Continued)

*Primary Examiner* — Venkataraman Balasubramanian
(74) *Attorney, Agent, or Firm* — Young & Thompson

(57) ABSTRACT

A latent additive which is represented by general formula (1). (In the formula, A represents a five-membered or six-membered aromatic ring or heterocyclic ring; each of $R^1$ and $R^2$ independently represents a hydrogen atom, a halogen atom, a cyano group, a hydroxyl group, a nitro group, a carboxyl group, an optionally substituted alkyl group having 1-40 carbon atoms, an aryl group having 6-20 carbon atoms, an arylalkyl group having 7-20 carbon atoms or a heterocyclic ring-containing group having 2-20 carbon atoms; and $R^4$ represents an alkyl group having 1-20 carbon atoms, an alkenyl group having 2-20 carbon atoms, an aryl group having 6-20 carbon atoms, an arylalkyl group having 7-20 carbon atoms, a heterocyclic ring-containing group having 2-20 carbon atoms or a trialkylsilyl group.)

7 Claims, No Drawings

(51) Int. Cl.

| | |
|---|---|
| *C08K 5/20* | (2006.01) |
| *C08K 5/3417* | (2006.01) |
| *C08K 5/3475* | (2006.01) |
| *C08K 5/41* | (2006.01) |
| *C08K 5/109* | (2006.01) |
| *C08K 5/17* | (2006.01) |
| *C08K 5/18* | (2006.01) |
| *C08K 5/315* | (2006.01) |
| *C08K 5/3435* | (2006.01) |
| *C08K 5/3462* | (2006.01) |
| *C08K 5/521* | (2006.01) |
| *C08K 5/5333* | (2006.01) |
| *C09K 15/06* | (2006.01) |
| *C09B 11/02* | (2006.01) |
| *C09B 11/04* | (2006.01) |
| *C09B 23/10* | (2006.01) |

(56) References Cited

U.S. PATENT DOCUMENTS

| | | | |
|---|---|---|---|
| 5,279,896 | A | 1/1994 | Tokunaga et al. |
| 5,597,854 | A | 1/1997 | Birbaum et al. |
| 5,683,856 | A | 11/1997 | Aoai et al. |
| 5,750,292 | A | 5/1998 | Sato et al. |
| 2008/0113294 | A1 | 5/2008 | Echigo et al. |
| 2015/0141459 | A1 | 5/2015 | Van Goor et al. |

FOREIGN PATENT DOCUMENTS

| | | |
|---|---|---|
| JP | 06-157421 | 6/1994 |
| JP | 06-179798 | 6/1994 |
| JP | 06-266107 | 9/1994 |
| JP | 06-266109 | 9/1994 |
| JP | 07-109380 | 4/1995 |
| JP | 07-271037 | 10/1995 |
| JP | 08-123030 | 5/1996 |
| JP | 11-71355 | 3/1999 |
| JP | 2002-097224 | 4/2002 |
| JP | 2004-157231 | 6/2004 |
| JP | 2006-058835 | 3/2006 |
| JP | 2011-173885 | 9/2011 |
| WO | WO 2011/133951 | 10/2011 |

OTHER PUBLICATIONS

JP 6-266109, Sep. 22, 1994; English Machine Translation.*
JP 6-266107, Sep. 22, 1994; English Machine Translation.*
JP 6-157421, Jun. 3, 1994; English Machine Translation.*
JP 6-43630, Feb. 18, 1994; English Machine Translation.*
Xu et al. CN 103044263, Apr. 17, 2013; CA 158:590120, 2013. CAPLUS Abstract provided.*
Hansen et al. Tetrahedron Letters (1998), 39(18), 2705-2706; CA 129:148793, 1998. CAPLUS Abstract provided.*
Nakamura et al. Peptide Science (2002), Volume Date 2001, 38th, 43-46; CA 138:517531, 2002. CAPLUS Abstract provided.*
Extended European Search Report—13 825 003.0—dated Jan. 12, 2016.
Olson D.R., Schroeter S.H.: "UV Screen Progenitors. Thermally Labile Urethane Derivatives of Hydroxyphenylbenzotriazoles and Hydroxybenzophenones", Journal of Applied Polymer Science, vol. 22, No. 8, Aug. 1, 1978 (Aug. 1, 1978), pp. 2165-2172.
Bolton D H et al: "Synthesis and Characterization of Hyperbranched Polycarbonates", Macromolecules, American Chemical Society, US, vol. 30, No. 7, Apr. 7, 1997(Apr. 7, 1997), pp. 1890-1896, XP000684813, ISSN: 0024-9297, DOI: 10.1021/MA961746D.
International Search Report PCT/JP2013/067091 dated Sep. 24, 2013.

* cited by examiner

LATENT ADDITIVE AND COMPOSITION CONTAINING LATENT ADDITIVE

TECHNICAL FIELD

This invention relates to a latent additive that is inactive at room temperature and activated on heating to a predetermined temperature to perform its function, and relates to a composition containing the latent additive. It also relates to an energy ray-polymerizable, colored photosensitive composition containing the composition and a color filter obtained using the colored photosensitive composition.

BACKGROUND ART

It is known to stabilize a resin composition by the addition of a UV absorber or an antioxidant thereby to improve the weatherability or heat resistance of the resin composition (Patent Literatures 1 to 4 below).

The problem generally associated with a phenol antioxidant, in particular, is that, because it has a trapping action on radicals that are largely influential on the deterioration of polymers, it acts as a polymerization inhibitor when added to a polymerization system to cause hindrance to cure (Patent Literature 5).

CITATION LIST

Patent Literature

Patent Literature 1: JP 6-179798A
Patent Literature 2: JP 7-109380A
Patent Literature 3: JP 11-071355A
Patent Literature 4: JP 2002-097224A
Patent Literature 5: U.S. Pat. No. 5,279,896A

SUMMARY OF INVENTION

Technical Problem

An object of the invention is to provide a latent additive that is inactive at room temperature and activated upon being heated to a predetermined temperature to perform its function. Another object of the invention is to provide a composition containing the latent additive. Still another object of the invention is to provide a colored photosensitive composition comprising the composition and a colorant, especially a colored photosensitive composition suited to make a color filter.

Solution to Problem

As a result of extensive investigations, the inventors have found that a compound having a specific protective group functions effectively as a latent additive and that a composition containing the compound suffers from no hindrance to curing and acquires excellent heat resistance. They have also found that a colored photosensitive composition obtained by adding a colorant to the above composition is suitable to make an optical filter, especially a color filter for image displays, such as liquid crystal display panels, without causing a reduction in luminance of the color filter. The present invention has been reached based on these findings.

The invention has been completed based on the above findings and provides a latent additive represented by general formula (1):

[Chem. 01]

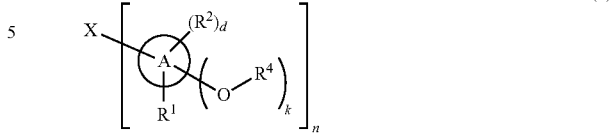

(1)

wherein A represents a 5- or 6-membered aromatic or heterocyclic ring;

$R^1$ and $R^2$ each independently represent a hydrogen atom, a halogen atom, a cyano group, a hydroxyl group, a nitro group, a carboxyl group, an optionally substituted C1-C40 alkyl group, a C6-C20 aryl group, a C7-C20 arylalkyl group, or a C2-C20 heterocyclic ring-containing group;

$R^4$ represents a C1-C20 alkyl group, a C2-C20 alkenyl group, a C6-C20 aryl group, a C7-C20 arylalkyl group, a C2-C20 heterocyclic ring-containing group, or a trialkylsilyl group;

the methylene moiety of the alkyl or arylalkyl group represented by $R^1$, $R^2$, and $R^4$ may be replaced by a combination of one or more groups selected from a carbon-carbon double bond, —O—, —S—, —CO—, —O—CO—, —CO—C—, —O—CO—O—, —O—CO—O—, —S—CO—, —CO—S—, —S—CO—O—, —CO—S—, —CO—NH—, —NH—CO—, —NH—CO—O—, —NR'—, >P=, —S—S—, and —SO$_2$—; R' represents a hydrogen atom or a C1-C8 alkyl group:

a plurality of $R^2$'s may be taken together to form a benzene ring or a naphthalene ring; a plurality of $R^2$'s may be the same or different; a plurality of $R^4$'s may be the same or different;

n represents an integer of 1 to 10; d represents an integer of 1 to 3:

k represents an integer of 1 to 3; and

X represents a single bond, a nitrogen atom, an oxygen atom, a sulfur atom, a phosphorus atom, a group represented by [Chem. 2] shown below, >P=O, >C=O, >NR$^{10}$, >PR$^{10}$, —OR$^{10}$, —SR$^{10}$, —NR$^{10}$R$^{11}$, —PR$^{10}$R$^{11}$, a C1-C120 aliphatic hydrocarbon group, a C6-C35 aromatic ring-containing hydrocarbon group, or a C2-C35 heterocyclic ring-containing group, the aliphatic hydrocarbon group, aromatic ring-containing hydrocarbon group, and heterocyclic ring-containing group having as many valences as n and optionally having a substituent; R$^{10}$ and R$^{11}$ each represent a hydrogen atom, an optionally substituted C1-C35 aliphatic hydrocarbon group, an optionally substituted C6-C35 aromatic ring-containing hydrocarbon group, or an optionally substituted C2-C35 heterocyclic ring-containing group, the aliphatic hydrocarbon group, aromatic ring-containing group, and heterocyclic ring-containing group being optionally substituted by a combination of one or more groups selected from a carbon-carbon double bond, —O—, —S—, —CO—, —O—CO—, —CO—O—, —O—CO—O—, —O—CO—O—, —S—CO—, —CO—S—, —S—CO—O—, —O—CO—S—, —CO—NH—, —NH—CO—, —NH—CO—O—, —NR'—, >P=O, —S—S—, —SO$_2$—, and a nitrogen atom; the aromatic or heterocyclic ring may be fused to one or more additional rings; when X is a nitrogen atom, a phosphorous atom, or the group represented by [Chem. 2] shown below, n is 3; when X is an oxygen atom or a sulfur atom, n is 2; when X is >C=O, —NH—CO—, —CO—NH—, >NR$^{10}$, or >PR$^{10}$, n is 2; and when X is —OR$^{10}$, —SR$^{10}$, —NR$^{10}$R$^{11}$, or —PR$^{10}$R$^{11}$, n is 1; and X may be taken together with A to form a ring.

[Chem. 2]

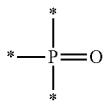

The invention provides a composition comprising the latent additive

The invention provides a colored photosensitive composition containing the composition, and a color filter obtained using the colored photosensitive composition.

The invention provides novel compounds represented by general formula (2), (6) and (8).

[Chem. 3]

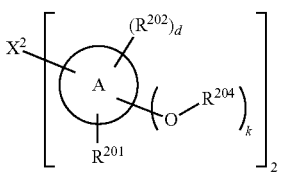

(2)

wherein A represents a 5- or 6-membered aromatic or heterocyclic ring;

$R^{201}$ and $R^{202}$ each independently represent a hydrogen atom, a halogen atom, a cyano group, a hydroxyl group, a nitro group, a carboxyl group, an optionally substituted C1-C40 alkyl group, a C6-C20 aryl group, a C7-C20 arylalkyl group, or a C2-C20 heterocyclic ring-containing group;

d represents an integer of 1 to 3;

k represents an integer of 1 to 3;

$R^{204}$ represents a C1-C20 alkyl group, a C2-C20 alkenyl group, a C6-C20 aryl group, a C7-C20 arylalkyl group, a C2-C20 heterocyclic ring-containing group, or a trialkylsilyl group;

the methylene moiety of the alkyl or arylalkyl group represented by $R^{201}$, $R^{202}$, and $R^{204}$ may be replaced by a combination of one or more groups selected from a carbon-carbon double bond, —O—, —S—, —CO—, —O—CO—, —CO—O—, —O—CO—O—, —O—CO—O—, —S—CO—, —CO—S—, —O—CO—S—, —S—CO—O—, —CO—NH—, —NH—CO—, —NH—CO—O—, —NR'—, >P=O, —S—S—, and —SO$_2$—; R' represents a hydrogen atom or a C1-C8 alkyl group;

a plurality of $R^{202}$'s may be taken together to form a benzene ring or a naphthalene ring:

a plurality of $R^{202}$'s may be the same or different; a plurality of $R^{204}$'s may be the same or different;

$X^2$ represents an oxygen atom, a sulfur atom, a group represented by [Chem. 4] shown below, >C=O, —NH—CO—, —CO—NH—, >NR$^{12}$, >PR$^{12}$, a substituent represented by group selected from general formula (3), general formula (4), or [Chem. 10] shown below; $R^{12}$ represents a hydrogen atom, an optionally substituted C1-C35 aliphatic hydrocarbon group, an optionally substituted C6-C35 aromatic ring-containing hydrocarbon group, or an optionally substituted C2-C35 heterocyclic ring-containing group, the aliphatic hydrocarbon group, aromatic ring-containing hydrocarbon group, and heterocyclic ring-containing group being optionally substituted by a combination of one or more groups selected from a carbon-carbon double bond, —O—, —S—, —CO—, —O—CO—, —CO—O—, —O—CO—O—, —O—CO—O—, —S—CO—, —CO—S—, —O—CO—S—, —S—CO—O—, —CO—NH—, —NH—CO—, —NH—CO—O—, —NR'—, >P=O, —S—S—, and —SO$_2$—; the aromatic or heterocyclic ring may be fused to one or more additional rings; and $X^2$ may be taken together with A to form a ring.

[Chem. 4]

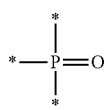

[Chem. 5]

(3)

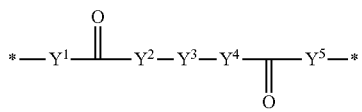

wherein $Y^1$ and $Y^5$ each independently represent a single bond, a C1-C4 alkylene group; $Y^2$ and $Y^4$ each independently represent an oxygen atom or —NR$^{13}$—; $R^{13}$ represents a hydrogen atom or a C1-C20 aliphatic hydrocarbon group; $Y^3$ represents a single bond, —NR$^{16}$—, a divalent C1-C35 aliphatic hydrocarbon group, a divalent C6-C35 aromatic ring-containing group, or a substituent represented by general formula (5) below, the aliphatic hydrocarbon group and C6-C35 aromatic ring-containing hydrocarbon group being optionally substituted by —COO—, —O—, —OCO—, —NHCO—, —NH—, or —CONH—; $R^{14}$ and $R^{15}$ each independently represent a hydrogen atom, a C1-C8 alkyl group, a C6-C20 aryl group, or a C7-C20 arylalkyl group; and $R^{16}$ represents a hydrogen atom, an optionally substituted C1-C35 aliphatic hydrocarbon group, an optionally substituted C6-C35 aromatic ring-containing hydrocarbon group, or an optionally substituted C2-C35 heterocyclic ring-containing group, the aliphatic hydrocarbon group, aromatic ring-containing hydrocarbon group, and heterocyclic ring-containing group being optionally substituted by a combination of one or more groups selected from a carbon-carbon double bond, —O—, —S—, —CO—, —O—CO—, —CO—O—, and —SO$_2$—.

[Chem. 6]

(4)

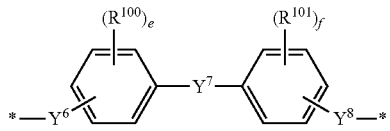

wherein $Y^6$ and $Y^8$ each independently represent —NR$^{17}$— or an optionally oxygen-interrupted C1-C4 alkylene group; $Y^7$ represents a single bond, —O—, —S—, —SO$_2$—, —CR$^{18}$R$^{19}$, or any one of the substituents represented by [Chem. 7] to [Chem. 9] shown below; $R^{17}$ represents a hydrogen atom or a C1-C20 aliphatic hydrocarbon group; $R^{18}$ and $R^{19}$ each independently represent a hydrogen atom or an optionally substituted C1-C8 alkyl group; $R^{100}$ and $R^{101}$ each independently represent a hydrogen atom, a halogen atom, a cyano group, a hydroxyl group, a nitro group, a carboxyl group, a C1-C8 alkyl group, or a C1-C8 alkoxy group; e represents a number of 1 to 4; and f represents a number of 1 to 4.

[Chem. 7]

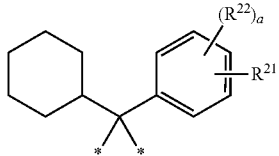

wherein $R^{21}$ represents a hydrogen atom, an optionally substituted phenyl group, or a C3-C10 cycloalkyl group; $R^{22}$ represents a C1-C10 alkyl group, a C1-C10 alkoxy group, a C2-C10 alkenyl group, or a halogen atom, the alkyl, alkoxy, or alkenyl group optionally having a substituent; and a represents an integer of 0 to 5.

[Chem.8]

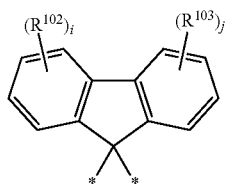

wherein $R^{102}$ and $R^{103}$ each independently represent a hydrogen atom, a halogen atom, a cyano group, a hydroxyl group, a nitro group, a carboxyl group, a C1-C8 alkyl group, or a C1-C8 alkoxy group; i represents a number of 1 to 4; and j represents a number of 1 to 4.

[Chem. 9]

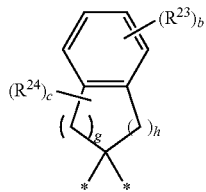

wherein $R^{23}$ and $R^{24}$ each independently represent an optionally substituted C1-C10 alkyl group, an optionally substituted C6-C20 aryl group, an optionally substituted C6-C20 aryloxy group, an optionally substituted C6-C20 arylthio group, an optionally substituted C6-C20 arylalkenyl group, an optionally substituted C7-C20 arylalkyl group, an optionally substituted C2-C20 heterocyclic ring-containing group, or a halogen atom, the methylene moiety of the alkyl and arylalkyl group being optionally replaced by an unsaturated bond, —O—, or —S—; adjacent $R^{23}$'s may be taken together to form a ring; b represents a number of 0 to 4; c represents a number of 0 to 8; and the sum of g and h is 2 to 4.

[Chem. 10]

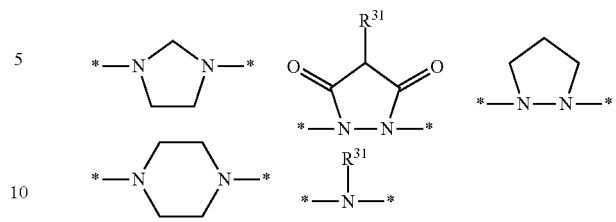

wherein $R^{31}$ represents a hydrogen atom, an optionally substituted C1-C35 aliphatic hydrocarbon group, an optionally substituted C6-C35 aromatic ring-containing hydrocarbon group, or an optionally substituted C2-C35 heterocyclic ring-containing group, the aliphatic hydrocarbon group being optionally substituted by a carbon-carbon double bond, —O—, —S—, —CO—, —O—CO—, —CO—O—, or —SO$_2$—.

[Chem. 11]

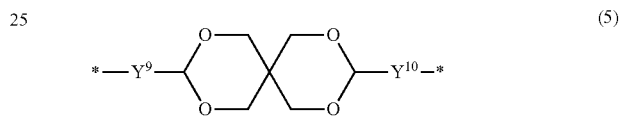

(5)

wherein $Y^9$ and $Y^{10}$ each independently represent a C1-C4 alkylene group.

[Chem. 12]

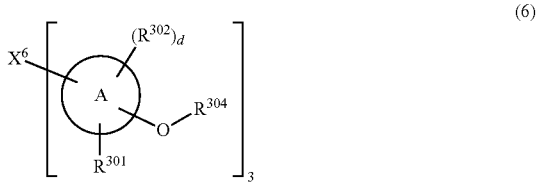

(6)

wherein A represents a 5- or 6-membered aromatic or heterocyclic ring;

$R^{301}$ and $R^{302}$ each independently represent a hydrogen atom, a halogen atom, a cyano group, a hydroxyl group, a nitro group, a carboxyl group, an optionally substituted C1-C40 alkyl group, a C6-C20 aryl group, a C7-C20 arylalkyl group, or a C2-C20 heterocyclic ring-containing group;

d represents an integer of 1 to 3;

k represents an integer of 1 to 3;

$R^{304}$ represents a C1-C20 alkyl group, a C2-C20 alkenyl group, a C6-C20 aryl group, a C7-C20 arylalkyl group, a C2-C20 heterocyclic ring-containing group, or a trialkylsilyl group;

the methylene moiety of the alkyl or arylalkyl group represented by $R^{301}$, $R^{302}$, and $R^{304}$ may be replaced by a combination of one or more groups selected from a carbon-carbon double bond. —O—, —S—, —CO—, —O—CO—, —CO—O—, —O—CO—O—, —O—CO—, —S—CO—, —CO—S—, —O—CO—S—, —S—CO—O—, —CO—NH—, —NH—CO—, —NH—CO—O—, —NR'—, >P=O, —S—S—, —SO$_2$—, and a nitrogen atom; R' represents a hydrogen atom or a C1-C8 alkyl group;

a plurality of $R^{302}$'s may be taken together to form a benzene ring or a naphthalene ring;

a plurality of $R^{302}$'s may be the same or different; a plurality of $R^{304}$'s may be the same or different; and $X^3$ represents a substituent represented by general formula (7);

$X^3$ may optionally be taken together with A to form a ring; and the aromatic or heterocyclic ring may be fused to one or more additional rings.

[Chem. 13]

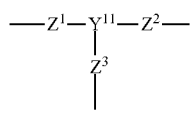

(7)

wherein $Y^{11}$ represents a trivalent C3-C35 aliphatic hydrocarbon group, a trivalent C3-C35 alicyclic hydrocarbon group, a trivalent C6-C35 aromatic ring-containing hydrocarbon group, or a trivalent C2-C35 heterocyclic ring-containing group; $Z^1$, $Z^2$, and $Z^3$ each independently represent a single bond, —O—, —S—, >CO, —CO—O—, —O—CO—, —SO$_2$—, —SS—, —SO—, >NR$^{32}$, >PR$^{32}$, an optionally substituted C1-C35 aliphatic hydrocarbon group, an optionally substituted C6-C35 aromatic ring-containing hydrocarbon group, or an optionally substituted C2-C35 heterocyclic ring-containing group; and $R^{32}$ represents a hydrogen atom, an optionally substituted C1-C35 aliphatic hydrocarbon group, an optionally substituted C6-C35 aromatic ring-containing hydrocarbon group, or an optionally substituted C2-C35 heterocyclic ring-containing group, the aliphatic hydrocarbon group being optionally substituted by a combination of one or more groups selected from a carbon-carbon double bond, —O—, —S—, —CO—, —O—CO—, —CO—O—, and —SO$_2$—.

[Chem. 14]

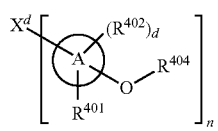

(8)

wherein A represents a 5- or 6-membered aromatic or heterocyclic ring;

$R^{401}$ and $R^{402}$ each independently represent a hydrogen atom, a halogen atom, a cyano group, a hydroxyl group, a nitro group, a carboxyl group, an optionally substituted C1-C40 alkyl group, a C6-C20 aryl group, a C7-C20 arylalkyl group, or a C2-C20 heterocyclic ring-containing group;

d represents an integer of 1 to 3;

k represents an integer of 1 to 3;

$R^{404}$ represents a C1-C20 alkyl group, a C2-C20 alkenyl group, a C6-C20 aryl group, a C7-C20 arylalkyl group, a C2-C20 heterocyclic ring-containing group, or a trialkylsilyl group;

the methylene moiety of the alkyl or arylalkyl group represented by $R^{401}$, $R^{402}$, and $R^{404}$ may be replaced by a combination of one or more groups selected from a carbon-carbon double bond, —O—, —S—, —CO—, —O—CO—, —CO—O—, —O—CO—O—, —O—CO—O—, —S—CO—, —CO—S—, —O—CO—S—, —S—CO—O—, —CO—NH—, —NH—CO—, —NH—CO—O—, —NR'—, >P=O, —S—S—, and —SO$_2$—; R' represents a hydrogen atom or a C1-C8 alkyl group;

a plurality of $R^{402}$'s may be taken together to form a benzene ring or a naphthalene ring;

a plurality of $R^{402}$'s may be the same or different; a plurality of $R^{404}$'s may be the same or different;

n represents a number of 4 to 6:

$X^4$ represents a substituent represented by general formula (9) when n is 4, $X^4$ represents a substituent represented by general formula (10) when n is 5, or $X^4$ represents a substituent represented by general formula (11) when n is 6:

$X^4$ may optionally be taken together with A to form a ring; and the aromatic or heterocyclic ring may be fused to one or more additional rings.

[Chem. 15]

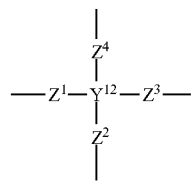

(9)

wherein $Y^{12}$ represents a carbon atom, a tetravalent C1-C35 aliphatic hydrocarbon group, a tetravalent C6-C35 aromatic ring-containing hydrocarbon group, or a tetravalent C2-C35 heterocyclic ring-containing group, the aliphatic hydrocarbon group being optionally substituted by a combination of one or more groups selected from —COO—, —O—, —OCO—, —NHCO—, —NH—, and —CONH—; and $Z^1$, $Z^2$, $Z^3$, and $Z^4$ each independently have the same meaning as $Z^1$ to $Z^3$ in general formula (7).

[Chem. 16]

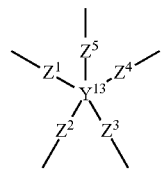

(10)

wherein $Y^{13}$ represent a pentavalent C2-C35 aliphatic hydrocarbon group, a pentavalent C6-C30 aromatic ring-containing hydrocarbon group, or a pentavalent C2-C30 heterocyclic ring-containing group, the aliphatic hydrocarbon group being optionally substituted by a combination of one or more groups selected from —COO—, —O—, —OCO—, —NHCO—, —NH—, and —CONH—; and $Z^1$, $Z^2$, $Z^3$, $Z^4$, and $Z^5$ each independently have the same meaning as $Z^1$ to $Z^3$ in general formula (7).

[Chem. 17]

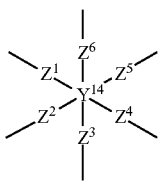

(11)

wherein $Y^{14}$ represents a hexavalent C2-C35 aliphatic hydrocarbon group, a hexavalent C6-C35 aromatic ring-containing hydrocarbon group, or a hexavalent C2-C35 heterocyclic ring-containing group, the aliphatic hydrocarbon group being optionally substituted by a combination of one or more groups selected from —COO—, —O—, —OCO—, —NHCO—, —NH—, and —CONH—; and $Z^1$, $Z^2$, $Z^3$, $Z^4$, $Z^5$, and $Z^6$ each independently have the same meaning as $Z^1$ to $Z^3$ in general formula (7).

Advantageous Effects of Invention

The invention provides a latent additive that is inactive at room temperature and activated on heating to a predetermined temperature. The latent additive provides a composition that exhibits excellent heat resistance without causing hindrance to curing.

DESCRIPTION OF EMBODIMENTS

The invention will be described in detail based on its preferred embodiments.

The latent additive represented by general formula (1) will be described first.

As used herein, the term "latent additive" refers to an additive that is inactive at room temperature or in a prebaking step at or below 150° C. and becomes active on release of its protective group by heating at 100 to 250° C. or at 80° to 200° C. in the presence of an acid/base catalyst. Examples of the latent additive include additives for resins, such as latent antioxidants and latent UV absorbers, latent color developers for heat-sensitive paper, latent storage stabilizers for heat-sensitive paper, and latent curing agents.

The latent additive represented by general formula (1) has a structure composed of a specific n-valent atom or group of atoms represented by X and n's specific groups bonded to X. The n's groups may be the same or different. n is 1 to 10 and preferably 2 to 6 in view of ease of synthesis.

Examples of the 5-membered aromatic ring represented by A in general formula (1) include cyclopentadiene and ferrocene. Examples of the 5-membered heterocyclic ring include furan, thiophene, pyrrole, pyrrolidine, pyrazolidine, pyrazole, imidazole, imidazolidine, oxazole, isoxazole, isoxazolidine, thiazole, isothiazole, and isothiazolidine. Examples of the 6-membered aromatic ring include benzene, naphthalene, anthracene, fluorene, perylene, and pyrene. Examples of the 6-membered heterocyclic ring include piperidine, piperazine, morpholine, thiomorpholine, pyridine, pyrazine, pyrinmidine, pyridazine, and triazine. These rings may optionally be fused to one or more additional rings or substituted. Examples of such fused rings include quinoline, isoquinoline, indole, julolidine, benzoxazole, benztriazole, and azulene.

Examples of the halogen atom represented by $R^1$ or $R^2$ include fluorine, chlorine, bromine, and iodine.

Examples of the C1-C40 alkyl group represented by $R^1$, $R^2$, and $R^4$ include methyl, ethyl, propyl, isopropyl, butyl, sec-butyl, tert-butyl, isobutyl, amyl, isoamyl, tert-amyl, cyclopentyl, hexyl, 2-hexyl, 3-hexyl, cyclohexyl, 4-methylcyclohexyl, heptyl 2-heptyl, 3-heptyl, isoheptyl, tert-heptyl, 1-octyl, isooctyl, tert-octyl, and adamantyl.

Examples of the C1-C8 alkoxy group represented by $R^1$ and $R^2$ include methoxy, ethoxy, isopropoxy, butoxy, sec-butoxy, tert-butoxy, isobutoxy, amyloxy, isoamyloxy, tert-amyloxy, hexyloxy, 2-hexyloxy, 3-hexyloxy, cyclohexyloxy, 4-methylcylcohexyloxy, heptyloxy, 2-heptyloxy, 3-heptyloxy, isoheptyloxy, tert-heptyloxy, 1-octyloxy, isooctyloxy, and tert-octyloxy.

Examples of the substituent that may substitute the C1-C8 alkyl and alkoxy groups represented by $R^1$ and $R^2$ include ethylenically unsaturated groups, e.g., vinyl, allyl, acryl, and methacryl; halogen atoms, e.g., fluorine, chlorine, bromine, and iodine; acyl groups, e.g., acetyl, 2-chloroacetyl, propionyl, octanoyl, acryloyl, methacryloyl, phenylcarbonyl (benzoyl), phthaloyl, 4-trifluoromethylbenzoyl, pivaloyl, salicyloyl, oxaloyl, stearoyl, methoxycarbonyl, ethoxycarbonyl, t-butoxycarbonyl, n-octadecyloxycarbonyl, and carbamoyl; acyloxy groups, e.g., acetyloxy and benzoyloxy; (un)substituted amino groups, e.g., amino, ethylamino, dimethylamino, diethylamino, butylamino, cyclopentylamino, 2-ethylhexylamino, dodecylamino, anilino, chlorophenylamino, toluidino, anisidino, N-methylanilino, diphenylamino, naphthylamino, 2-pyridylamino, methoxycarbonylamino, phenoxycarbonylamnino, acetylamino, benzoylamino, formylamino, pivaloylaminno, lauroylamino, carbamoylamino, N,N-dimethylaminocarbonylamino, N,N-diethylaminocarbonylamino, morpholinocarbonylamino, methoxycarbonylamino, ethoxycarbonylamino, t-butoxycarbonylamino, n-octadecyloxycarbonylanino, N-methyl-methoxycarbonylamino, phenoxycarbonylamino, sulfanmoylamino, N,N-dimethylaminosulfonylamino, methylsulfonylamino, butylsulfonylamino, and phenylsulfonylamino; sulfonamido, sulfonyl, carboxyl, cyano, sulfo, hydroxyl, nitro, mercapto, imido, carbamoyl, sulfonamido, phosphono, phosphoric acid group; or a salt of carboxyl, sulfo, phosphono, or phosphoric acid group.

Examples of the C6-C20 aryl group represented by $R^4$ include phenyl, naphthyl, and anthracenyl.

Examples of the C7-C20 arylalkyl group represented by $R^4$ include benzyl, fluorenyl, indenyl, and 9-fluorenylmethyl.

Examples of the C2-C20 heterocyclic ring-containing group represented by $R^4$ include pyridyl, pyrimidyl, pyridazyl, piperidyl, pyranyl, pyrazolyl, triazinyl, pyrrolyl, quinolyl, isoquinolyl, imidazolyl, benzimidazolyl, triazolyl, furyl, furanyl, benzofuranyl, thienyl, thiophenyl, benzothiophenyl, thiadiazolyl, thiazolyl, benzothiazolyl, oxazolyl, benzoxazolyl, isothiazolyl, isoxazolyl, indolyl, 2-pyrrolidinon-1-yl, 2-piperidon-1-yl, 2,4-dioxyimidazolidin-3-yl, and 2,4-dioxyoxazolidin-3-yl.

Examples of the trialkylsilyl group represented by $R^4$ include trimethylsilane, triethylsilane, and ethyldimethylsilane.

A compound of general formula (1) in which $R^4$ is a C1-C8 alkyl group having —CO—O— bonded to its terminal on the oxygen atom side is preferred for efficient development of its function as a latent additive.

Examples of the optionally substituted C1-C35 monovalent aliphatic hydrocarbon group represented by X, $R^{10}$, and $R^{11}$ include alkyl groups, such as methyl, ethyl, propyl, isopropyl, cyclopropyl, butyl, sec-butyl, tert-butyl, isobutyl, amyl, isoamyl, tert-amyl, cyclopentyl, hexyl, 2-hexyl, 3-hexyl, cyclohexyl, bicyclohexyl, 1-methylcyclohexyl, heptyl, 2-heptyl, 3-heptyl, isoheptyl, tert-heptyl, n-octyl, isooctyl, tert-octyl 2-ethylhexyl, nonyl, isononyl, and decyl; alkoxy groups, such as methoxy, ethoxy, propoxy, isopropoxy, butoxy, sec-butoxy, tert-butoxy, isobutoxy, amyloxy, isoamyloxy, tert-amyloxy, hexyloxy, cyclohexyloxy, heptyloxy, isoheptyloxy, tert-heptyloxy, n-octyloxy, isooctyloxy, tert-octyloxy, 2-ethylhexyloxy, nonyloxy, and decyloxy; alkylthio groups, such as methylthio, ethylthio, propylthio, isopropylthio, butylthio, sec-butylthio, tert-butylthio, isobutylthio, amylthio, isoamylthio, tert-amylthio, hexylthio, cyclohexylthio, heptylthio, isoheptylthio, tert-heptylthio, n-octylthio, isooctylthio, tert-octylthio, and 2-ethylhexylthio; and alkenyl groups, such as vinyl 1-methylethenyl, 2-methylethenyl, 2-propenyl, 1-methyl-3-propenyl, 3-butenyl, 1-methyl-3-butenyl, isobutenyl, 3-pentenyl, 4-hexenyl, cyclohexenyl, bicyclohexenyl, heptenyl, octenyl, decenyl, pentadecenyl, eicosenyl, and tricosenyl.

Examples of the optionally substituted C6-C35 monovalent aromatic ring-containing hydrocarbon group include arylalkyl groups, such as benzyl, phenethyl, diphenylmethyl, triphenylmethyl, styryl, and cinnamyl; aryl groups, such as phenyl and naphthyl; aryloxy groups, such as phenoxy and naphthyloxy; and arylthio groups, such as phenylthio and naphthylthio.

Examples of the optionally substituted C2-C35 monovalent heterocyclic ring-containing group include pyridyl, pyrimidyl, pyridazyl, piperidyl, pyranyl, pyrazolyl, triazinyl, pyrrolyl, quinolyl, isoquinolyl, imidazolyl, benzimidazolyl, triazolyl, furyl, furanyl, benzofuranyl, thienyl, thiophenyl benzothiophenyl, thiadiazolyl, thiazolyl, benzothiazolyl, oxazolyl, benzoxazolyl, isothiazolyl, isoxazolyl, indolyl, 2-pyrryolidinon-1-yl, 2-piperidon-1-yl, 2,4-dioxyimidazolildin-3-yl, 2,4-dioxyoxazolidin-3-yl, and benzotriazoyl.

Examples of the substituent include ethylenically unsaturated groups, e.g., vinyl allyl, acryl and methacryl; halogen atoms, e.g., fluorine, chlorine, bromine, and iodine; acyl groups, e.g., acetyl, 2-chloroacetyl, propionyl, octanoyl, acryloyl, methacryloyl, phenylcarbonyl (benzoyl), phthaloyl, 4-trifluoromethylbenzoyl, pivaloyl, salicyloyl, oxaloyl, stearoyl, methoxycarbonyl, ethoxycarbonyl, t-butoxycarbonyl, n-octadecyloxycarbonyl, and carbamoyl; acyloxy groups, e.g., acetyloxy and benzoyloxy; (un)substituted amino groups, e.g., amino, ethylamino, dimethylamino, diethylamino, butylamino, cyclopentylamino, 2-ethylhexylamino, dodecylamino, anilino, chlorophenylamino, toluidino, anisidino, N-methylanilino, diphenylamino, naphthylamino, 2-pyridylamino, methoxycarbonylamino, phenoxycarbonylamino, acetylamino, benzoylamino, formylamino, pivaloylamino, lauroylamino, carbamoylamino. N,N-dimethylaminocabonylamino, N,N-diethylaminocarbonylamino, morpholinocarbonylamino, methoxycarbonylamino, ethoxycarbonylamino, t-butoxycarbonylamino, n-octadecyloxycarbonylamino, N-methyl-methoxycarbonylamino, phenoxycarbonylamino, sulfamoylamino, N,N-dimethylaminosulfonylamino, methylsulfonylamino, butylsulfonylamino, and phenylsulfonylamino; sulfonamido, sulfonyl, carboxyl, cyano, sulfo, hydroxyl, nitro, mercapto, imido, carbamoyl sulfonamido, phosphono, phosphoric acid group; or a salt of carboxyl, sulfo, phosphono, or phosphoric acid group.

When n is 2, X is exemplified by a group represented by general formula (12) below. When n is 3, X is exemplified by a group represented by general formula (7). When n is 4, X is exemplified by a group represented by general formula (9). When n is 5, X is exemplified by a group represented by general formula (10). When n is 6, X is exemplified by a group represented by general formula (11).

[Chem. 18]

$$*-13\ Z^1-X^1-Z^2-* \qquad (12)$$

wherein $X^1$ represents $-CR^{32}R^{33}-$, $-NR^{34}-$, a C1-C35 divalent aliphatic hydrocarbon group, a divalent C6-C35 aromatic ring-containing hydrocarbon group, a C2-C35 divalent heterocyclic ring-containing group, or a substituent represented by any one of [Chem. 19] to [Chem. 21] shown below, the aliphatic hydrocarbon group, C6-C35 aromatic ring-containing hydrocarbon group, or C2-C35 heterocyclic ring-containing group being optionally substituted by a linking group selected from $-O-$, $-S-$, $-CO-$, $-COO-$, $-OCO-$, $-NH-$, and a combination thereof; $R^{32}$ and $R^{33}$ each represent a hydrogen atom, a C1-C8 alkyl group, a C6-C20 aryl group, or a C7-C20 arylalkyl group; $Z^1$ and $Z^2$ each independently represent a single bond. $-O-$, $-S-$, $>CO$, $-CO-O-$, $-O-CO-$, $-SO_2-$, $-SS-$, $-SO-$, $>NR^{35}$ or $>PR^{35}$; $R^{34}$ and $R^{35}$ each represent a hydrogen atom, an optionally substituted C1-C35 aliphatic hydrocarbon group, an optionally substituted C6-C35 aromatic ring-containing hydrocarbon group, or an optionally substituted C2-C35 heterocyclic ring-containing group.

[Chem. 19]

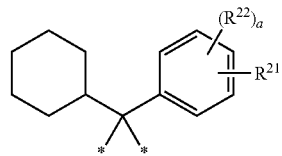

wherein $R^{21}$ represents a hydrogen atom, an optionally substituted phenyl group or an optionally substituted C3-C10 cycloalkyl group; $R^{22}$ represents a C1-C10 alkyl group, a C1-C10 alkoxy group, a C2-C10 alkenyl group, or a halogen atom, the alkyl, alkoxy, or alkenyl group optionally having a substituent; and a represents an integer of 0 to 5.

[Chem. 20]

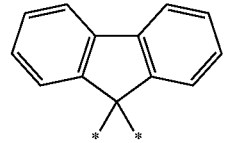

[Chem. 21]

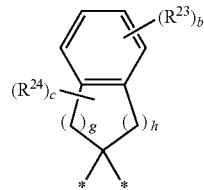

wherein $R^{23}$ and $R^{24}$ each independently represent an optionally substituted C1-C10 alkyl group, an optionally substituted C6-C20 aryl group, an optionally substituted C6-C20 aryloxy group, an optionally substituted C6-C20 arylthio group, an optionally substituted C6-C20 arylalkenyl group, an optionally substituted C7-C20 arylalkyl group, an optionally substituted C2-C20 heterocyclic ring-containing group, or a halogen atom; the methylene moiety of the alkyl and arylalkyl group being optionally replaced by an unsaturated bond, —O—, or —S—; adjacent $R^{23}$'s may be taken together to form a ring; b represents a number of 0 to 4; c represents a number of 0 to 8; g represents a number of 0 to 4; and h represents a number of 0 to 4; provided that the sum of g and h is 2 to 4.

[Chem. 22]

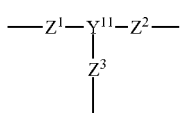

(7)

wherein $Y^{11}$ represents a trivalent C3-C35 aliphatic hydrocarbon group, a trivalent C3-C35 alicyclic hydrocarbon group, a trivalent C6-C35 aromatic ring-containing hydrocarbon group, or a trivalent C2-C35 heterocyclic ring-containing group; $Z^1$, $Z^2$, and $Z^3$ each independently represent a single bond, —O—, —S—, >CO, —CO—O—, —O—CO—, —SO$_2$—, —SS—, —SO—, >$NR^{32}$, >$PR^{32}$, an optionally substituted C1-C35 aliphatic hydrocarbon group, an optionally substituted C6-C35 aromatic ring-containing hydrocarbon group, or an optionally substituted C2-C35 heterocyclic ring-containing group; and $R^{32}$ represents a hydrogen atom, an optionally substituted C1-C35 aliphatic hydrocarbon group, an optionally substituted C6-C35 aromatic ring-containing hydrocarbon group, or an optionally substituted C2-C35 heterocyclic ring-containing group, the aliphatic hydrocarbon group, C6-C35 aromatic ring-containing hydrocarbon group, or C2-C35 heterocyclic ring-containing group being optionally substituted by carbon-carbon double —O—, —CO—, —O—CO—, —CO—O—, or —SO$_2$—.

[Chem. 23]

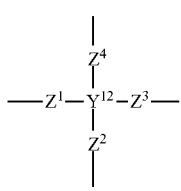

(9)

wherein $Y^{12}$ represents a carbon atom, a tetravalent C1-C35 aliphatic hydrocarbon group, a tetravalent C6-C35 aromatic ring-containing hydrocarbon group, or a tetravalent C2-C35 heterocyclic ring-containing group; the aliphatic hydrocarbon group, C6-C35 aromatic ring-containing hydrocarbon group, or C2-C35 heterocyclic ring-containing group being optionally substituted by —COO—, —O—, —OCO—, —NHCO—, —NH— or —CONH—; and $Z^1$, $Z^2$, $Z^3$, and $Z^4$ each independently have the same meaning as $Z^1$ to $Z^3$ in general formula (7).

[Chem. 24]

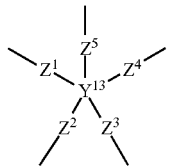

(10)

wherein $Y^{13}$ represent a pentavalent C2-C35 aliphatic hydrocarbon group, a pentavalent C6-C30 aromatic ring-containing hydrocarbon group, or a pentavalent C2-C30 heterocyclic ring-containing group, the aliphatic hydrocarbon group, C6-C35 aromatic ring-containing hydrocarbon group, or C2-C35 heterocyclic ring-containing group being optionally substituted by —COO—, —O—, —OCO—, —NHCO—, —NH— or —CONH—; and $Z^1$, $Z^2$, $Z^3$, $Z^4$, and $Z^5$ each independently have the same meaning as $Z^1$ to $Z^3$ in general formula (7).

[Chem. 25]

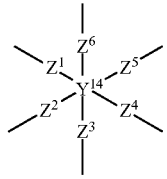

(11)

wherein $Y^{14}$ represents a hexavalent C2-C35 aliphatic hydrocarbon group, a hexavalent C6-C35 aromatic ring-containing hydrocarbon group, or a hexavalent C2-C35 heterocyclic ring-containing group; the aliphatic hydrocarbon group, C6-C35 aromatic ring-containing hydrocarbon group, or C2-C35 heterocyclic ring-containing group being optionally substituted by —COO—, —O—, —OCO—, —NHCO—, —NH— or —CONH—; and $Z^1$, $Z^2$, $Z^3$, $Z^4$, $Z^5$, and $Z^6$ each independently have the same meaning as $Z^1$ to $Z^3$ in general formula (7).

Examples of the divalent C1-C35 aliphatic hydrocarbon group represented by $X^1$ in general formula (12) include divalent groups derived from methane, ethane, propane, iso-propane, butane, sec-butane, tert-butane, isobutane, hexane, 2-methylhexane, 3-methylhexane, heptane, 2-methylheptane, 3-methylheptane, isoheptane, tert-heptane, 1-methyloctane, isooctane, tert-octane, cyclopropane, cyclobutane, cyclopentane, cyclohexane, cycloheptane, 2,4-dimethylcyclobutane, 4-methylcyclohexane, and so on by substitution with $Z^1$ and $Z^2$. These groups may be interrupted by —O—, —S—, —CO—, —COO—, —OCO—, —NH—, or a combination thereof.

Examples of the divalent C6-C35 aromatic ring-containing group represented by $X^1$ include and divalent groups derived from phenylene, naphthylene, and so on by substitution with $Z^1$ and $Z^2$.

Examples of the divalent C2-C35 heterocyclic ring-containing group represented by $X^1$ include divalent groups derived from pyridine, pyrazine, piperidine, piperazine, pyrimidine, pyridazine, triazine, hexahydrotriazine, furan, tetrahydrofuran, chromane, xanthene, thiophene, thiolane, and so on by substitution with $Z^1$ and $Z^2$.

These groups may be substituted by halogen, cyano, nitro, or C1-C8 alkoxy.

Examples of the C1-C8 alkyl group represented by $R^{32}$ and $R^{33}$ in $X^1$ of general formula (12) include methyl, ethyl, propyl, isopropyl, butyl sec-butyl, tert-butyl, isobutyl, amyl, isoamyl, tert-amyl, cyclopentyl, hexyl, 2-hexyl, 3-hexyl, cyclohexyl, 4-methylcyclohexyl, heptyl, 2-heptyl, 3-heptyl, isoheptyl, tert-heptyl, 1-octyl, isooctyl, and tert-octyl.

Examples of the C6-C20 aryl group as represented by $R^{32}$ and $R^{33}$ include phenyl, naphthyl, 2-methylphenyl, 3-methylphenyl, 4-methylphenyl, 4-vinylphenyl, 3-isopropylphenyl, 4-isopropylphenyl, 4-butylphenyl, 4-isobutylphenyl 4-tert-butylphenyl, 4-hexylphenyl, 4-cyclohexylphenyl, 4-octylphenyl, 4-(2-ethylhexyl)phenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4-di-tert-butylphenyl, 2,5-di-tert-butylphenyl, 2,6-di-tert-butylphenyl, 2,4-di-tert-pentylphenyl, 2,5-di-tert-amylphenyl, and 2,4,5-trimethylphenyl.

Examples of the C7-C20 arylalkyl group represented by $R^{32}$ and $R^{33}$ include benzyl, phenethyl, 2-phenylpropan-2-yl, diphenylmethyl, triphenylmethyl, styryl, and cinnamyl.

Examples of the C3-C10 cycloalkyl group represented by $R^{21}$ in the group of [Chem. 19] include cyclopropyl, cyclobutyl, cyclopentyl, cycloheptyl, cyclooctyl, and their derivatives substituted by C1-C10 alkyl or C1-C10 alkoxy.

Examples of the C1-C10 alkyl, C1-C10 alkoxy, and halogen represented by $R^{22}$ in general formula (A) include those described supra with respect to general formula (1).

Examples of the C2-C10 alkenyl represented by $R^{22}$ include vinyl, allyl, 1-propenyl, isopropenyl, 2-butenyl, 1,3-butadienyl, 2-pentenyl, and 2-octenyl.

The alkyl, alkoxy, and alkenyl as $R^{22}$ may be substituted with halogen at any position thereof.

The C1-C10 alkyl group, C6-C20 aryl group, and C7-C20 arylalkyl group represented by $R^{21}$ in the group of [Chem. 21] include the alkyl groups, aryl groups, and arylalkyl groups enumerated above to describe general formula (1) and their halogen-substituted derivatives.

Examples of the C6-C20 aryloxy group include phenyloxy, naphthyloxy, 2-methylphenyloxy, 3-methylphenyloxy, 4-methylphenyloxy, 4-vinylphenyloxy, 3-isopropylphenyloxy, 4-isopropylphenyloxy, 4-butylphenyloxy, 4-tert-butylphenyloxy, 4-hexylphenyloxy, 4-cyclohexylphenyloxy, 4-octylphenyloxy, 4-(2-ethylhexyl)phenyloxy, 2,3-dimethylphenyloxy, 2,4-dimethylphenyloxy, 2,5-dimethylphenyloxy, 2,6-dimethylphenyloxy, 3,4-dimethylphenyloxy, 3,5-dimethylphenyloxy, 2,4-di-tert-butylphenyloxy, 2,5-di-tert-butylphenyloxy, 2,6-di-tert-butylphenyloxy, 2,4-di-tert-pentylphenyloxy, 2,5-tert-amylphenyloxy, 4-cyclohexylphenyloxy, 2,4,5-trimethylphenyloxy, ferrocenyloxy, and their halogen-substituted derivatives.

Examples of the C6-C20 arylthio group include the above-enumerated halogen-substituted or unsubstituted C6-C20 aryloxy groups with their oxygen atom replaced with a sulfur atom.

Examples of the C8-C20 arylalkenyl group include the above-enumerated halogen-substituted or unsubstituted C6-C20 aryloxy groups with their oxygen atom replaced with an alkenyl group, e.g., vinyl, allyl, 1-propenyl, isopropenyl, 2-butenyl, 1,3-butadienyl, 2-pentenyl, or 2-octenyl.

Examples of the C2-C20 heterocyclic ring-containing group include pyridine, pyrazine, piperidine, piperazine, pyrimidine, pyridazine, triazine, hexahydrotriazine, furan, tetrahydrofuran, chromane, xanthene, thiophene, thiofuran, and their halogen-substituted derivatives.

Examples of the trivalent C3-C35 aliphatic hydrocarbon group represented by $Y^{11}$ in general formula (7) include those corresponding to the aliphatic hydrocarbon groups recited above to define $X^1$ of general formula (12) which are substituted by $Z^1$, $Z^2$, and $Z^3$ and may be interrupted by —O—, —S—, —CO—, —CO—O—, —O—CO—, —SO$_2$—, —NH—, or a combination thereof.

Examples of the trivalent C6-C35 aromatic ring-containing group represented by $Y^{11}$ include those corresponding to the aromatic ring-containing groups recited above to define $X^1$ of general formula (12) which are substituted by $Z^1$, $Z^2$, and $Z^3$.

Examples of the trivalent C2-C35 heterocyclic ring-containing group represented by $Y^{11}$ include those corresponding to the heterocyclic ring-containing groups recited above to define $X^1$ of general formula (12) which are substituted by $Z^1$, $Z^2$, and $Z^3$.

Examples of the tetravalent C1-C35 aliphatic hydrocarbon group represented by $Y^{12}$ in general formula (9) include those corresponding to the aliphatic hydrocarbon groups recited above to define $X^1$ of general formula (12) which are substituted by $Z^1$, $Z^2$, $Z^3$, and $Z^4$ and may be interrupted by —O—, —S—, —CO—, —COO—, —OCO—, —NH—, or a combination thereof.

Examples of the tetravalent C6-C35 aromatic ring-containing group represented by $Y^{12}$ include those corresponding to the aromatic ring-containing groups recited above to define $X^1$ of general formula (2) which are substituted by $Z^1$, $Z^2$, $Z^3$, and $Z^4$.

Examples of the tetravalent C2-C35 heterocyclic ring-contained group represented by $Y^{11}$ include those corresponding to the heterocyclic ring-containing groups recited above to define $X^1$ of general formula (12) which are substituted by $Z^1$, $Z^2$, $Z^3$, and $Z^4$.

Examples of the pentavalent C2-C35 aliphatic hydrocarbon group represented by $Y^{13}$ in general formula (10) include those corresponding to the aliphatic hydrocarbon groups recited above to define $X^1$ of general formula (12) which are substituted by $Z^1$, $Z^2$, $Z^3$, $Z^4$, and $Z^5$ and may be interrupted by —O—, —S—, —CO—, —CO—O—, —O—CO—, —SO$_2$—, —NH—, or a combination thereof.

Examples of the pentavalent C6-C35 aromatic ring-containing group represented by $Y^{13}$ include those corresponding to the aromatic ring-containing groups recited above to define $X^1$ of general formula (12) which are substituted by $Z^1$, $Z^2$, $Z^3$, $Z^4$, and $Z^5$.

Examples of the pentavalent C2-C35 heterocyclic ring-containing group represented by $Y^{13}$ include those corresponding to the heterocyclic ring-containing groups recited above to define $X^1$ of general formula (12) which are substituted by $Z^1$, $Z^2$, $Z^3$, $Z^4$, and $Z^5$.

Examples of the hexavalent C2-C35 aliphatic hydrocarbon group represented by $Y^{14}$ in general formula (11) include those corresponding to the aliphatic hydrocarbon 26 groups recited above to define $X^1$ of general formula (12) which are substituted by $Z^1$, $Z^2$, $Z^3$, $Z^4$, $Z^5$, and $Z^6$ and may be interrupted by —O—, —S—, —CO—, —COO—, —OCO—, —SO$_2$—, —NH—, or a combination thereof.

Examples of the hexavalent C6-C35 aromatic ring-containing group represented by $Y^{14}$ include those corresponding to the aromatic ring-containing groups recited above to define $X^1$ of general formula (12) which are substituted by $Z^1$, $Z^2$, $Z^3$, $Z^4$, $Z^5$, and $Z^6$.

Examples of the hexavalent C2-C35 heterocyclic ring-containing group represented by $Y^{14}$ include those corresponding to the heterocyclic ring-containing groups recited above to define $X^1$ of general formula (12) which are substituted by $Z^1$, $Z^2$, $Z^3$, $Z^4$, $Z^5$, and $Z^6$.

Of the compounds represented by general formula (1) preferred in terms of availability of starting materials and ease of preparation are those in which A is a benzene ring; those in which $R^1$ is C1-C8 alkyl, especially C4-C6 alkyl; those in which $R^4$ is C2-C9 alkoxycarbonyl, especially C5-C7 alkoxycarbonyl; those in which $X^2$ is a substituent represented by general formula (3) below, a substituent represented by general formula (4) below, or a substituent represented by [Chem. 26] shown below when n is 2; those in which $X^3$ is a group selected from a group represented by Group 1 shown below when n is 3; those in which $X^4$ is a group selected from a group represented by Group 2 shown below when n is 4; those in which $X^4$ is a group selected from a group represented by Group 3 below when n is 5; and those in which $X^4$ is a group represented by Group 4 shown below when n is 6.

[Chem. 26]

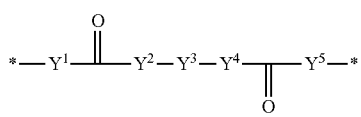

(3)

wherein $Y^1$ and $Y^5$ each independently represent a C1-C4 alkylene group; $Y^2$ and $Y^4$ each independently represent an oxygen atom or —$NR^{13}$—; $R^{13}$ represents a hydrogen atom or a C1-C20 aliphatic hydrocarbon group; $Y^3$ represents —$CR^{14}R^{15}$—, —$NR^{16}$—, a divalent C1-C35 aliphatic hydrocarbon group, a divalent C6-C35 aromatic ring-containing group, or a substituent represented by general formula (5) below, the aliphatic hydrocarbon group, C6-C35 aromatic ring-containing hydrocarbon group, or C2-C35 heterocyclic ring-containing group being optionally substituted by —COO—, —O—, —OCO—, —NHCO—, —NH—, or —CONH—; $R^{14}$ and $R^{15}$ each independently represent a hydrogen atom, a C1-C8 alkyl group, a C6-C20 aryl group, or a C7-C20 arylalkyl group; $R^{16}$ represents a hydrogen atom, an optionally substituted C1-C35 aliphatic hydrocarbon group, an optionally substituted C6-C35 aromatic ring-containing hydrocarbon group, or an optionally substituted C2-C35 heterocyclic ring-containing group.

[Chem. 27]

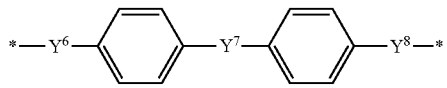

(4)

wherein $Y^6$ and $Y^8$ each independently represent —$NR^{17}$— or an optionally oxygen-substituted C1-C4 alkylene group; $Y^7$ represents a single bond, —O—, —S—, —$SO_2$—, —$CR^{18}R^{19}$—, or any one of the substituents represented by [Chem. 19] to [Chem. 21] shown above; $R^{17}$ represents a hydrogen atom or a C1-C20 aliphatic hydrocarbon group; $R^{18}$ and $R^{19}$ each independently represent a hydrogen atom or an optionally halogen-substituted C1-C8 alkyl group.

[Chem. 28]

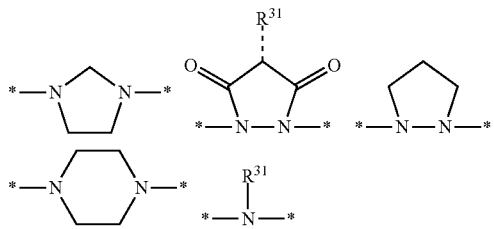

wherein $R^{31}$ represents a hydrogen atom, an optionally substituted C1-C35 aliphatic hydrocarbon group, an optionally substituted C6-C35 aromatic ring-containing hydrocarbon group, or an optionally substituted C2-C35 heterocyclic ring-containing group.

[Chem. 29]

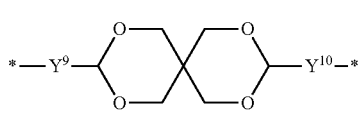

(5)

wherein $Y^9$ and $Y^{10}$ each independently represent a C1-C4 alkylene group.

[Chem. 30]

Group 1

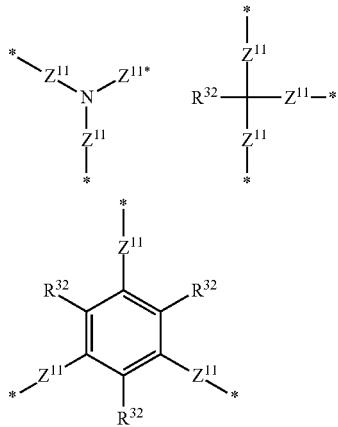

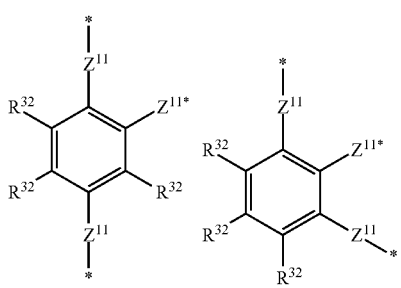

-continued

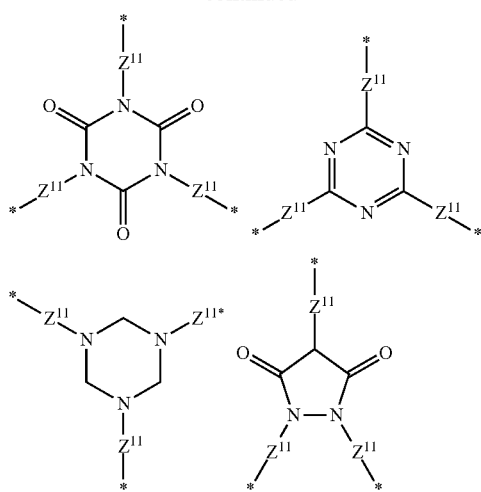

wherein $R^{32}$ has the same meaning as $R^{32}$ in general formula (7); when there are a plurality of $R^{32}$'s per group, they may be the same or different; and $Z^{11}$ has the same meaning as $Z^1$, $Z^2$, and $Z^3$.

[Chem. 31]

Group 2

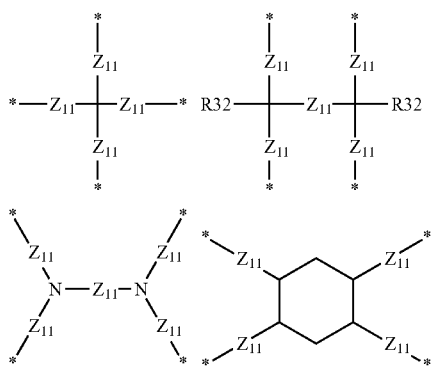

wherein $R^{32}$ has the same meaning as $R^{32}$ in general formula (7); when there are a plurality of $R^{32}$'s per group, they may be the same or different; and $Z^{11}$ has the same meaning as $Z^1$, $Z^2$, and $Z^3$.

[Chem. 32]

Group 3

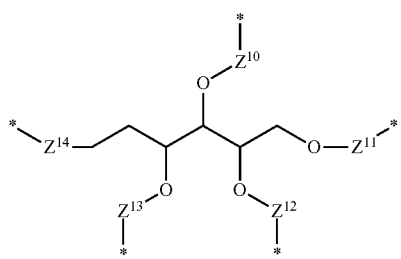

-continued

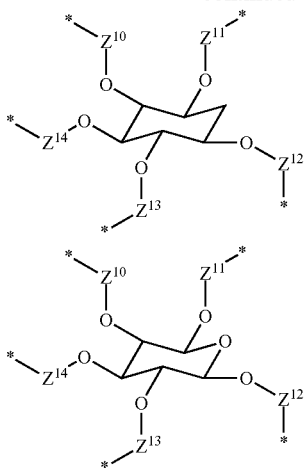

wherein $R^{32}$ has the same meaning as $R^{32}$ in general formula (7); when there are a plurality of $R^{32}$'s per group, they may be the same or different; and $Z^{10}$, $Z^{11}$, $Z^{12}$, $Z^{13}$, and $Z^{14}$ each have the same meaning as $Z^1$, $Z^2$, and $Z^3$.

[Chem. 33]

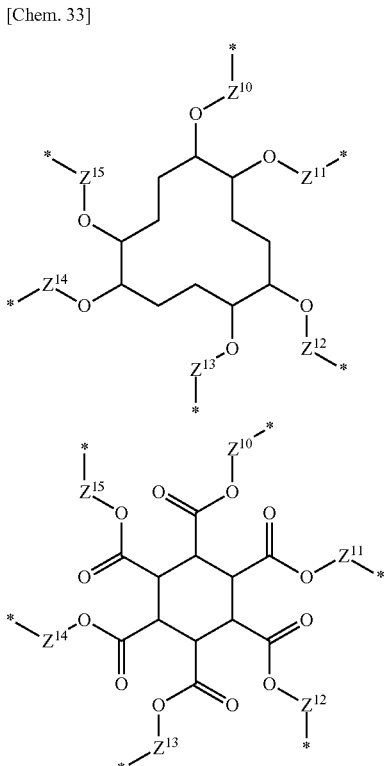

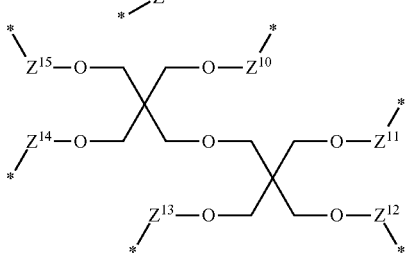

wherein $R^{32}$ has the same meaning as $R^{32}$ in general formula (7); when there are a plurality of $R^{32}$'s per group, they may be the same or different; and $Z^{10}$, $Z^{11}$, $Z^{12}$, $Z^{13}$, $Z^{14}$, and $Z^{15}$ each have the same meaning as $Z^1$, $Z^2$, and $Z^3$.
Specific examples of the compound represented by general formula (1) include, but are not limited to, the following compounds.
[Chem. 34]
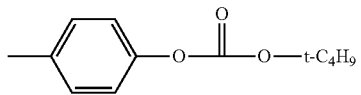
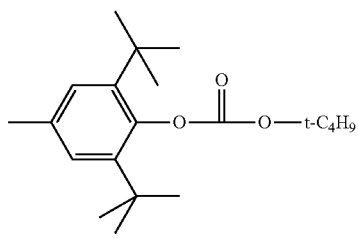
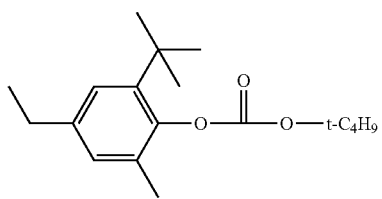
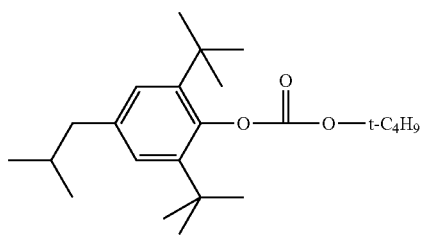
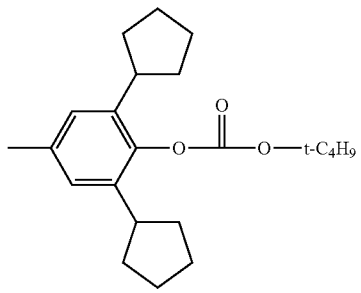
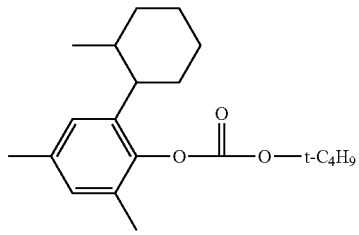
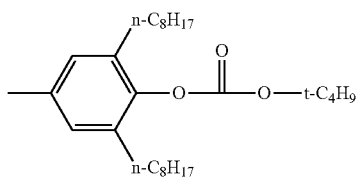
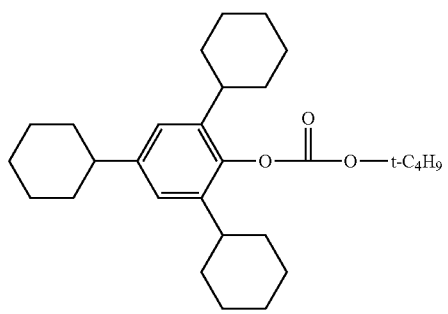
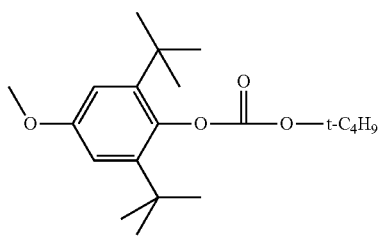
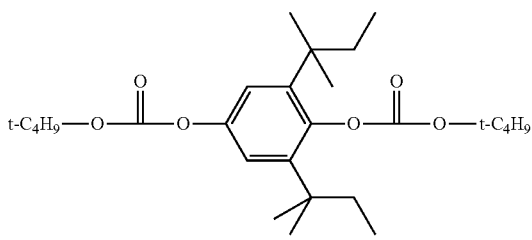

23
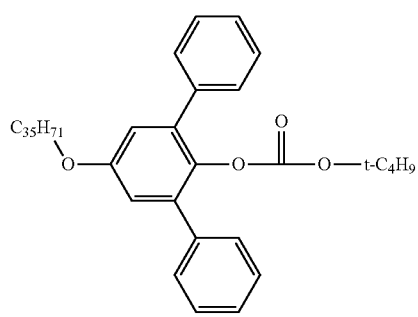
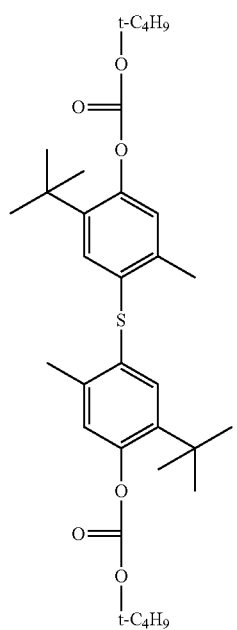
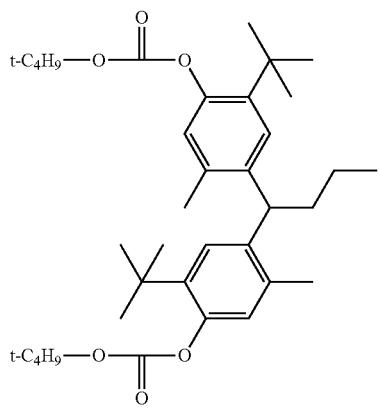
24
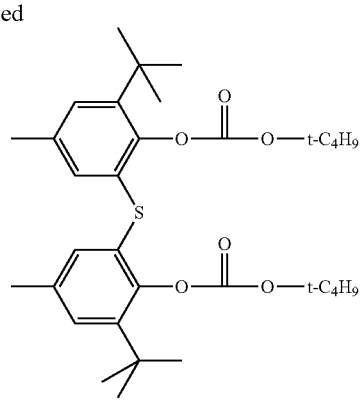
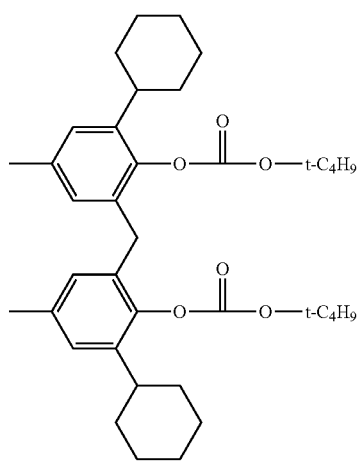

[Chem. 35]
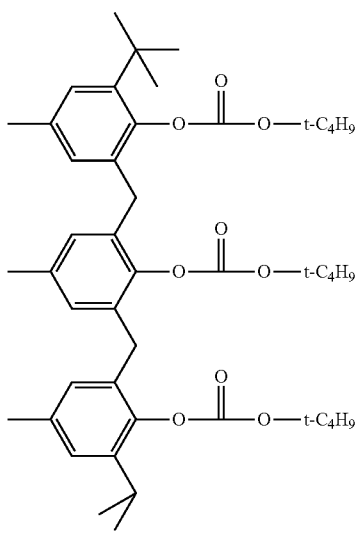
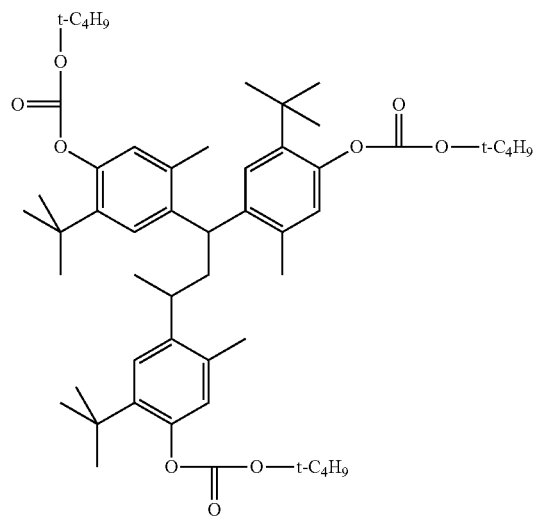
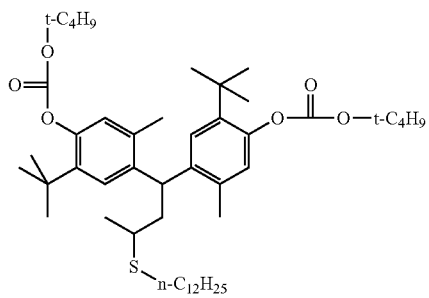
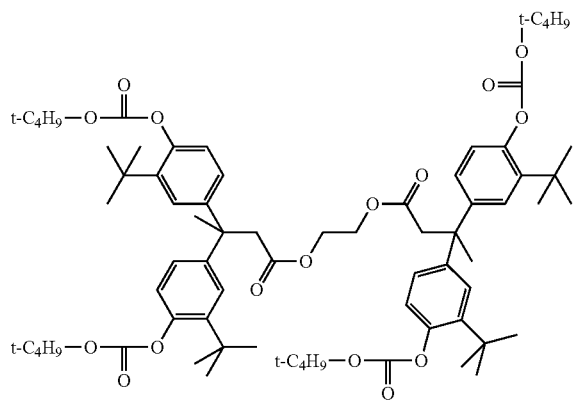
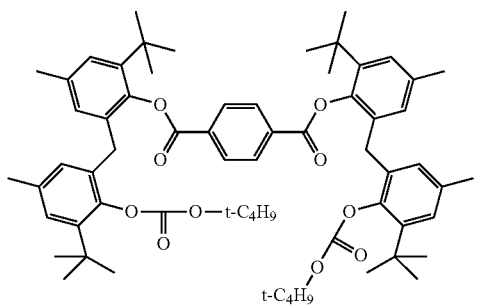
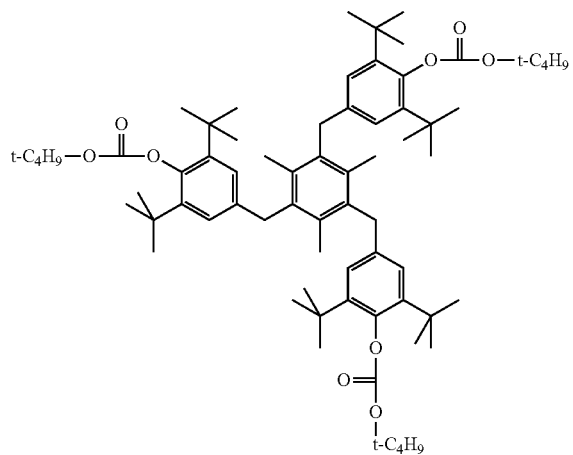

-continued
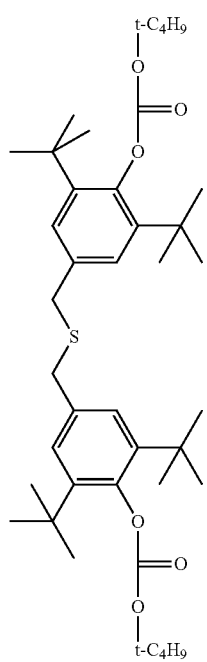
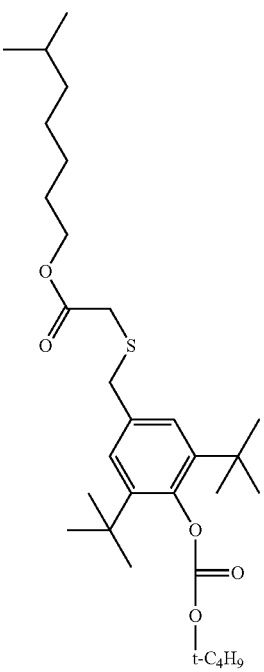
[Chem. 36]
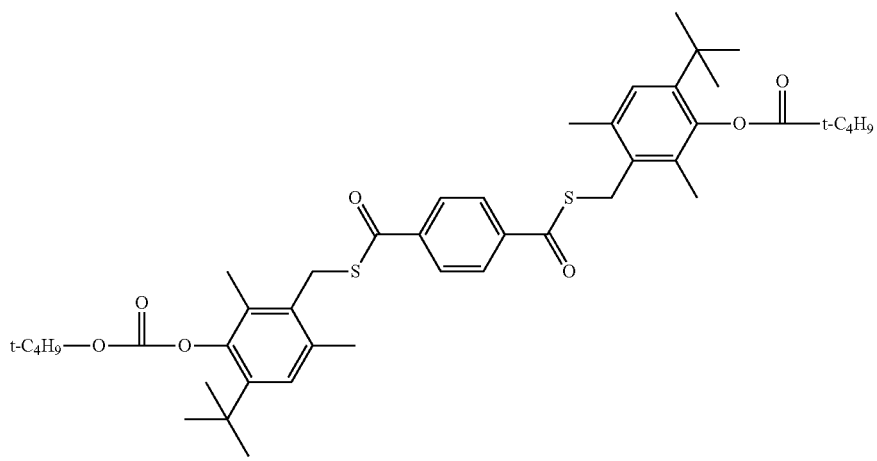
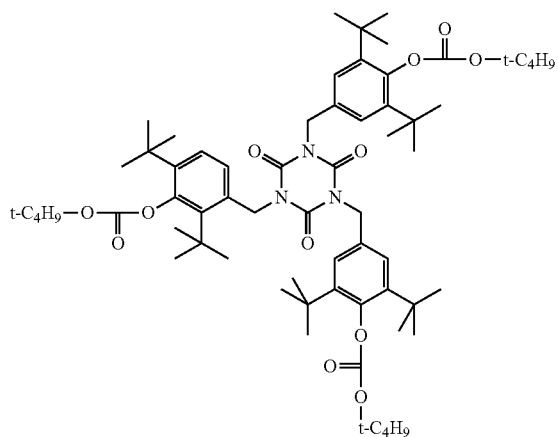
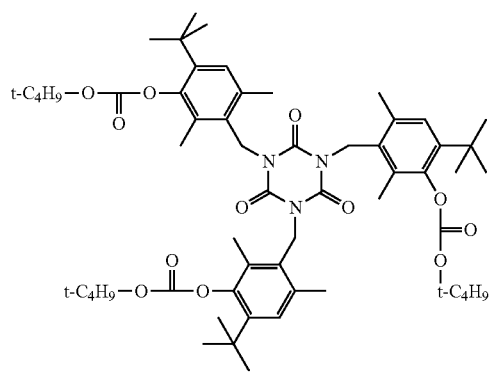

29
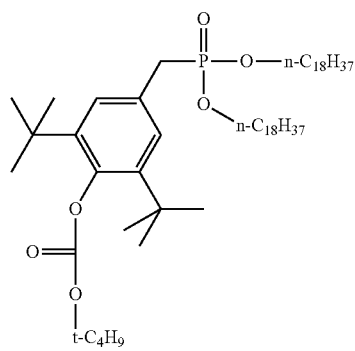
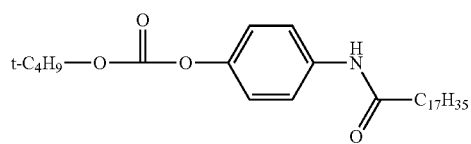
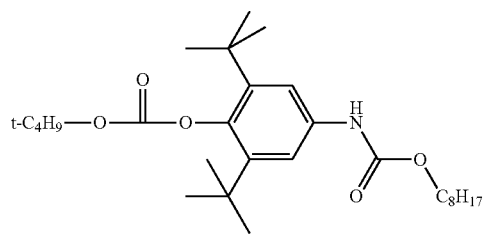
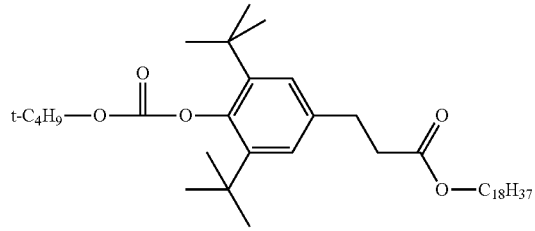
30
-continued
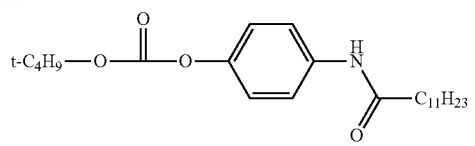
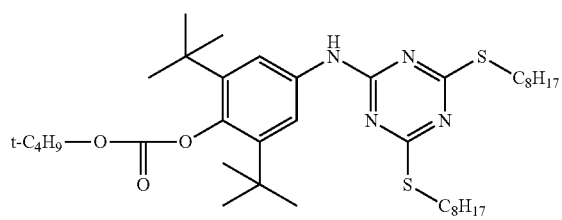
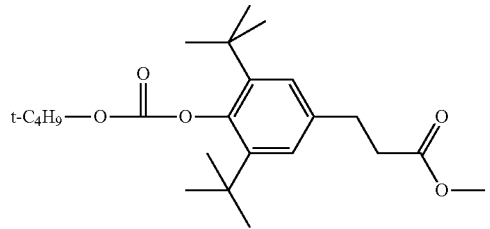
[Chem. 37]
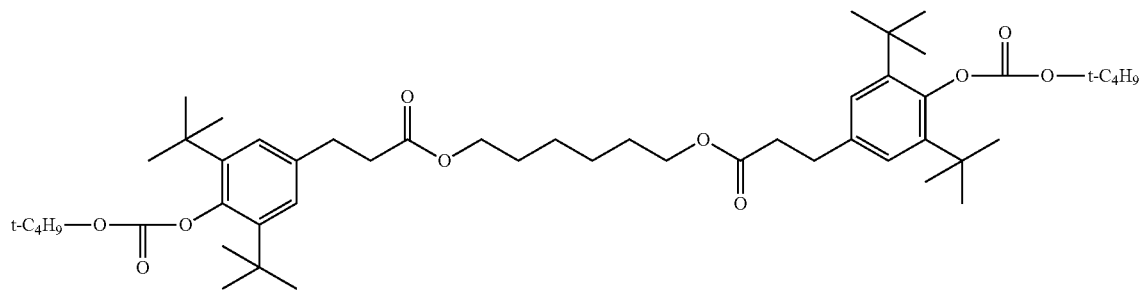
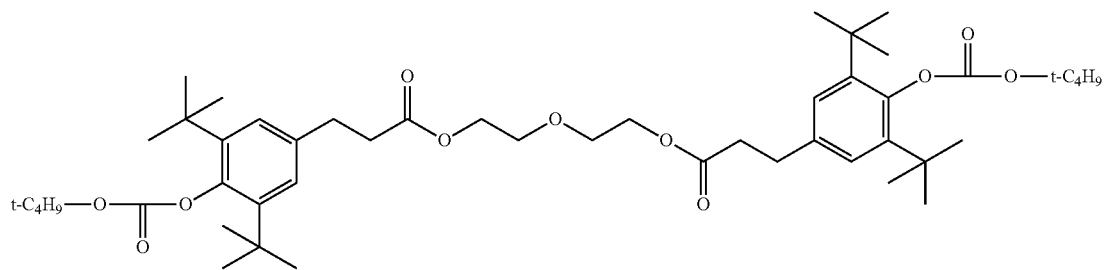

-continued
31 32
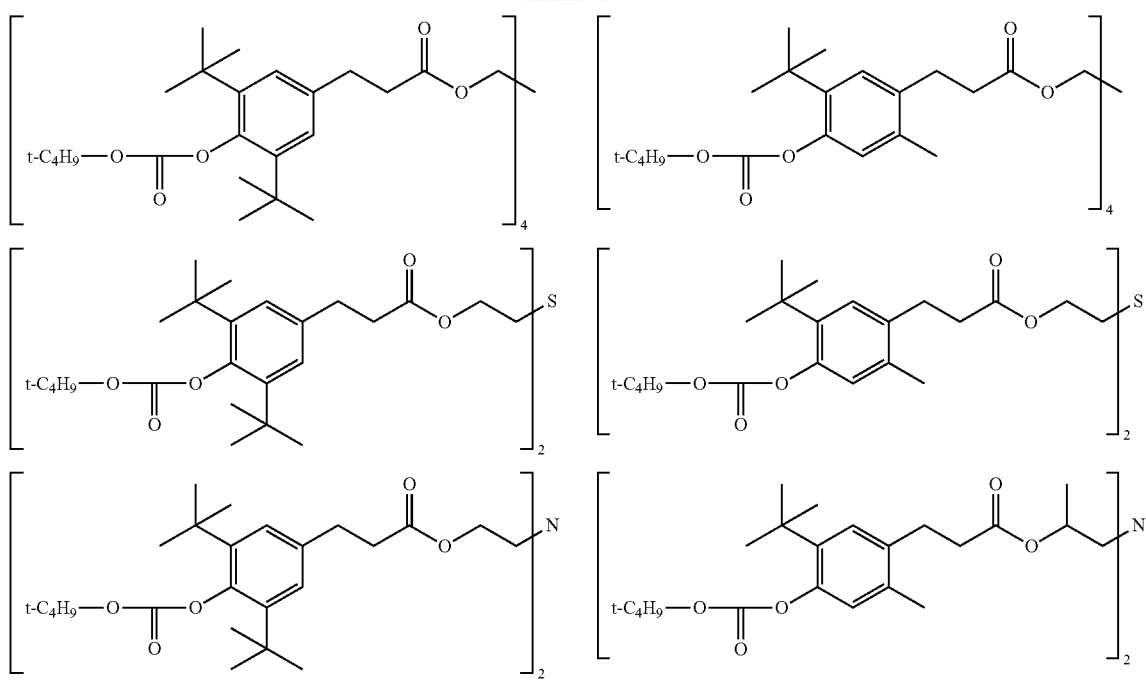
[Chem. 38]
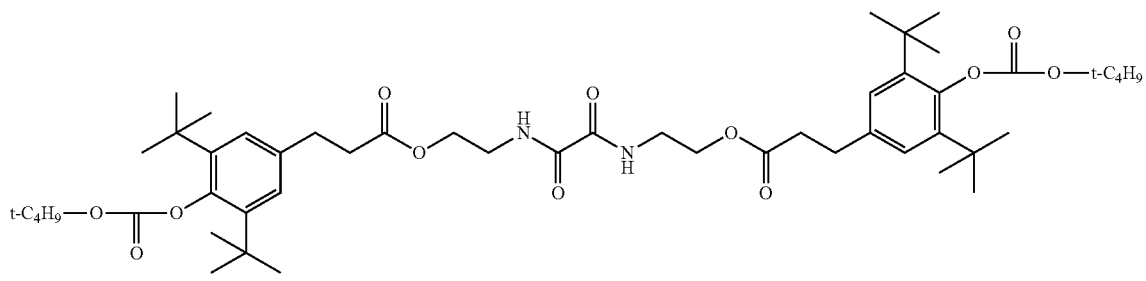
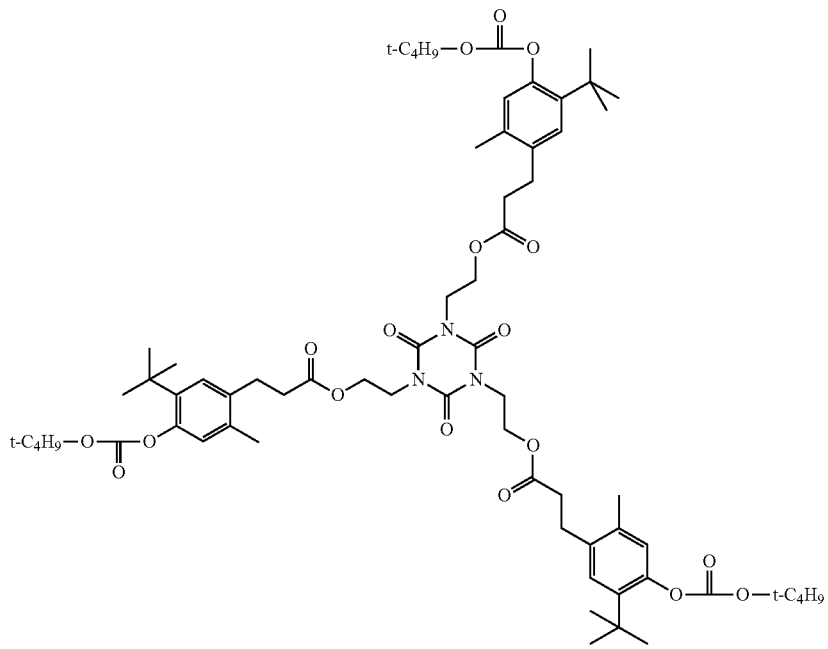

33 34
-continued
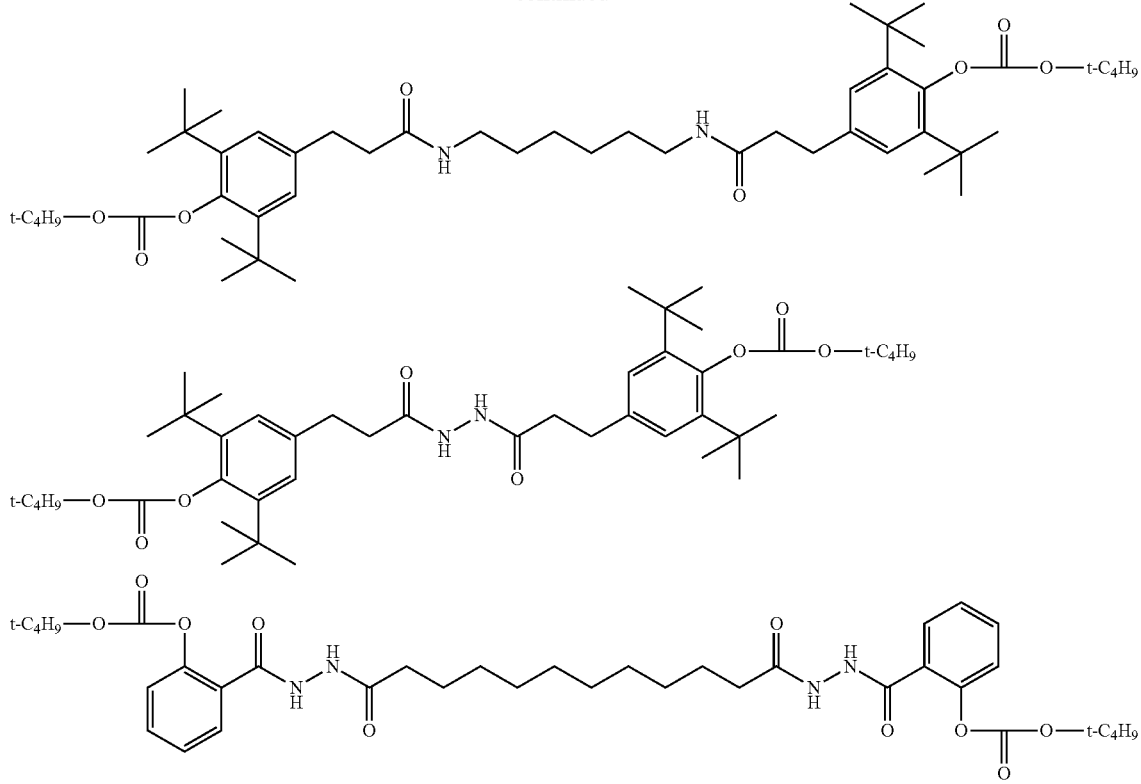
[Chem. 39]
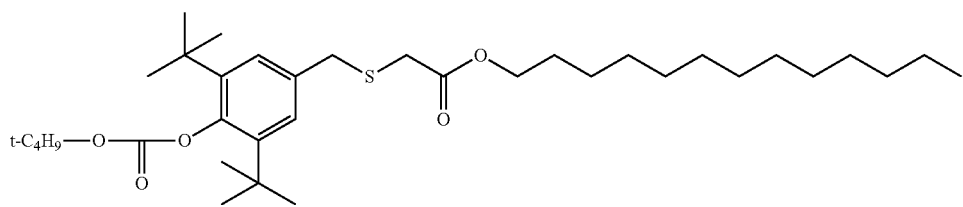
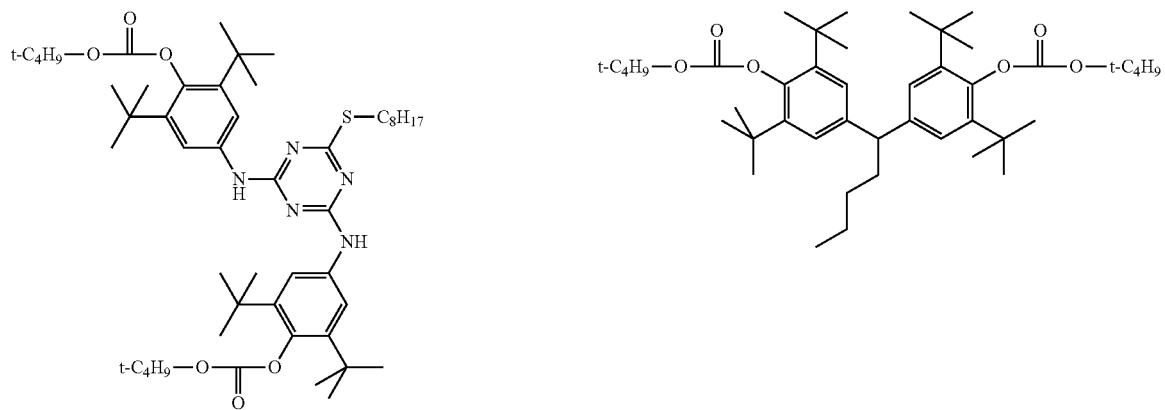

35
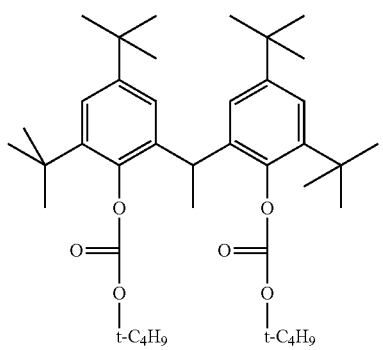
36
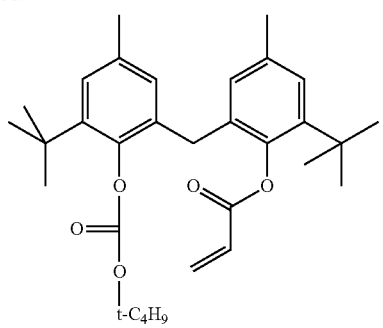
-continued
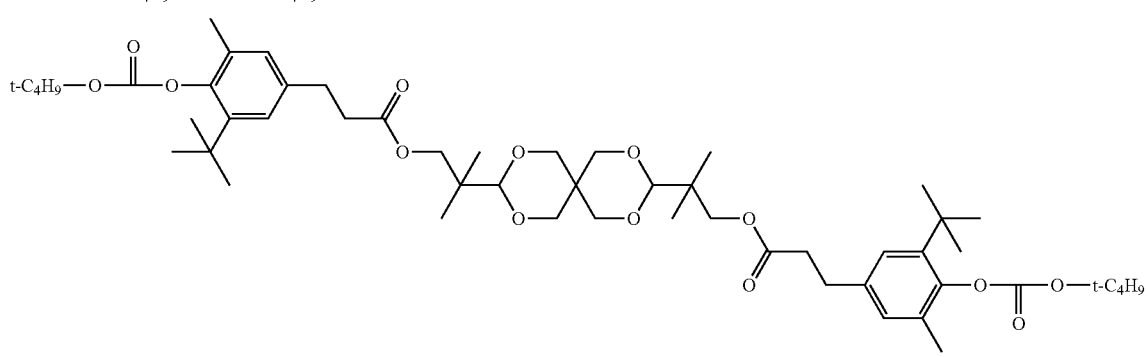
[Chem. 40]
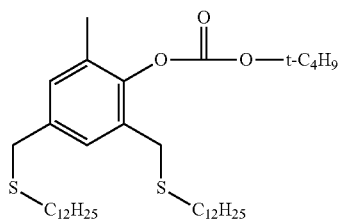
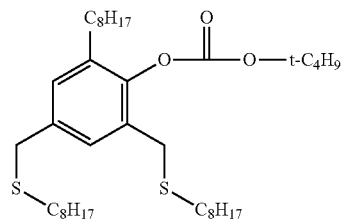
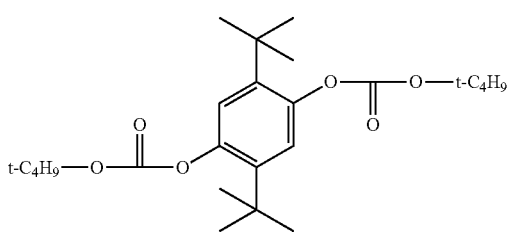
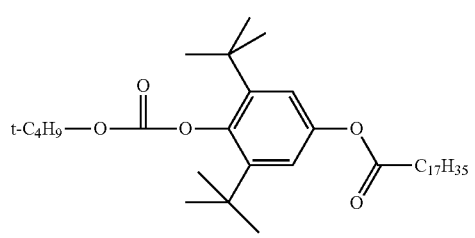
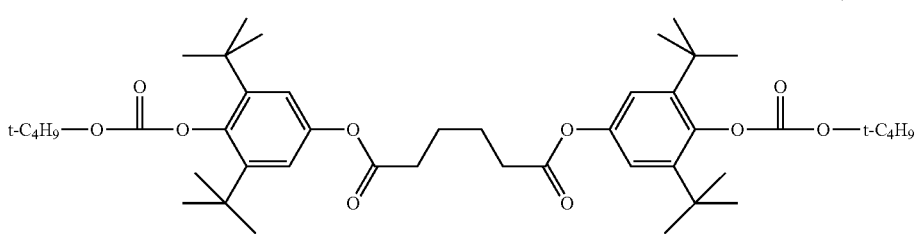
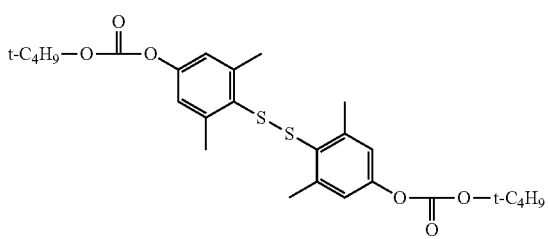
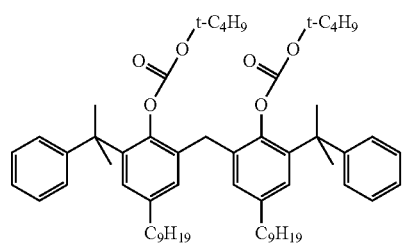

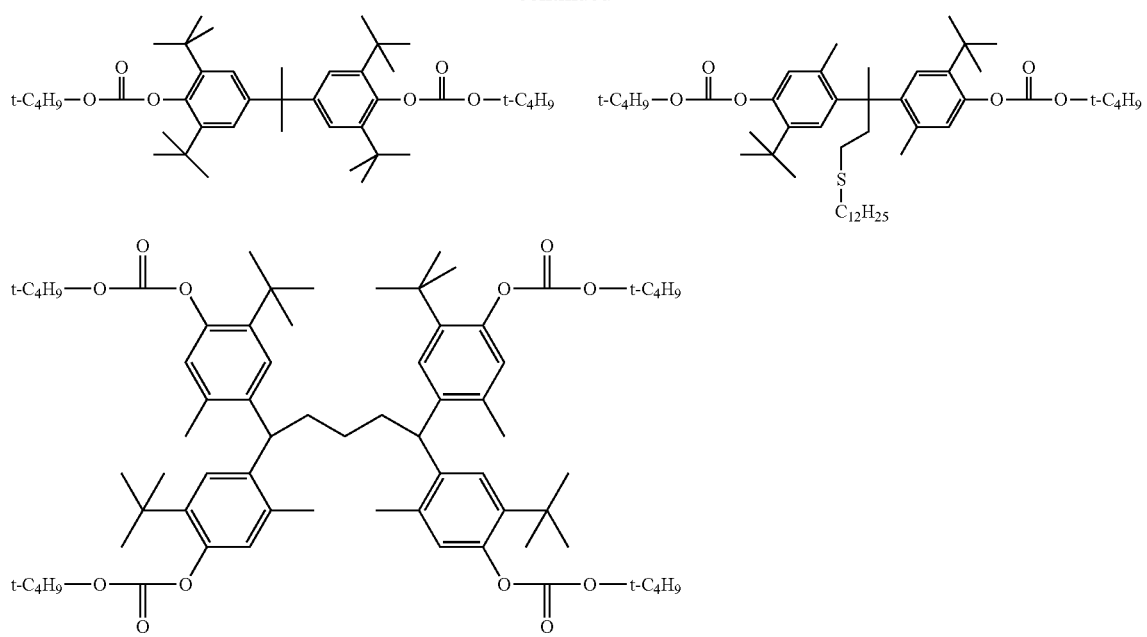
[Chem. 41]
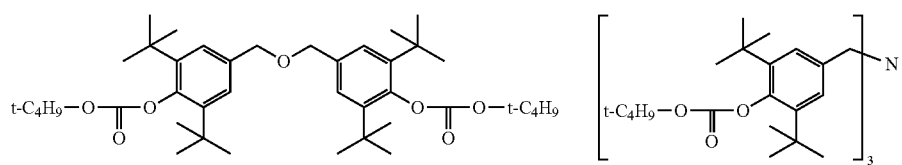
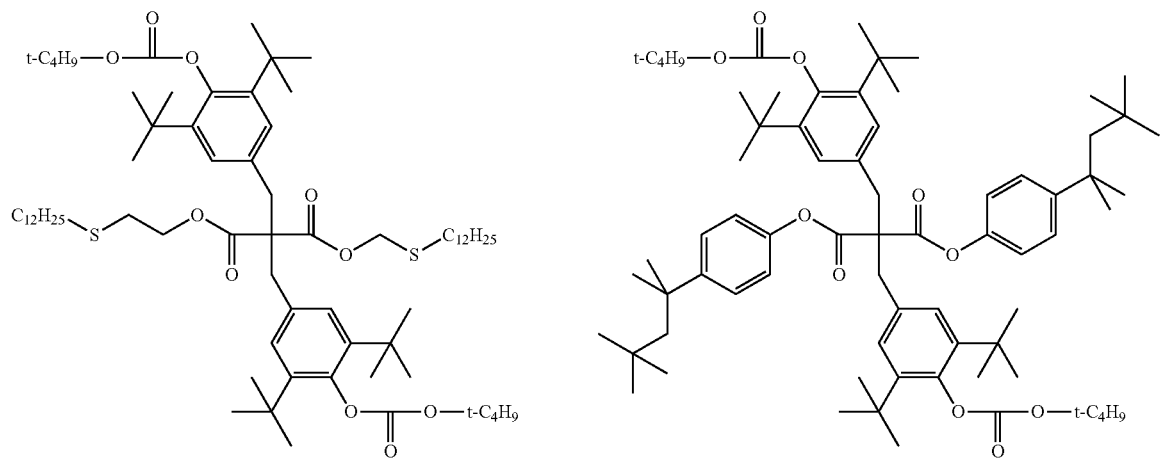
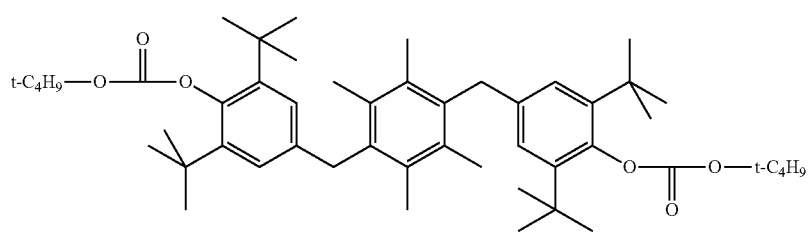

39
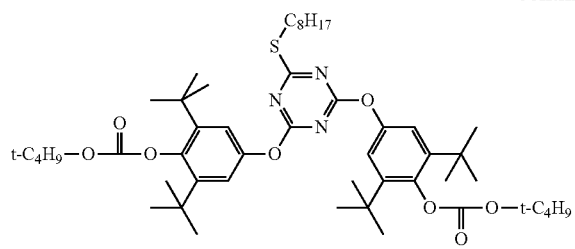
40
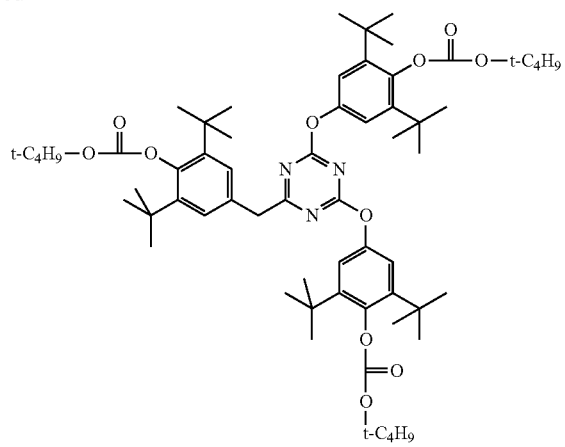
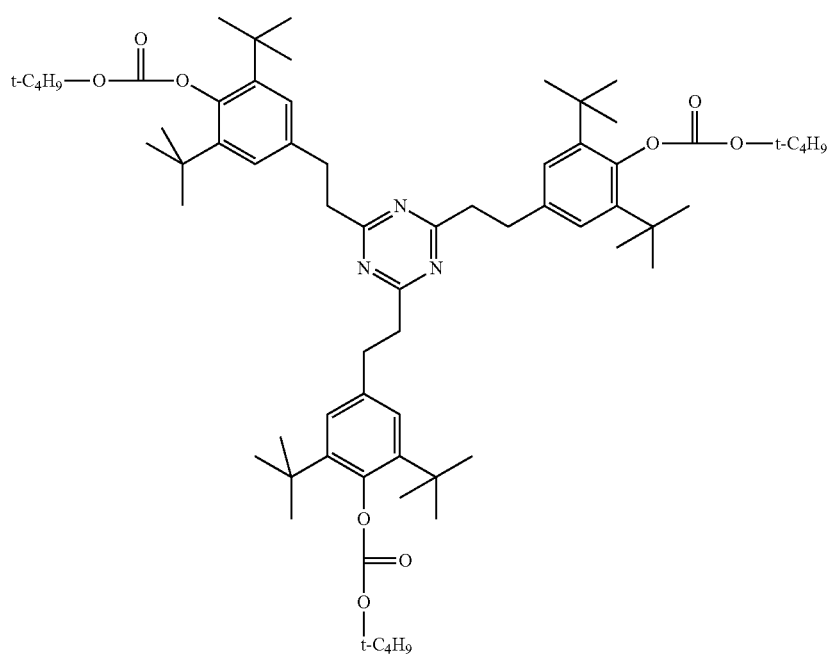

-continued
[Chem. 42]
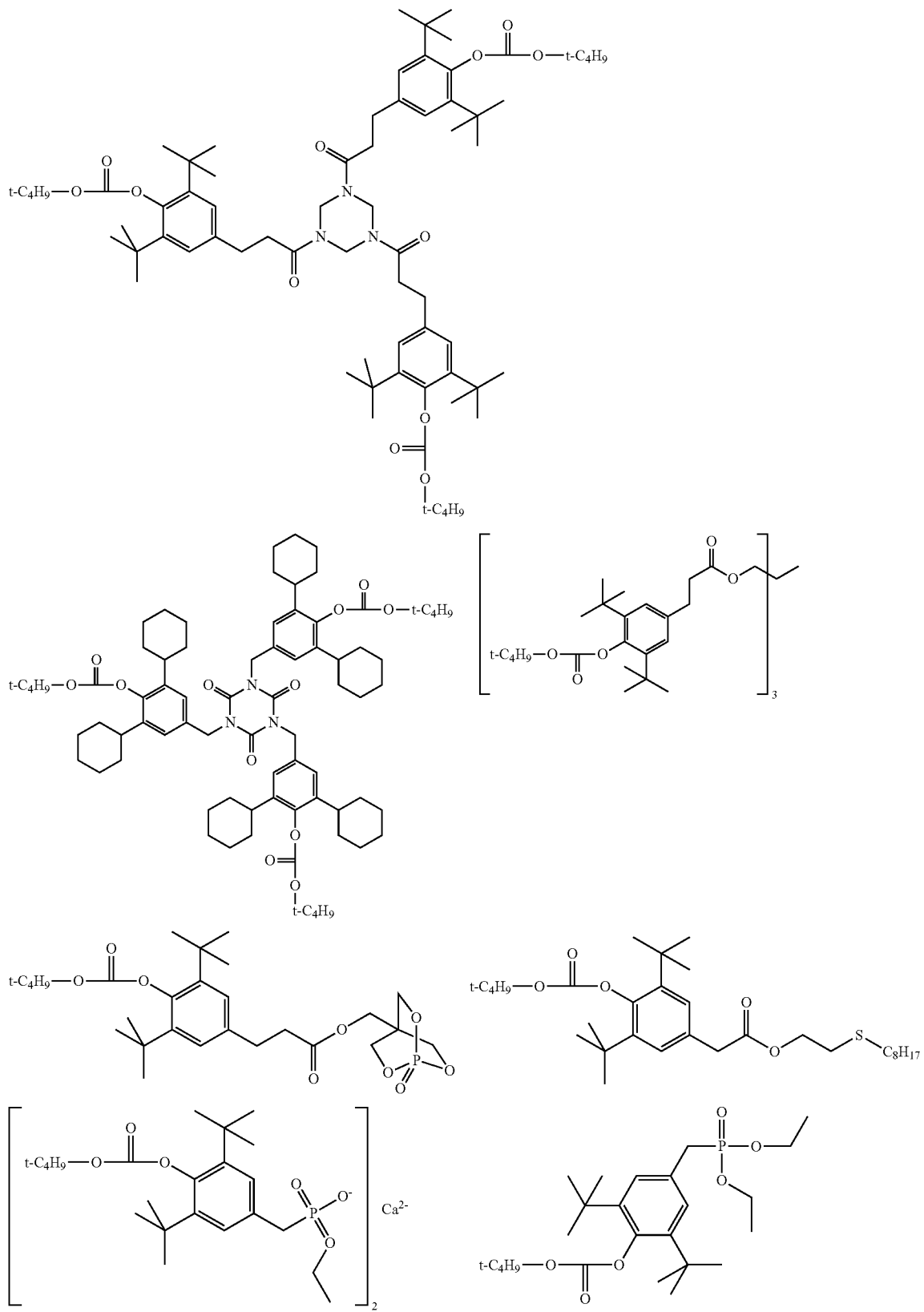

-continued
43
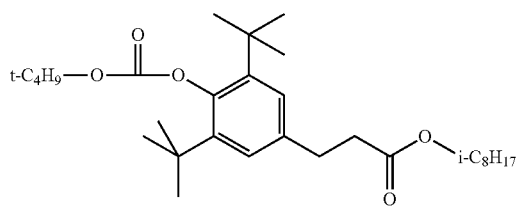
44
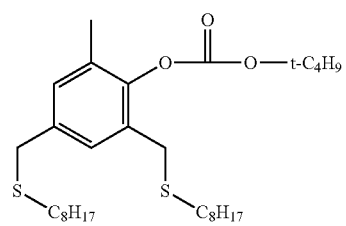
[Chem. 43]
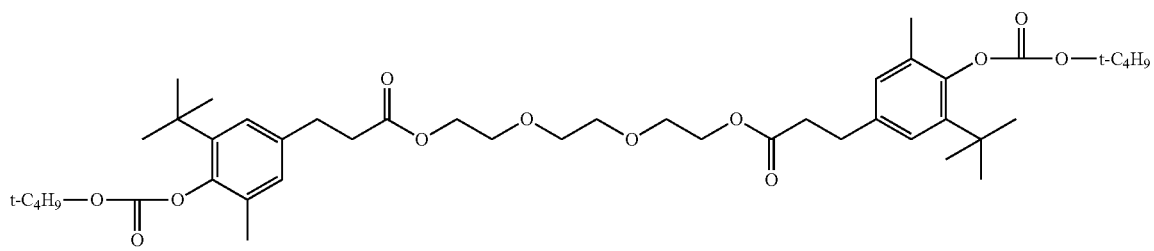
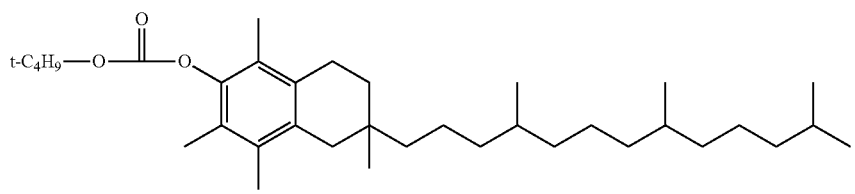
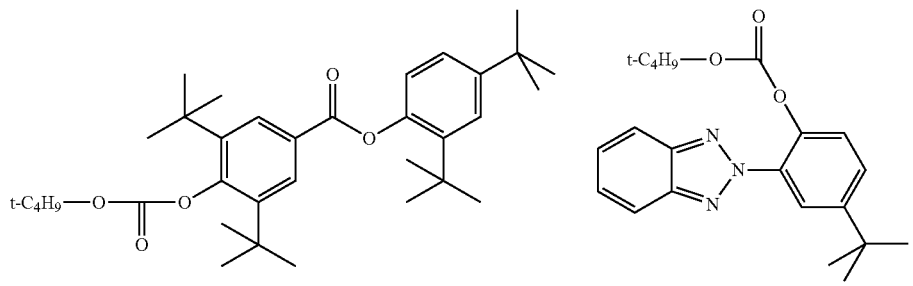
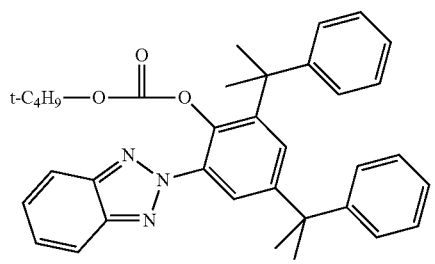
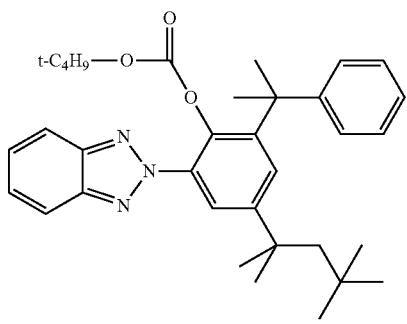

-continued
45
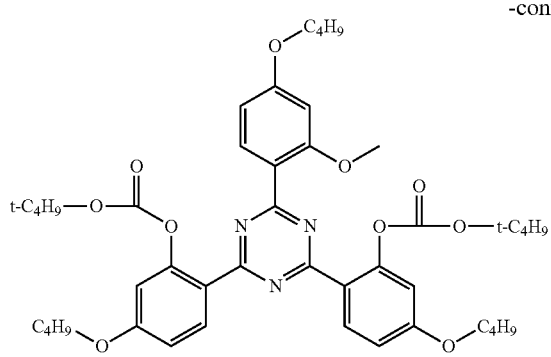
46
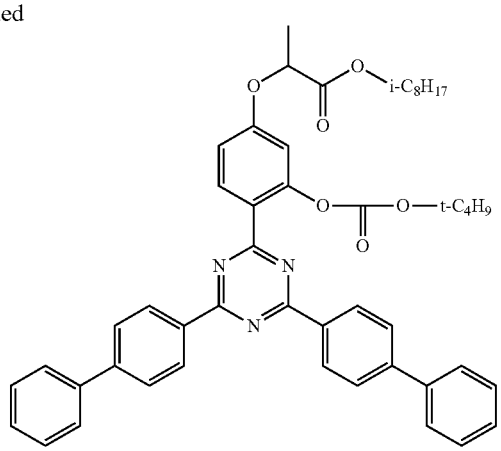
[Chem. 44]
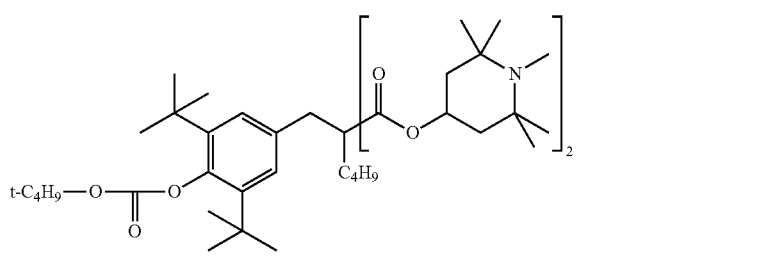
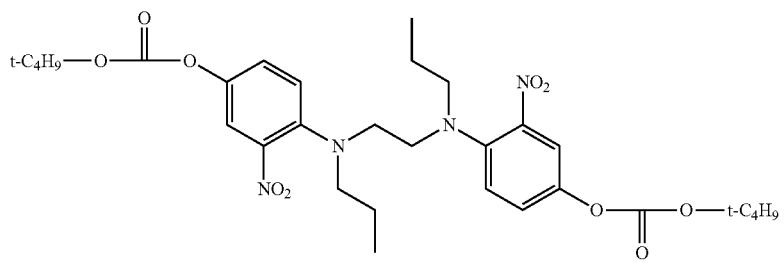
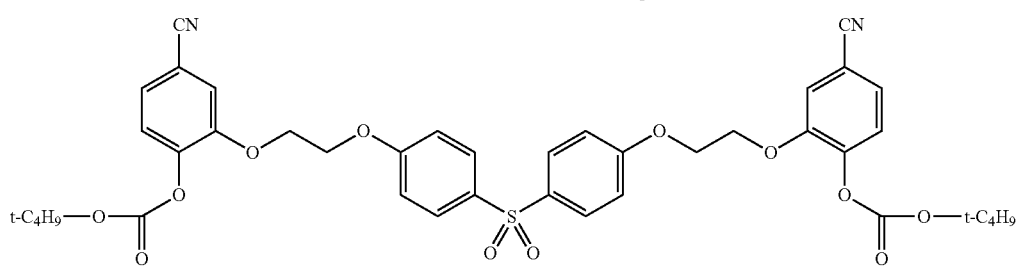
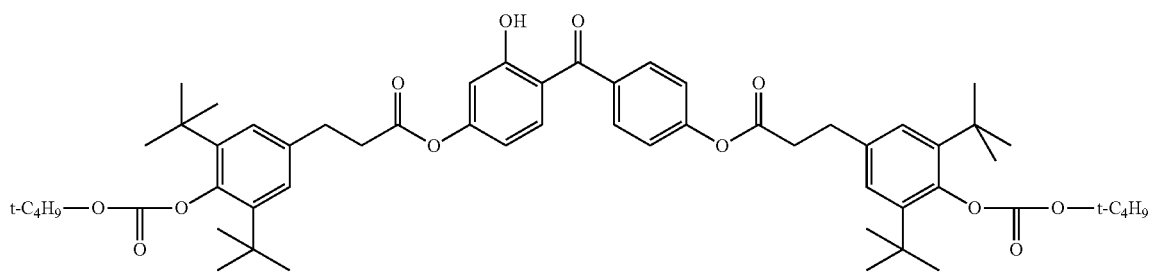

-continued
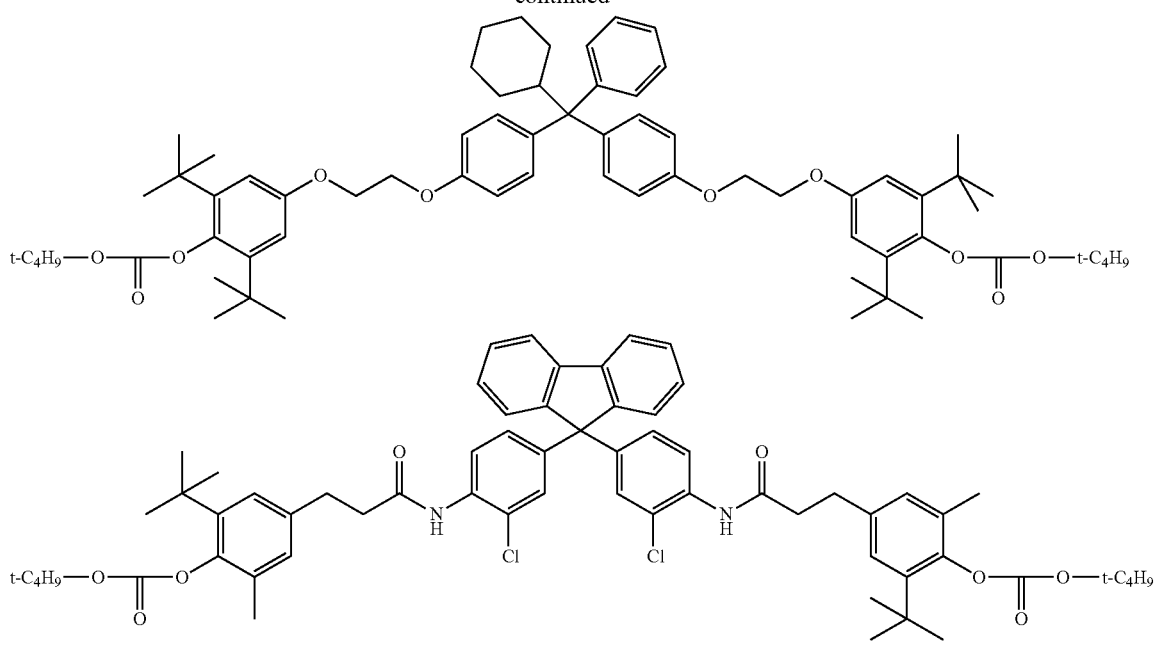
[Chem. 45]
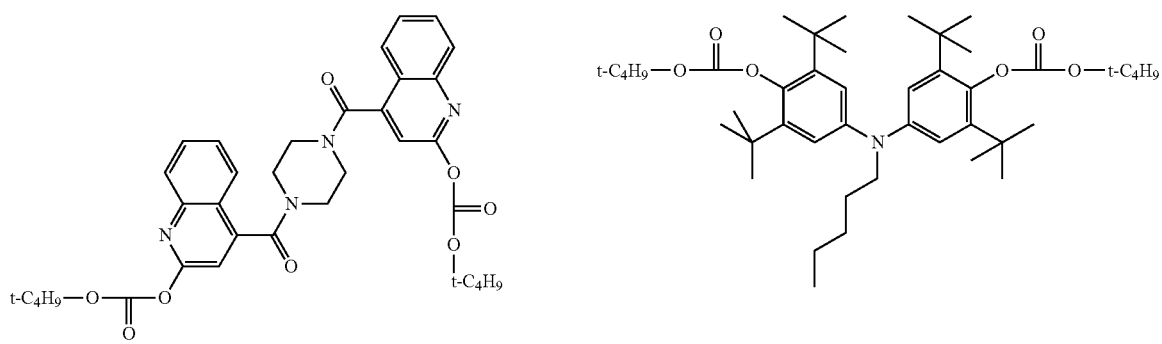
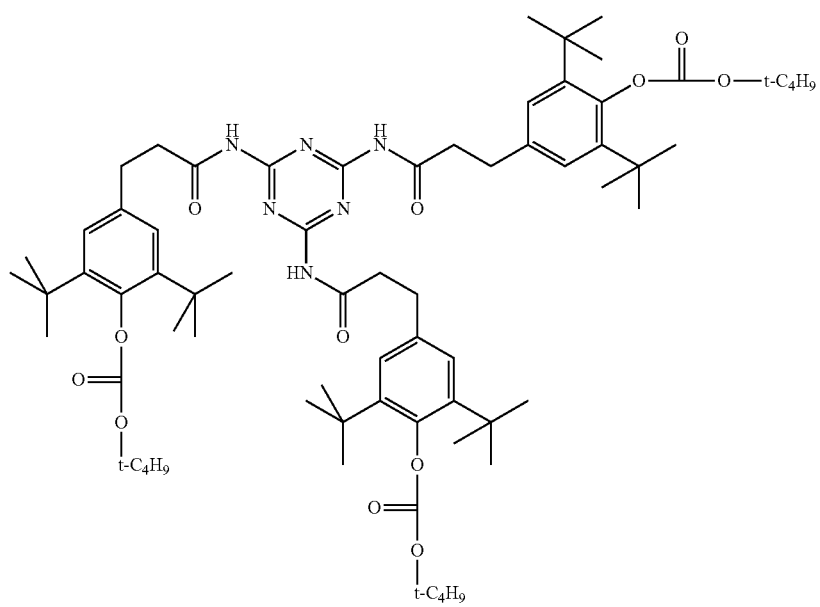

-continued
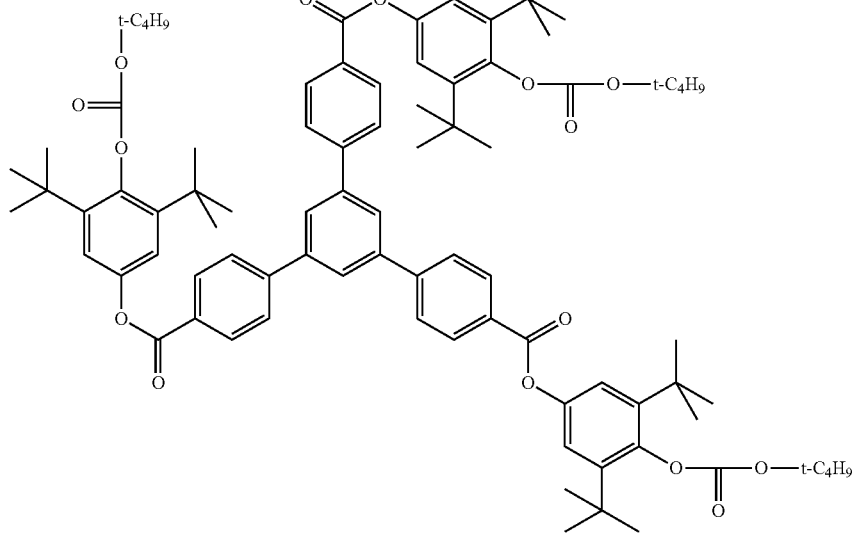
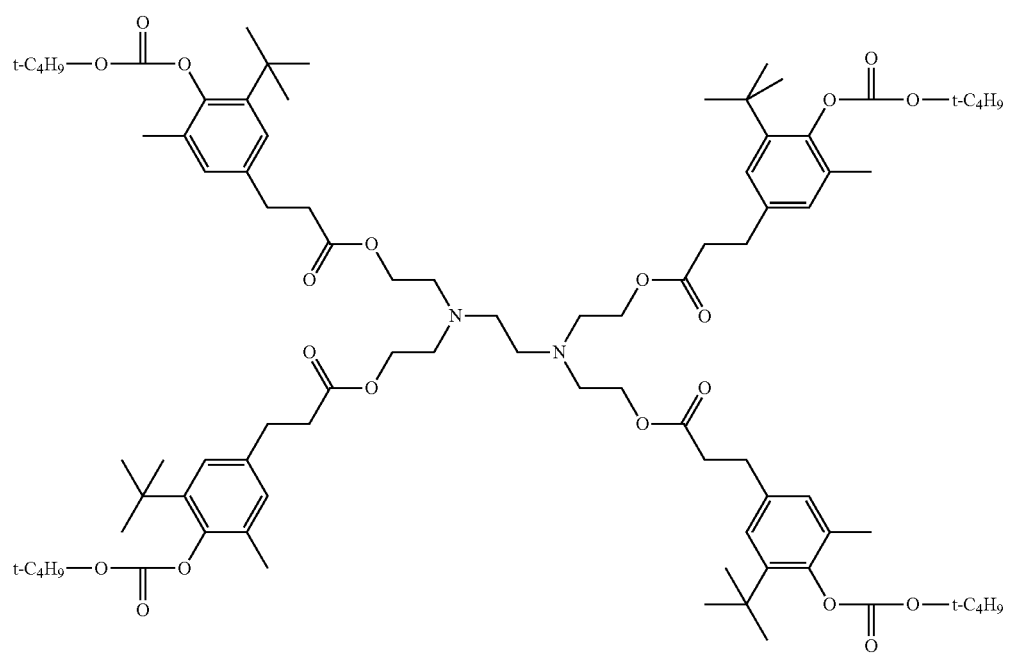

[Chem. 46]
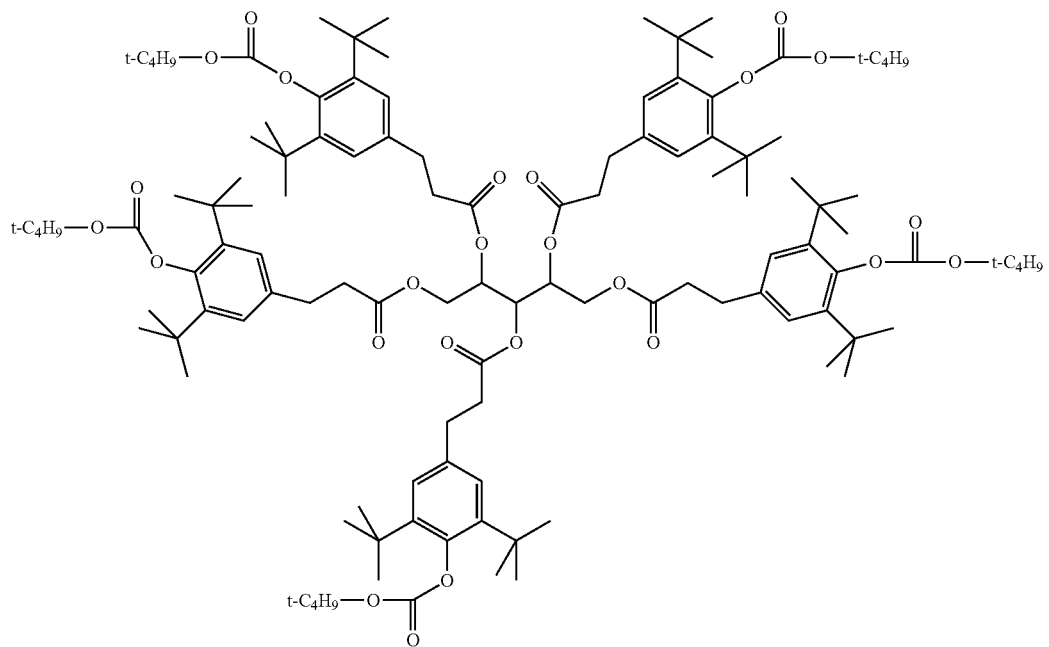
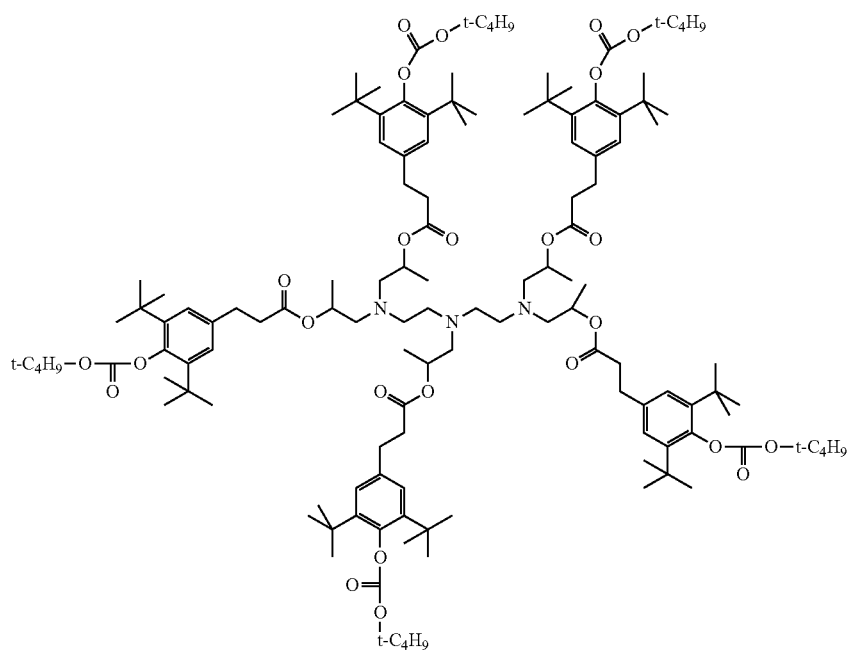

-continued
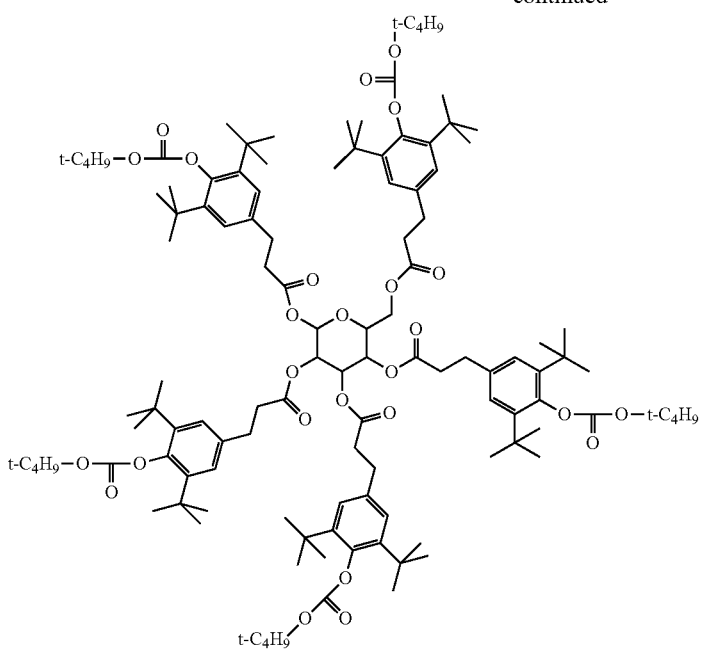
[Chem. 47]
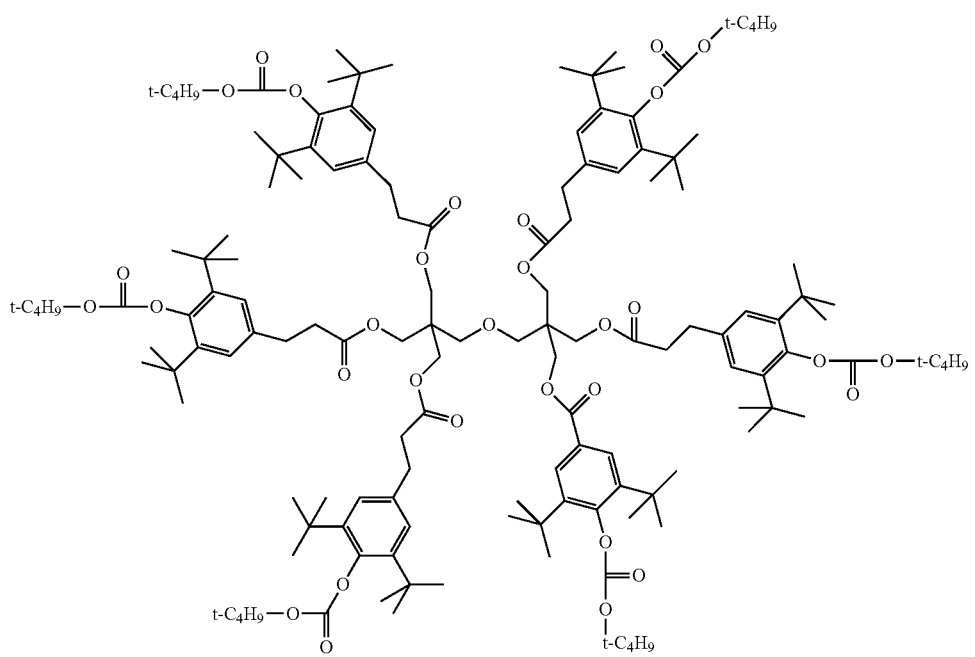

-continued
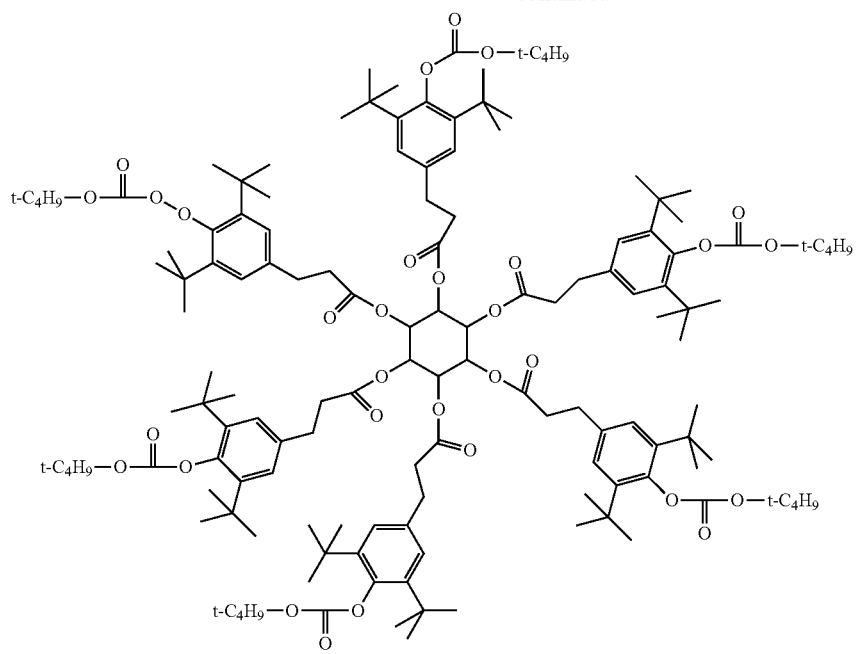
[Chem. 48]
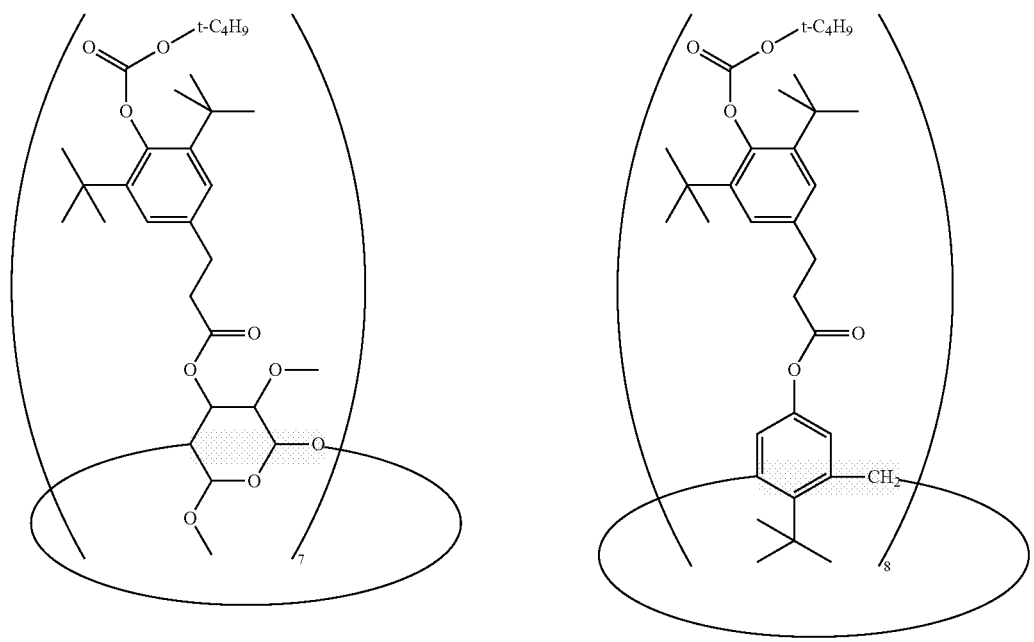
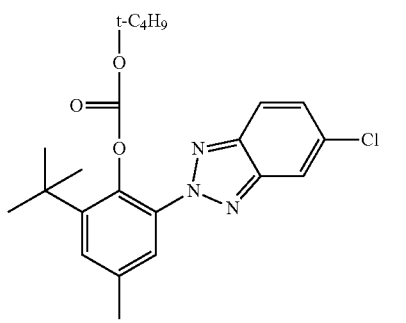
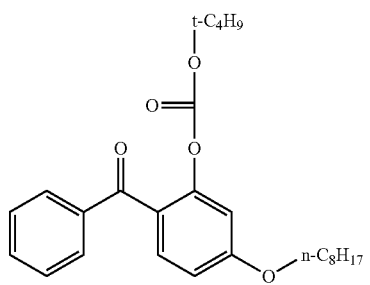

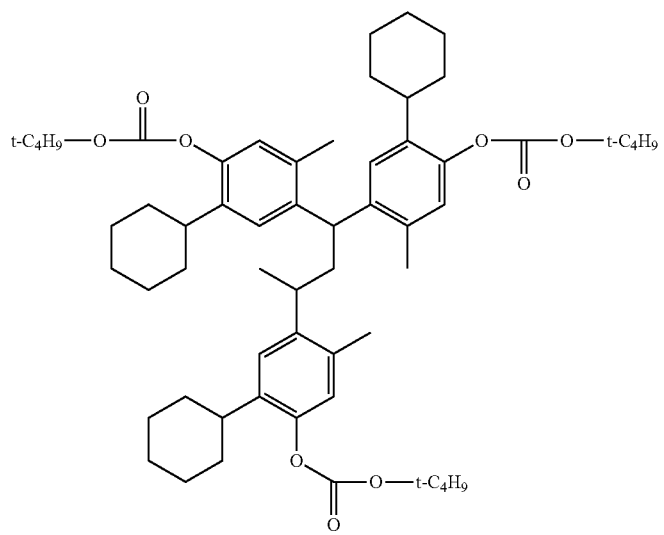
[Chem. 49]
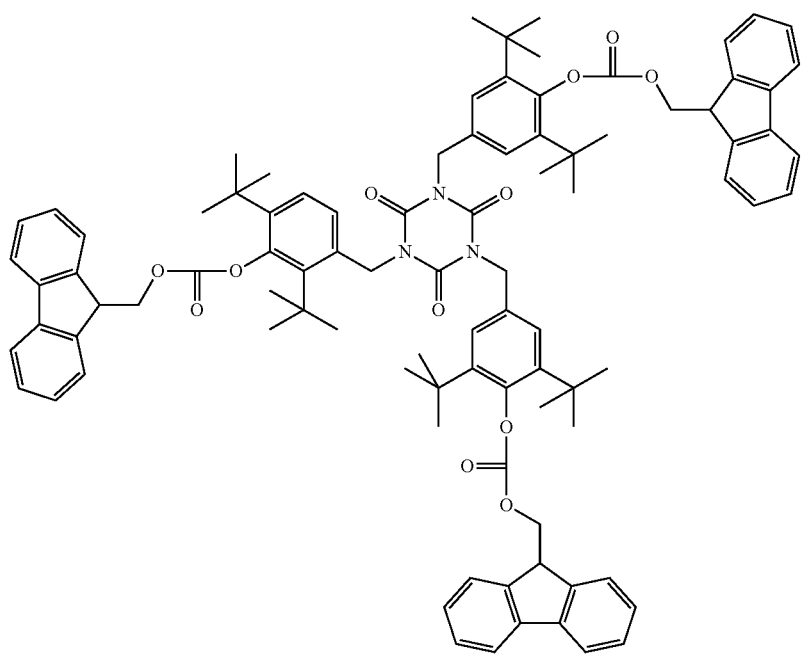

59
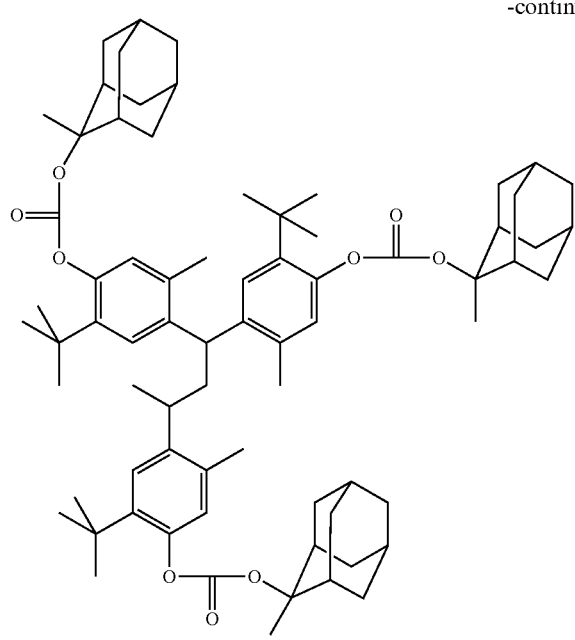
60
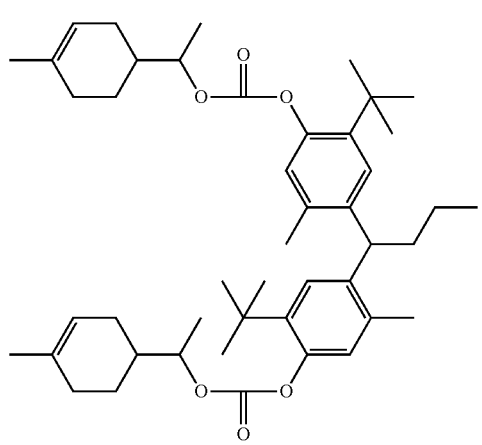
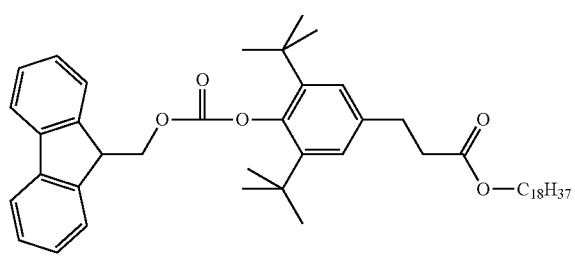
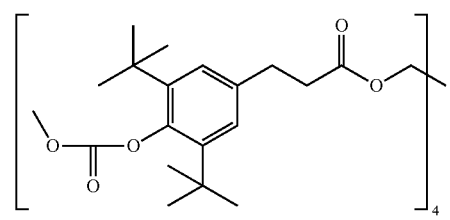
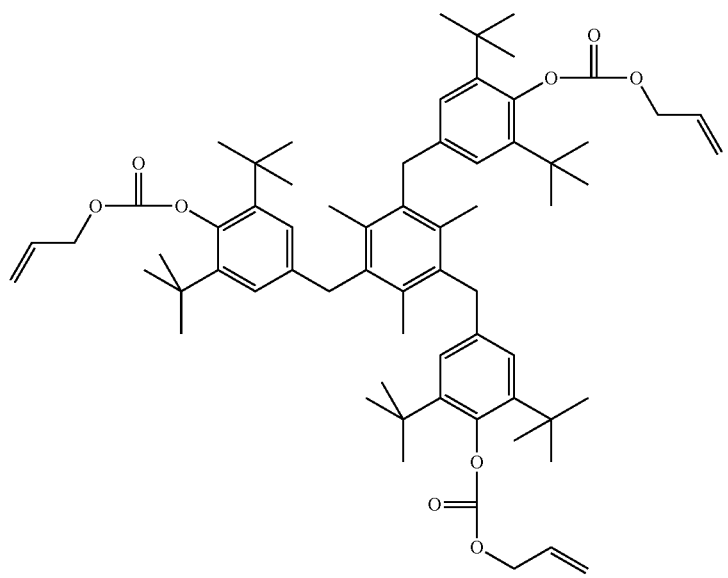

[Chem. 50]
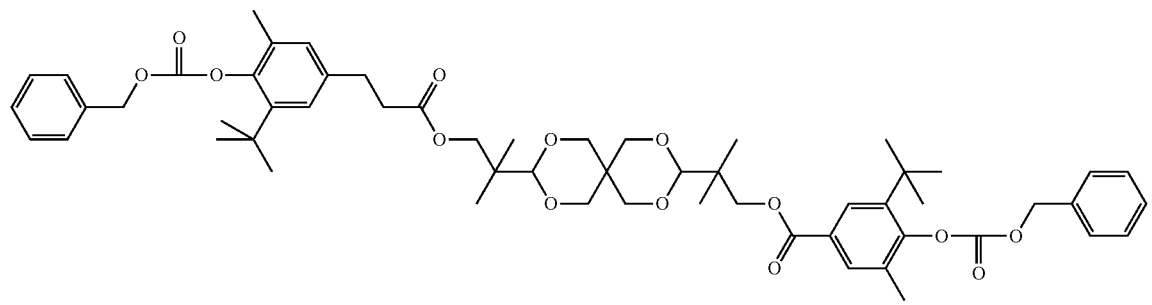
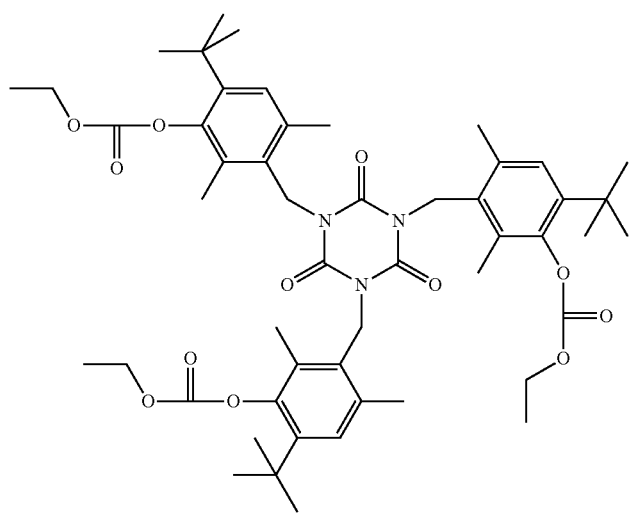
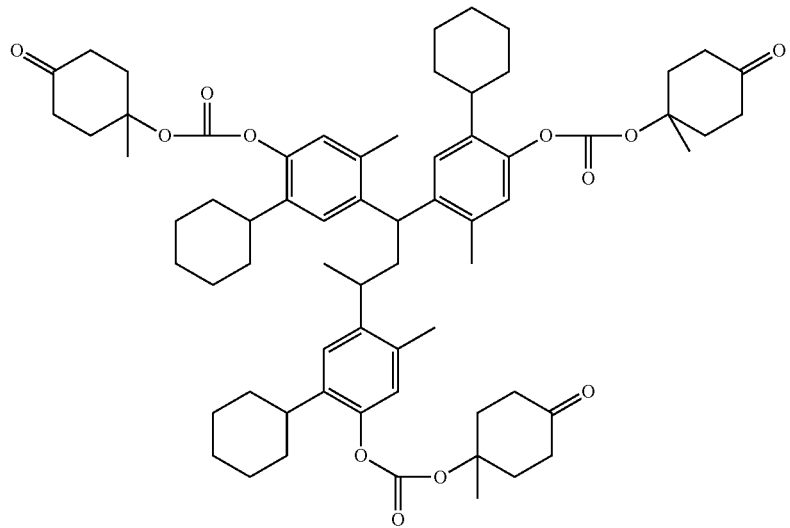

[Chem. 51]
-continued
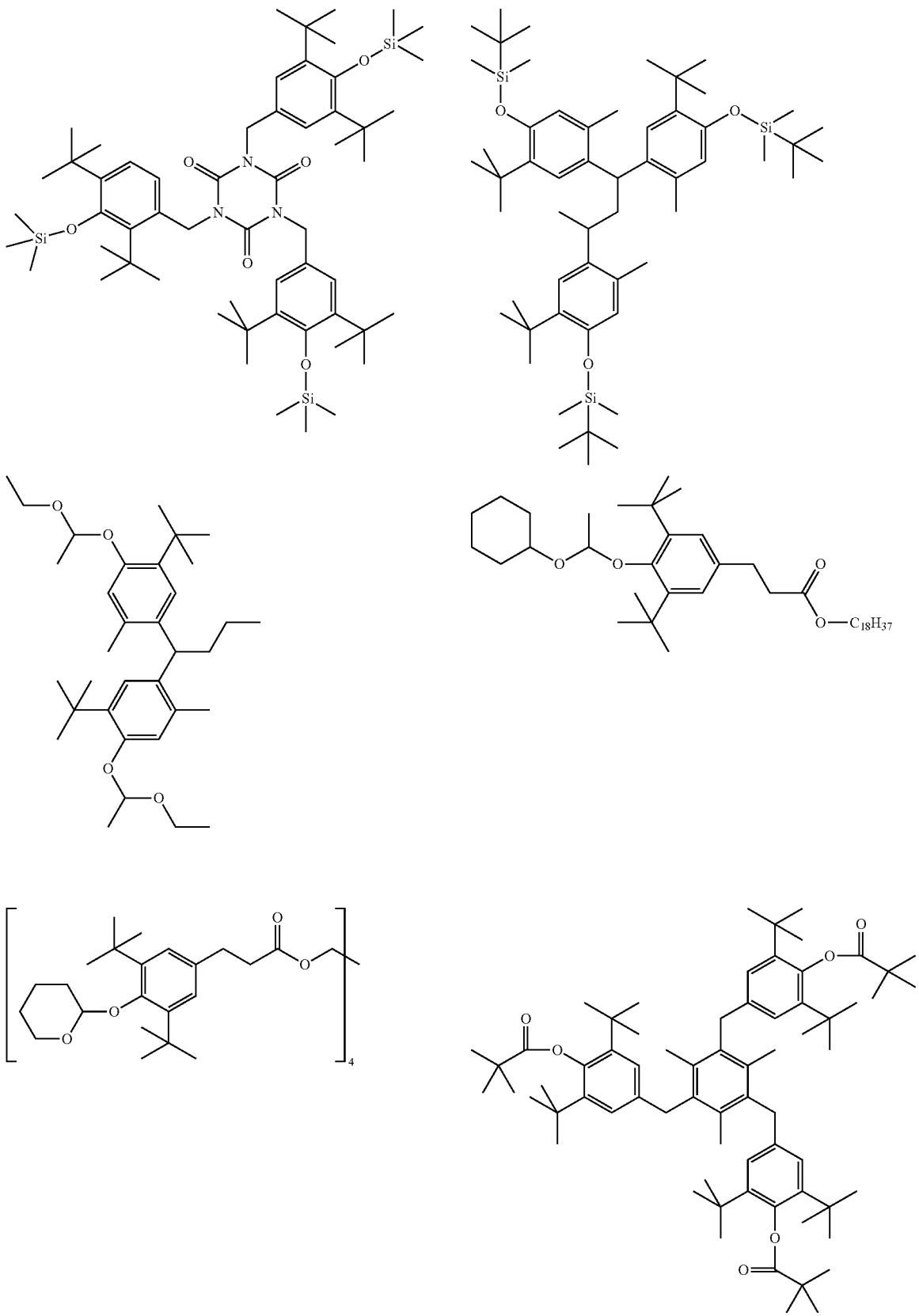

[Chem. 52]
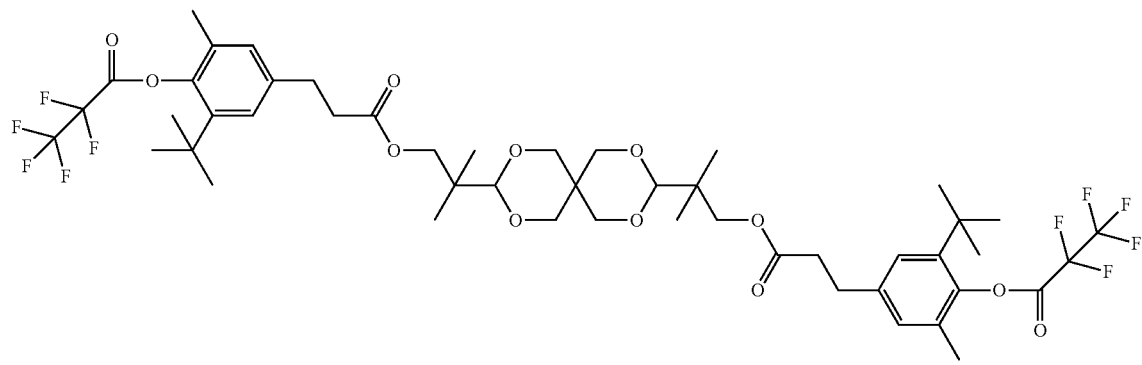
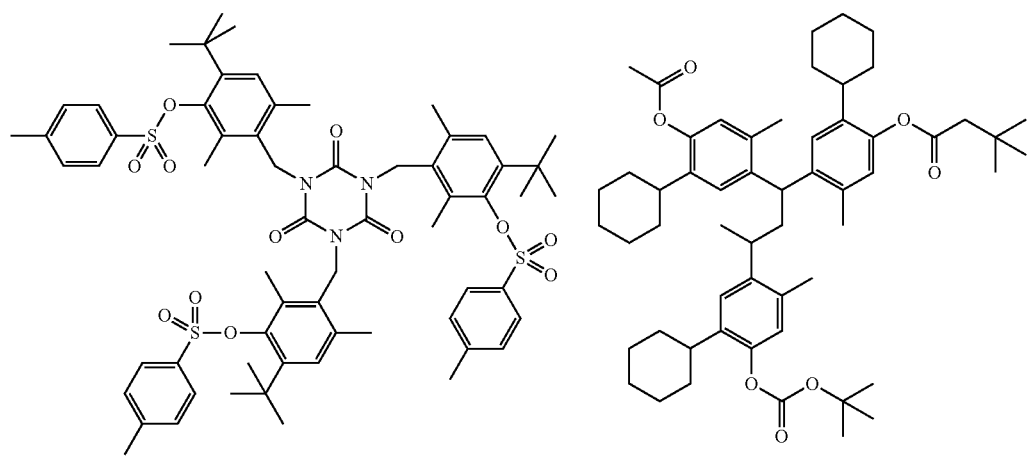
[Chem. 53]
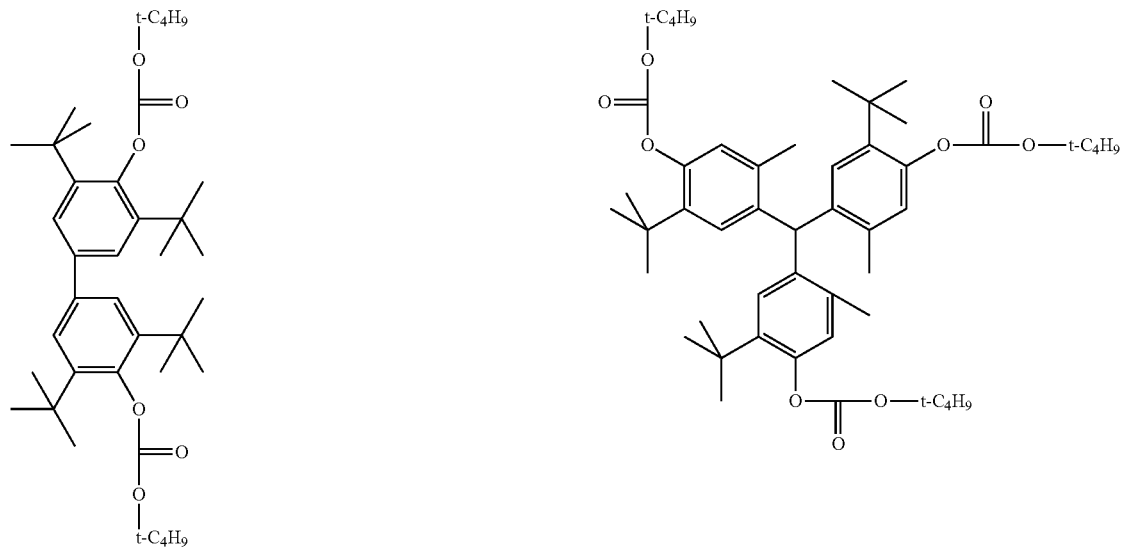

-continued
67
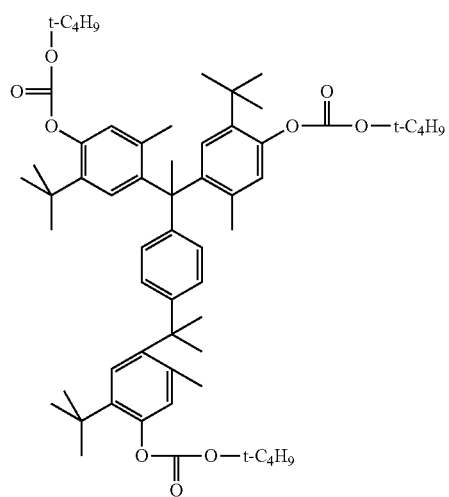
68
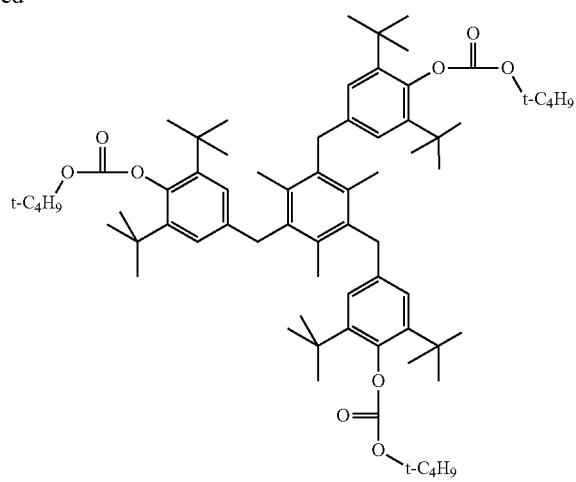
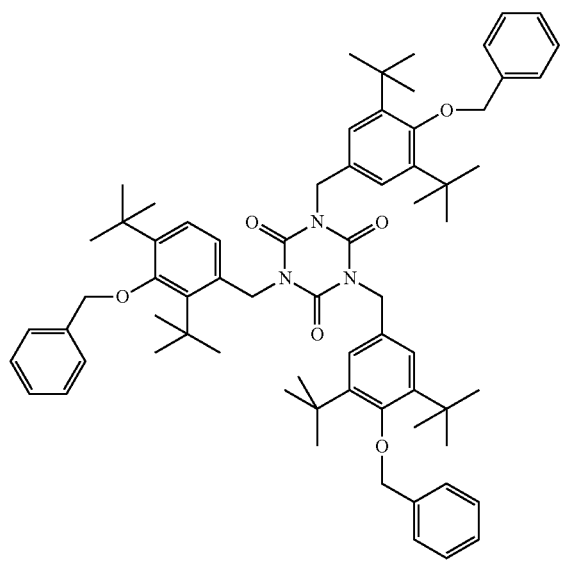
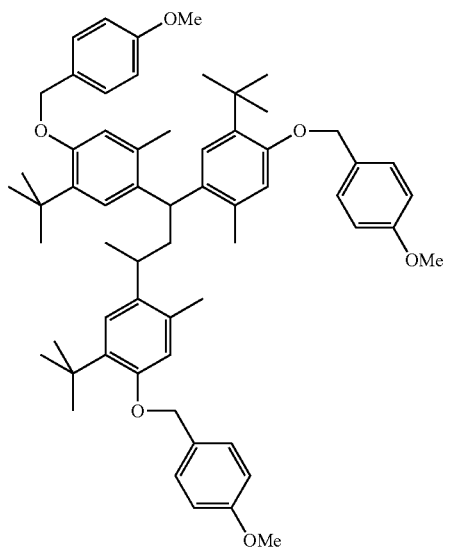
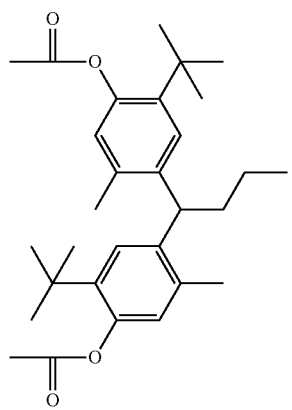 [SMILES: CCCC(c1cc(C(C)(C)C)c(OC(C)=O)cc1C)c1cc(C(C)(C)C)c(OC(C)=O)cc1C]

[Chem. 54]
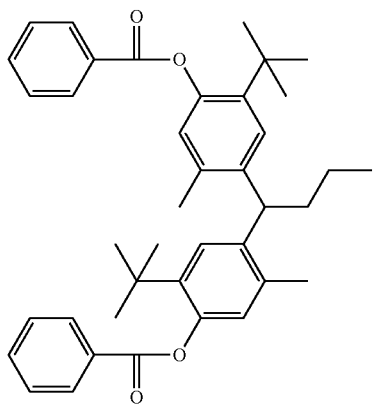
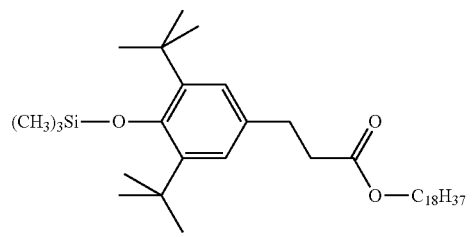
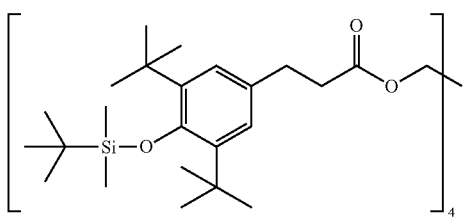
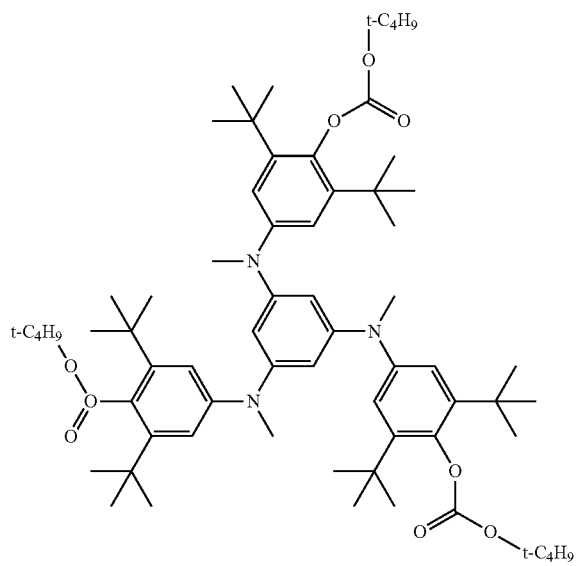
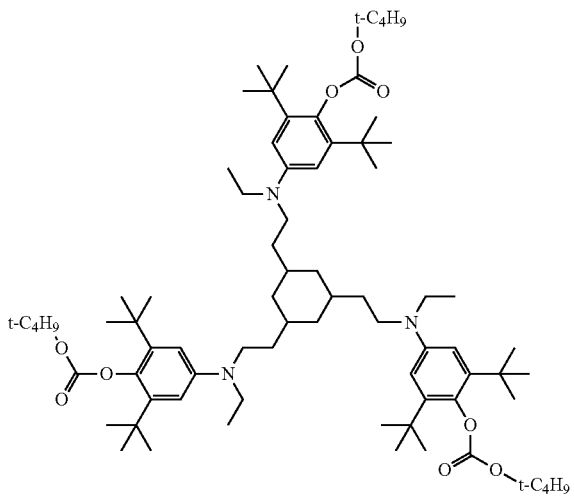
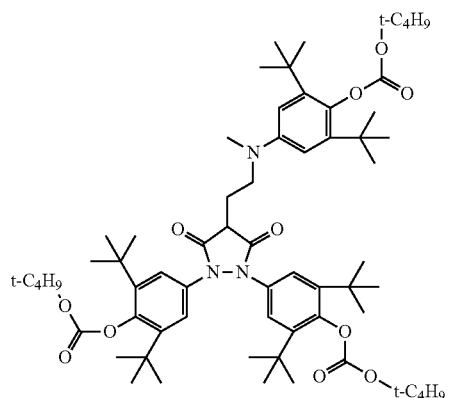

[Chem. 55]
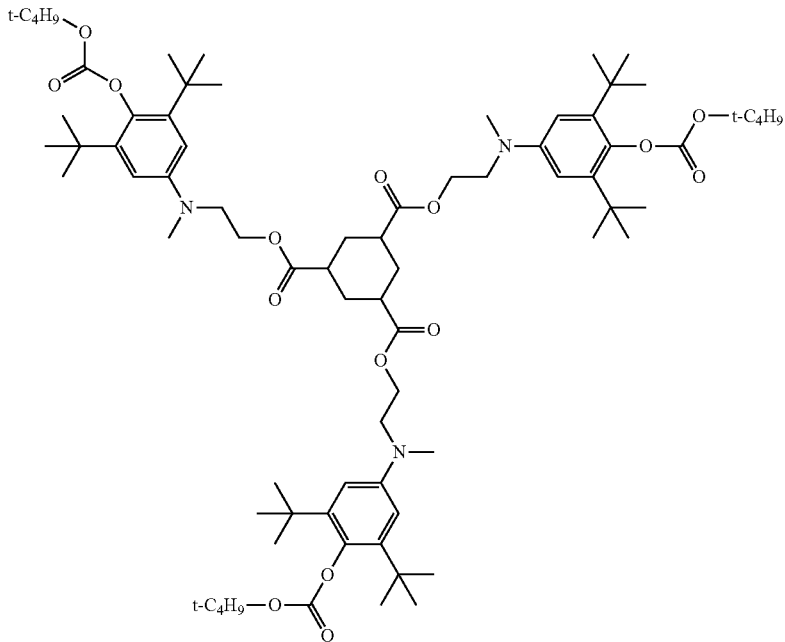
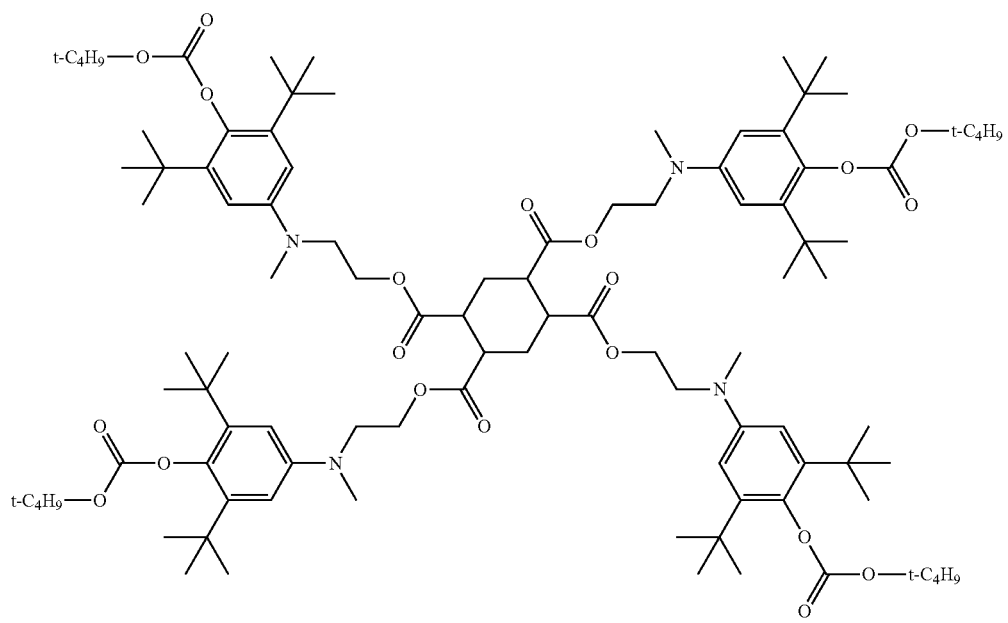

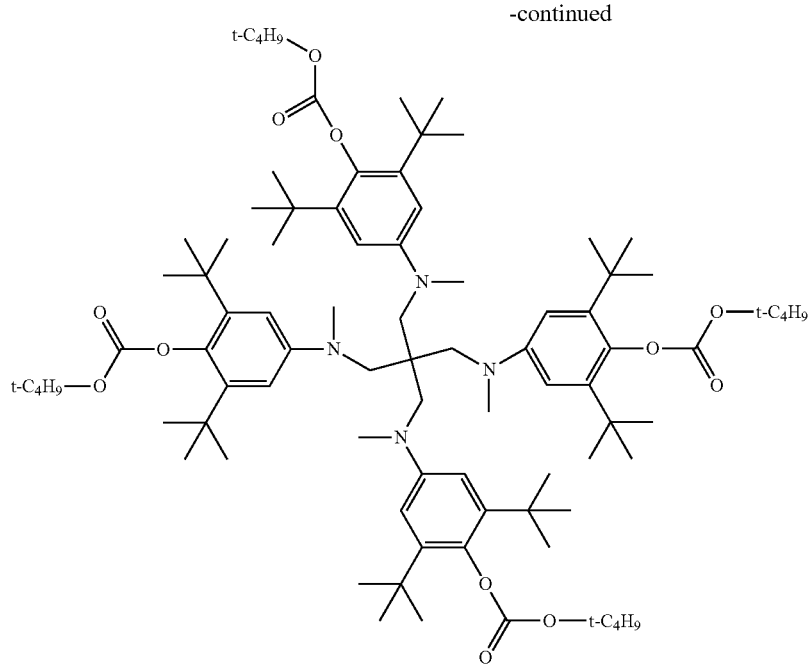
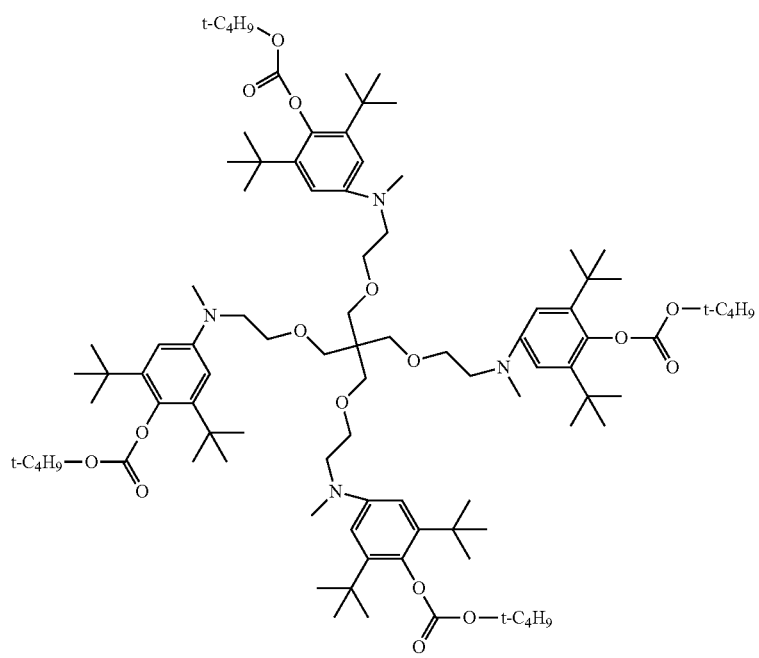

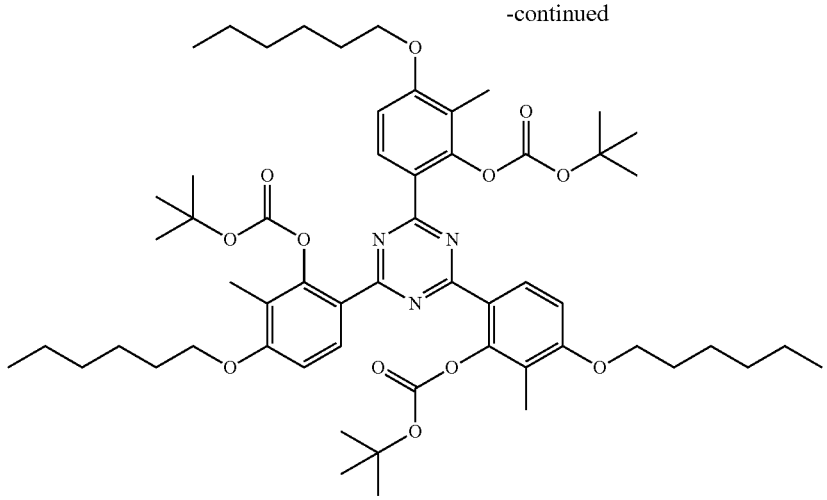

The process for preparing the compound of general formula (1) is not particularly limited. For example, the compound may be obtained by the reaction between a phenolic compound prepared by the processes described in JP 57-111375A, JP 3-173843A, JP 6-128195A, JP 7-206771A, JP 7-252191A, and JP 2004-501128A and an acid anhydride, an acid chloride, a Boc reagent, an alkyl halide compound, a silyl chloride compound, an allyl ether compound, and so forth.

The composition containing the latent additive of the invention will then be described.

The latent additive of the invention is useful as a latent antioxidant or a latent UV absorber in photocuring compositions, thermosetting compositions, photosensitive compositions, or polymerizable compositions. It is also useful as a latent color developer in heat-sensitive materials.

The content of the latent additive of the invention in a photocuring composition is preferably 0.001 to 20 mass %, more preferably 0.005 to 5 mass %.

The content of the latent additive of the invention in a thermosetting composition is preferably 0.001 to 20 mass %, more preferably 0.005 to 5 mass %.

The content of the latent additive of the invention in a photosensitive composition is preferably 0.001 to 20 mass %, more preferably 0.005 to 5 mass %.

The content of the latent additive of the invention in a polymerizable composition is preferably 0.001 to 20 mass %, more preferably 0.005 to 5 mass %.

The photocuring composition cures upon being irradiated with light, which may be any of photo-cationic curing type, photo-anionic curing type, and photo-radical curing type. Application of the latent additive to a photo-radical curing composition is particularly beneficial because the latent additive does not hinder the progress of polymerization reaction by trapping radicals generated from the photo radical polymerization initiator during irradiation and, after being activated by heating, traps oxidatively or otherwise generated radicals.

The photo-radical curing composition essentially contains a radical polymerizable organic substance and a photo-radical polymerization initiator as well as the latent additive of the invention as a latent antioxidant.

The radical polymerizable organic substance is a compound that polymerizes or crosslinks on being irradiated with light in the presence of the photo-radical polymerization initiator, preferably a compound having at least one unsaturated double bond per molecule, such as acrylate compounds, methacrylate compounds, allylurethane compounds, unsaturated polyester compounds, styrene compounds, radical-polymerizable group-modified silicone oils, and vinyl compounds.

Of the radical polymerizable organic substances those having a (meth)acryl group are preferred for ease of synthesis, ready availability, and ease of handling. Examples of such compounds are epoxy (meth)acrylates, urethane (meth)acrylates, polyester (meth)acrylates, polyether (meth)acrylates, and alcohol (meth)acrylic acid esters.

The epoxy (meth)acrylates are obtained by, for example, the reaction between (meth)acrylic acid and a known aromatic, alicyclic, or aliphatic epoxy resin. Particularly preferred of them are (meth)acrylates of aromatic epoxy resins, i.e., (meth)acrylates obtained by the reaction between (meth)acrylic acid and a polyglycidyl ether of a polyphenol having at least one aromatic nucleus or an alkylene oxide adduct thereof, such as obtained by causing bisphenol A or an alkylene oxide adduct thereof to react with epichlorohydrin and causing the resulting glycidyl ether to react with (meth)acrylic acid or obtained by the reaction between an epoxy novolak resin and (meth)acrylic acid.

Preferred examples of the urethane (meth)acrylates include those obtained by causing one or more hydroxyl-containing polyesters or polyethers to react with a hydroxyl-containing (meth)acrylic ester and an isocyanate and those obtained by the reaction between a hydroxyl-containing (meth)acrylic ester and an isocyanate.

Preferred examples of the hydroxyl-containing polyesters include those obtained by the reaction between one or more aliphatic polyalcohols and one or more polybasic acids. Examples of the aliphatic polyalcohols are 1,3-butanediol, 1,4-butanediol, 1,6-hexanediol, diethylene glycol, triethylene glycol, neopentyl glycol, polyethylene glycol, polypropylene glycol, trimethylolpropane, glycerol, pentaerythritol, and dipentaerythritol. Examples of the polybasic acids are adipic acid, terephthalic acid, phthalic anhydride, and trimellitic acid.

Preferred examples of the hydroxyl-containing polyethers include those obtained by adding one or more alkylene oxides to an aliphatic polyalcohol. Examples of the aliphatic polyalcohol are the same as described above. Examples of the alkylene oxide are ethylene oxide and propylene oxide.

Preferred examples of the hydroxyl-containing (meth) acrylic ester include those obtained by esterification between an aliphatic polyalcohol and (meth)acrylic acid. Examples of the aliphatic polyalcohol are the same as described above. Those obtained by esterification of an aliphatic dihydric alcohol with (meth)acrylic acid, such as 2-hydroxyethyl (meth)acrylate, are particularly preferred.

Preferred examples of the isocyanate are compounds having one or more isocyanate groups per molecule. More preferred are diisocyanate compounds, such as tolylene diisocyanate, hexamethylene diisocyanate, and isophorone diisocyanate.

The polyester (meth)acrylates are preferably those obtained by the reaction of a hydroxyl-containing polyester with (meth)acrylic acid. The hydroxyl-containing polyester is preferably those obtained by esterification reaction between one or more aliphatic polyalcohols and one or more of monobasic acids, polybasic acids, and phenols. Examples of the aliphatic polyalcohols are the same as those recited above. Examples of the monobasic acids include formic acid, acetic acid, butylcarboxylic acid, and benzoic acid. Examples of the polybasic acids include adipic acid, terephthalic acid, phthalic anhydride, and trimellitic acid. Examples of the phenols include phenol, p-nonylphenol, and bisphenol A.

The polyether (meth)acrylates are preferably those obtained by the reaction between a hydroxyl-containing polyether and meth(acrylic acid). The hydroxyl-containing polyether used here is preferably a product obtained by adding one or more alkylene oxides to an aliphatic polyalcohol. Examples of the aliphatic polyalcohol are the same as described above. Examples of the alkylene oxide are ethylene oxide and propylene oxide.

The alcohol (meth)acrylic acid esters are preferably (meth)acrylates obtained by the reaction between an aromatic or aliphatic alcohol having at least one hydroxyl group per molecule or an alkylene oxide adduct thereof and (meth)acrylic acid, including 2-ethylhexyl (meth)acrylate, 2-hydroxyethyl (meth)acrylate, 2-hydroxypropyl (meth) acrylate, isoamyl (meth)acrylate, lauryl (meth)acrylate, stearyl (meth)acrylate, isooctyl (meth)acrylate, tetrahydrofurfuryl (meth)acrylate, isobornyl (meth)acrylate, benzyl (meth)acrylate, 1,3-butanediol di(meth)acrylate, 1,4-butanediol di(meth)acrylate, 1,6-hexanediol di(meth)acrylate, diethylene glycol di(meth)acrylate, triethylene glycol di(meth)acrylate, neopentyl glycol di(meth)acrylate, polyethylene glycol di(meth)acrylate, polypropylene glycol di(meth)acrylate, trimethylolpropane tri(meth)acrylate, pentaerythritol tetra(meth)acrylate, dipentaerythritol hexa(meth)acrylate, and ε-caprolactone-modified dipentaerythritol hexa(meth) acrylate. Preferred of these (meth)acrylates are polyalcohol poly(meth)acrylates.

The above described radical polymerizable organic substances are commercially available. Examples of commercially available monofunctional compounds include Aronix M-101, M-102, M-111, M-113, M-117, M-152, and TO-1210 (all from ToaGosei Co., Ltd.); KAYARAD TC-110S, R-564, and R-128 (all from Nippon Kayaku Co., Ltd.); and Viscoat 192, Viscoat 220, Viscoat 2311HP, Viscoat 2000, Viscoat 2100, Viscoat 2150, Viscoat 8F, and Viscoat 17F (all from Osaka Organic Chemical Industry Ltd.).

Examples of commercially available polyfunctional compounds include SA1002 (from Mitsubishi Chemical Corp.); Viscoat 195, Viscoat 230, Viscoat 260, Viscoat 215. Viscoat 310. Viscoat 214HP. Viscoat 295, Viscoat 300, Viscoat 360, Viscoat GPT, Viscoat 400, Viscoat 700, Viscoat 540, Viscoat 3000, and Viscoat 3700 (all from Osaka Organic Chemical Industry Ltd.); KAYARAD R-526, HDDA, NPGDA, TPGDA, MANDA, R-551, R-712, R-604, R-684, PET-30, GPO-303, TMPTA, THE-330. DPHA, DPHA-2H. DPHA-2C, DPHA-21, D-310, D-330, DPCA-20, DPCA-30, DPCA-60, DPCA-120, DN-0075, DN-2475, EB-645, EB-648, and EB-3700 (all from Daicel-UCB Co., Ltd.); T-1420, T-2020, T-2040, TPA-320, TPA-330, RP-1040, RP-2040, R-011, R-300, and R-205 (all from Nippon Kayaku Co., Ltd.); Aronix M-210, M-220, M-233, M-240, M-215, M-305, M-309, M-310, M-315, M-325, M-400, M-408, M-450, M-6200, and M-6400 (all from ToaGosei Co., Ltd.); Light Acrylate BP-4EA, BP-4PA, BP-2EA, BP-2PA, and DCP-A (all from Kyoeisha Co., Ltd.); New Frontier ASF-400 (from Nippon Steel & Sumikin Chemical Co., Ltd.); Ripoxy SP-1506, SP-1507, SP-1509, VR-77, SP-4010, and SP-4060 (all from Showa High Polymer Co., Ltd.); and NK Ester A-BPE-4 (from Shin-Nakamura Chemical Co., Ltd.).

These radical polymerizable organic substances may be used either alone or in combination of two or more thereof in accordance with desired performance. It is preferred that at least 50 mass % of the radical polymerizable organic substance be at least one compound having a (meth)acryl group per molecule.

The photo-radical polymerization initiator may be any compound capable of initiating radical polymerization upon irradiation with light. Suitable photo-radical polymerization initiators include ketone compounds, such as acetophenone compounds, benzyl compounds, benzophenone compounds, and thioxanthone compounds; and oxime compounds.

Examples of the acetophenone compounds include diethoxyacetophenone, 2-hydroxy-2-methyl-1-phenylpropan-1-one, 4'-isopropyl-2-hydroxy-2-methylpropiophenone, 2-hydroxymethyl-2-methylpropiophenone, 2,2-dimethoxy-1,2-diphenylethan-1-one, p-dimethylaminoacetophenone, p-tert-butyldichloroacetophenone, p-tert-butyltrichloroacetophenone, p-azidobenzalacetophenone, 1-hydroxycyclohexylphenyl ketone, 2-methyl-1-[4-(methylthio)phenyl]-2-morpholinopropanone-1,2-benzyl-2-dimethylamino-1-(4-morpholinophenyl)-butanone-1, benzoin, benzoin methyl ether, benzoin ethyl ether, benzoin isopropyl ether, benzoin n-butyl ether, benzoin isobutyl ether and 1-[4-(2-hydroxyethoxy)phenyl]-2-hydroxy-2-methyl-1-propan-1-one.

Examples of the benzyl compounds are benzil and anisil.

Examples of the benzophenone compounds include benzophenone, methyl o-benzoylbenzoate. Michler's ketone, 4,4'-bisdiethylaminobenzophenone, 4,4-dichlorobenzophenone, and 4-benzoyl-4'-methyldiphenyl sulfide.

Examples of the oxime compounds include:
2-octanedione, 1-[4-(phenylthio)-, 2-(O-benzoyloxime)], ethanone, 1-[9-ethyl-6-(2-methylbenzoyl)-9H-carbazol-3-yl]-, 1-(O-acetyloxime), methanone, (2-methylphenyl) [6-nitro-9-[3-(trimethylsilyl)propyl]-9H-carbazol-3-yl]-, 1-(O-acetyloxime),
methanone, (9-ethyl-6-nitro-9H-carbazol-3-yl)(2-methylphenyl), O-acetyloxime, methanone, (9-ethyl-6-nitro-9H-carbazol-3-yl)[2-methyl-4-(4-morpholinyl)phenyl, O-acetyloxime,
methanone, (3,5-dinitrophenyl)(9-ethyl-6-nitro-9H-carbazol-3-yl)(2-methylphenyl) O-acetyloxime, methanone, (9-ethyl-6-nitro-9H-carbazol-3-yl)(3-nitrophenyl). O-acetyloxime,
1,3,5-triazine-2,4,6(1H,3H,5H)-trione, 3,5-tris[2-(acetyloxy)-3-[3-[(1E)-1-[(acetyloxy)iminoethyl]-6-nitro-9H-carbazol-9-yl]propyl]-, 1,2-butanedione, 1-[4-(phenylthio)phenyl]-, 2-(O-acetyloxime),
1,2-butanediondione, 1-[4-[[4-(2-hydroxyethoxyl)phenyl]thio]phenyl]-, 2-(O-acetyloxime), 1,2-butanedione, 1,1'-(thiodi-4,1-phenylene)bis-, 2,2-bis(O-acetyloxime), and 1,2-octanedione, 1-[4-(phenylthio)phenyl]-2-[O-(4-methylbenzoyl)oxime].

Examples of the thioxanthone compounds include thioxanthone, 2-methylthioxanthone, 2-ethylthioxanthone, 2-chlorothioxanthone, 2-isopropylthioxanthone, and 2,4-diethylthioxanthone.

Other useful photo-radical polymerization initiators include 2,4,6-trimethylbenzoyl diphenylphosphine oxide, bis(cyclopentadienyl)-bis[26-difluoro-3-(pyrryl-1-yl)]titanium.

These photo-radical polymerization initiators may be used alone or in combination of two or more thereof according to the desired performance.

The photo-radical polymerization initiator is used in a stoichiometrically required amount with respect to the radical polymerizable organic substance, preferably 0.05 to 10 parts, more preferably 0.1 to 10 parts, by mass relative to the radical polymerizable organic substance. Amounts more than that range can result in a failure to obtain a cured product with sufficient strength. In amounts less than the range, the resin can fail to cure sufficiently.

The thermosetting composition cures upon heating, which may be any of thermal cationic curing type, thermal anionic curing type, and thermal radical curing type. Application of the latent additive to a thermal radical curing composition is particularly beneficial because the latent antioxidant traps radicals after being activated by heating.

The thermal radical curing composition essentially contains the above described radical polymerizable organic substance and a thermal radical polymerization initiator as well as the latent additive of the invention as a latent antioxidant.

Examples of the thermal radical polymerization initiator include azo initiators, such as 2,2'-azobisisobutyronitrile, 2,2'-azobis(methyl isobutyrate), 2,2'-azobis-2,4-dimethylvaleronitrile, and 1,1'-azobis(1-acetoxy-1-phenylethane); peroxide initiators, such as benzoyl peroxide, di-t-butylbenzoyl peroxide, t-butylperoxy pivalate, and di(4-t-butylcyclohexyl) peroxydicarbonate; and persulfates, such as ammonium persulfate, sodium persulfate, and potassium persulfate. They may be used either individually or in combination of two or more thereof.

The thermosetting composition is applied either as such or, where needed, as dissolved or dispersed in an organic solvent onto a substrate made, e.g., of soda-lime glass, quartz glass, semiconductor, metal, paper, or plastic by a known method, such as spin coating, roll coating, bar coating, die coating, curtain coating, printing, or dipping, followed by heating to cure.

Any known organic solvent may be used to dissolve or disperse the thermosetting composition. Ketones, ethers, amides, and alcohols are preferred solvents. Specific examples include acetone, methyl ethyl ketone, methyl n-butyl ketone, methyl isobutyl ketone, ethyl isobutyl ketone, diethyl ether, tetrahydrofuran, dioxane, dimethylformamide, diethylformamide, dimethylacetamide, diethylacetamide, N-methylpyrrolidone, methanol, ethanol isopropyl alcohol, ethylene glycol, propylene glycol, 2-methoxy-2-propanol, and tetraglyme.

The heating for cure is carried out usually at higher than about 60° C., preferably at about 100° to 300° C., for about 10 seconds to 3 hours.

The above described polymerizable compositions are subjected to chemical reaction to cause the radical polymerizable organic substance to homo- or copolymerize by suspension, continuous, solution, emulsion, bulk, or other polymerization processes, if necessary in an organic solvent.

The photosensitive composition changes in properties on irradiation with light. Upon undergoing chemical reaction, the photosensitive composition becomes soluble (positive resist type) or insoluble (negative resist type). The photosensitive composition essentially contains a compound having an ethylenically unsaturated double bond (hereinafter referred to as an ethylenically unsaturated polymerizable compound) and having an acid value and a photo-radical polymerization initiator as well as the latent additive of the invention as a latent antioxidant. Examples of the ethylenically unsaturated polymerizable compound having an acid value include (meth)acrylic acid, α-chloroacrylic acid, itaconic acid, maleic acid, citraconic acid, fumaric acid, Hymic acid (5-norbornene-2,3-dicarboxylic acid), crotonic acid, isocrotonic acid, vinylacetic acid, allylacetic acid, cinnamic acid, sorbic acid, mesaconic acid, mono[2-(meth)acryloyloxyethyl]succinate, mono[2-(meth)acryloyloxyethyl]phthalate, a mono(meth)acrylate of a polymer having a carboxyl group and a hydroxyl group at both terminals, such as ω-carboxypolycaprolactone mono(meth)acrylate, hydroxyethyl (meth)acrylate malate, hydroxypropyl (meth)acrylate malate, dicyclopentadiene malate, and a polyfunctional (meth)acrylate having one carboxyl group and two or more (meth)acryloyl groups; vinyl alcohols, such as allyl alcohol and crotyl alcohol; novolak epoxy compounds, such as phenol and/or cresol novolak epoxy resins, novolak epoxy resins having a biphenyl or naphthalene structure, bisphenol A novolak epoxy compounds, and dicyclopentadiene novolak epoxy compounds; polyphenylmethane epoxy resins having two or more epoxy groups; resins obtained by causing an epoxy resin, such as an epoxy compound represented by general formula (I) below, and an unsaturated monobasic acid to react with each other and causing the resulting reaction product to react with a polybasic acid anhydride; and polymers of a polyfunctional acrylate having an acid value obtained by the reaction between a hydroxyl-containing polyfunctional acrylate (e.g., pentaerythritol triacrylate or dipentaerythritol pentaacrylate) and a dibasic acid anhydride (e.g., succinic anhydride, phthalic anhydride, or tetrahydrophthalic anhydride).

[Chem. 56]

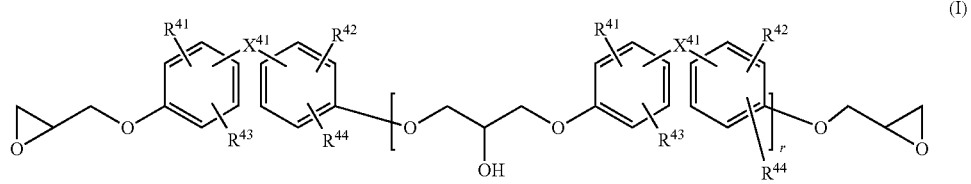

(I)

wherein $X^{41}$ represents a single bond, a methylene group, an optionally halogen-substituted C1-C4 alkylidene group, a C3-C20 alicyclic hydrocarbon group, —O—, —S—, —SO$_2$—, —SS—, —SO—, —CO—, —OCO—, or a substituent represented by [Chem. 7] to [Chem. 9] recited above; $R^{41}$, $R^{42}$, $R^{43}$, and $R^{44}$ each independently represent a hydrogen atom, a C1-C5 alkyl group, a C1-C8 alkoxy group, a C2-C5 alkenyl group, or a halogen atom, the alkyl, alkoxy, and alkenyl group being optionally substituted with halogen; and r represents an integer of 0 to 10.

These polymerizable compounds may be used either individually or in combination of two or more thereof. They may be used in combination with an ethylenically unsaturated polymerizable compound having no acid value. In the case when two or more polymerizable compounds are used in combination, they may previously be copolymerized and used as a copolymer.

Examples of the ethylenically unsaturated polymerizable compound having no acid value include esters between an unsaturated monobasic acid and a polyhydric alcohol or a polyhydric phenol, such as 2-hydroxyethyl (meth)acrylate, 2-hydroxypropyl (meth)acrylate, glycidyl (meth)acrylate, compound Nos. A1 through A4 shown below, methyl (meth)acrylate, butyl (meth)acrylate, isobutyl (meth)acrylate, t-butyl (meth)acrylate, cyclohexyl (meth)acrylate, n-octyl (meth)acrylate, isooctyl (meth)acrylate, isononyl (meth)acrylate, stearyl (meth)acrylate, lauryl (meth)acrylate, methoxyethyl (meth)acrylate, dimethylaminomethyl (meth)acrylate, dimethylaminoethyl (meth)acrylate, aminopropyl (meth)acrylate, dimethylaminopropyl (meth)acrylate, ethoxyethyl (meth)acrylate, poly(ethoxy)ethyl (meth)acrylate, butoxyethoxyethyl (meth)acrylate, ethylhexyl (meth)acrylate, phenoxyethyl (meth)acrylate, tetrahydrofuryl (meth)acrylate, vinyl (meth)acrylate, allyl (meth)acrylate, benzyl (meth)acrylate, ethylene glycol di(meth)acrylate, diethylene glycol di(meth)acrylate, triethylene glycol di(meth)acrylate, polyethylene glycol di(meth)acrylate, propylene glycol di(meth)acrylate, 1,4-butanediol di(meth)acrylate, 1,6-hexanediol di(meth)acrylate, trimethylolethane tri(meth)acrylate, trimethylolpropane tri(meth)acrylate, dipentaerythritol penta(meth)acrylate, dipentaerythritol hexa(meth)acrylate, pentaerythritol tetra(meth)acrylate, pentaerythritol tri(meth)acrylate, tricyclodecanedimethylol di(meth)acrylate, tri[(meth)acryloylethyl]isocyanurate, and polyester(meth)acrylate oligomers; metal salts of unsaturated polybasic acids, such as zinc(meth)acrylate and magnesium(meth)acrylate; unsaturated polybasic acid anhydrides, such as maleic anhydride, itaconic anhydride, citraconic anhydride, methyltetrahydrophthalic anhydride, tetrahydrophthalic anhydride, trialkyltetrahydrophthalic anhydrides, 5-(2,5-dioxotetrahydrofuryl)-3-methyl-3-cyclohexene-1,2-dicarboxylic acid anhydride, trialkyltetrahydrophthalic anhydride-maleic anhydride adducts, dodecenylsuccinic anhydride, and methylhymic anhydride; amides formed between an unsaturated monobasic acid and a polyfunctional amine, such as (meth)acrylamide, methylenebis(meth)acrylamide, diethylenetiaminetris(meth)acrylamide, xylylenebis(meth)acrylamide, α-chloroacrylamide, and N-2-hydroxyethyl(meth)acrylamide; unsaturated aldehydes, such as acrolein; unsaturated nitriles, such as (meth)acrylonitrile, α-chloroacrylonitrile, vinylidene cyanide, and allyl cyanide; unsaturated aromatic compounds, such as styrene, 4-methylstyrene, 4-ethylstyrene, 4-methoxystyrene, 4-hydroxystyrene, 4-chlorostyrene, divinylbenzene, vinyltoluene, vinylbenzoic acid, vinylphenol, vinylsulfonic acid, 4-vinylbenzenesulfonic acid, vinylbenzyl methyl ether, and vinylbenzyl glycidyl ether; unsaturated ketones, such as methyl vinyl ketone; unsaturated amine compounds, such as vinylamine, allylamine, N-vinylpyrrolidone, and vinylpiperidine; vinyl ethers, such as vinyl methyl ether, vinyl ethyl ether, n-butyl vinyl ether, isobutyl vinyl ether, and allyl glycidyl ether; unsaturated imides, such as maleimide, N-phenyhnaleimide, and N-cyclohexylmaleimide; indenes, such as indene and 1-methylindene; aliphatic conjugated dienes, such as 1,3-butadiene, isoprene, and chloroprene; macromonomers having a mono(meth)acryloyl group at the terminal of a polymeric molecular chain, such as polystyrene, polymethyl (meth)acrylate, poly-n-butyl(meth)acrylate, and polysiloxanes; other vinyl compounds, such as (meth)acrylonitrile, ethylene, propylene, butylene, vinyl chloride, and vinyl acetate; macromonomers, such as polymethyl methacrylate macromonomers and polystyrene macromonomers; monomethacrylates having a tricyclodecane structure; copolymers comprising N-phenyhnaleimide, metacryloyloxymethyl-3-ethyloxetane or the like and (meth)acrylic acid and reaction products obtained by causing these (meth)acrylic acid copolymers to react with an isocyanate compound having an unsaturated bond, such as KARENZ MOI and AOI available from Showa Denko K. K.; vinyl chloride, vinylidene chloride, divinyl succinate, diallyl phthalate, triallyl phosphate, triallyl isocyanurate, vinyl thioether, vinylimidazole, vinyloxazoline, vinylcarbazole, vinylpyrrolidone, vinylpyridine; vinyhuethane compounds formed between a hydroxyl-containing vinyl monomer and a polyisocyanate compound; vinylepoxy compounds formed between a hydroxyl-containing vinyl monomer and a polyepoxy compound; and reaction products formed between a hydroxyl-containing polyfunctional acrylate, such as pentaerythritol triacrylate or dipentaerythritol pentaacrylate, and a polyfunctional isocyanate, such as tolylene diisocyanate or hexamethylene diisocyanate.

[Chem. 57]

Compound No. A1

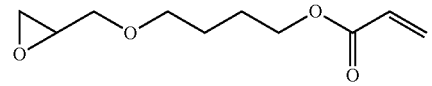

[Chem. 58]

Compound No. A2

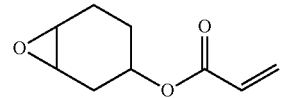

[Chem. 59]

Compound No. A3

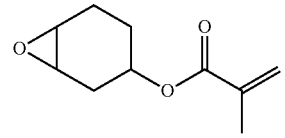

[Chem. 60]

Compound No. A4

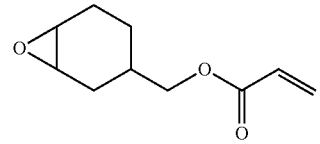

In order to improve developability of the photosensitive resin composition through acid value adjustment, a mono- or polyfunctional epoxy compound may be used in combination with the ethylenically unsaturated polymerizable compound having an acid value. It is preferred that the solid content of the ethylenically unsaturated polymerizable compound having an acid value to have an acid value of 5 to 120 mg-KOH/g. The amount of the mono- or polyfunctional epoxy compound to be used is preferably decided so as to satisfy the above recited range of acid value.

Examples of the monofunctional epoxy compound include glycidyl methacrylate, methyl glycidyl ether, ethyl glycidyl ether, propyl glycidyl ether, isopropyl glycidyl ether, butyl glycidyl ether, isobutyl glycidyl ether, t-butyl glycidyl ether, pentyl glycidyl ether, hexyl glycidyl ether, heptyl glycidyl ether, octyl glycidyl ether, nonyl glycidyl ether, decyl glycidyl ether, undecyl glycidyl ether, dodecyl glycidyl ether, tridecyl glycidyl ether, tetradecyl glycidyl ether, pentadecyl glycidyl ether, hexadecyl glycidyl ether, 2-ethylhexyl glycidyl ether, allyl glycidyl ether, propargyl glycidyl ether, p-methoxyethyl glycidyl ether, phenyl glycidyl ether, p-methoxyglycidyl ether, p-butylphenyl glycidyl ether, cresyl glycidyl ether, 2-methylcresyl glycidyl ether, 4-nonylphenyl glycidyl ether, benzyl glycidyl ether, p-cumylphenyl glycidyl ether, trityl glycidyl ether, 2,3-epoxypropyl methacrylate, epoxidized soybean oil, epoxidized linseed oil, glycidyl butyrate, vinylcyclohexene monoxide, 1,2-epoxy-4-vinylcyclohexane, styrene oxide, pinene oxide, methylstyrene oxide, cyclohexene oxide, and propylene oxide.

The polyfunctional epoxy compound is preferably at least one compound selected from the group consisting of bisphenol epoxy compounds and glycidyl ethers. Using at least one of them is effective in providing a (colored) alkali developable photosensitive resin composition having further improved characteristics. Examples of the bisphenol epoxy compounds include the epoxy compounds represented by general formula (1) supra and others, including bisphenol epoxy compounds such as hydrogenated bisphenol epoxy compounds. Examples of the glycidyl ethers include ethylene glycol diglycidyl ether, propylene glycol diglycidyl ether, 1,4-butanediol diglycidyl ether, 1,6-hexanediol diglycidyl ether, 1,8-octanediol diglycidyl ether, 1,10-decanediol diglycidyl ether, 2,2-dimethyl-1,3-propanediol diglycidyl ether, diethylene glycol diglycidyl ether, triethylene glycol diglycidyl ether, tetraethylene glycol diglycidyl ether, hexaethylene glycol diglycidyl ether, 1,4-cyclohexanedimethanol diglycidyl ether, 1,1,1-tri(glycidyloxymethyl)propane, 1,1,1-tri(glycidyloxymethyl)ethane 1,1,1-tri(glycidyloxymethyl)methane, and 1,1,1-tetra(glycidyloxymethyl)methane.

Other useful polyfunctional epoxy compounds include novolak epoxy compounds, such as phenol novolak epoxy compounds, biphenyl novolak epoxy compounds, cresol novolak epoxy compounds, bisphenol A novolak epoxy compounds, and dicyclopentadiene novolak epoxy compounds; alicyclic epoxy compounds, such as 3,4-epoxy-6-methylcyclohexylmethyl 3,4-epoxy-6-methylcyclohexanecarboxylate, 3,4-epoxycyclohexylmethyl 3,4-epoxycyclohexanecarboxylate, and 1-epoxyethyl-3,4-epoxycyclohexane; glycidyl esters, such as diglycidyl phthalate, diglycidyl tetrahydrophthalate, and glycidyl dimerate; glycidylamines, such as tetraglycidyl diaminodiphenylmethane, triglycidyl p-aminophenol, and N,N-diglycidylaniline; heterocyclic epoxy compounds, such as 1,3-diglycidyl-5,5-dimethylhydantoin and triglycidyl isocyanurate; dioxide compounds, such as dicyclopentadiene dioxide; naphthalene epoxy compounds, triphenylmethane epoxy compounds, and dicyclopentadiene epoxy compounds.

The photosensitive composition may further contain a colorant to be formulated into a colored photosensitive composition. A cured product of the colored photosensitive composition is suited for use as a color filter.

The amount of the colorant in the colored photosensitive composition is preferably 0.01 to 50 mass %, more preferably 0.1 to 30 mass %.

The colorant may be a dye or a pigment.

The dye to be used is not particularly limited as long as it has an absorption in the wavelength range of from 380 to 1200 nm. Examples of the dye include azo dyes, anthraquinone dyes, indigoid dyes, triarylmethane dyes, xanthene dyes, alizarine dyes, acridine dyes, stilbene dyes, thiazole dyes, naphthol dyes, quinoline dyes, nitro dyes, indamine dyes, oxazine dyes, phthalocyanine dyes, cyanine dyes, diimmonium compounds, cyanoethenyl compounds, dicyanostyrene compounds, rhodamine compounds, perylene compounds, polyenenaphtholactam compounds, coumarin compounds, squarylium compounds, croconium compounds, spiropyran compounds, spirooxazine compounds, merocyanine compounds, oxonol compounds, styryl compounds, pyrylium compounds, rhodanine compounds, oxazolone compounds, phthalimide compounds, cinnoline compounds, naphthoquinone compounds, azaanthraquinone compounds, porphyrine compounds, azaporphyrine compounds, pyrromethene compounds, quinacridone compounds, diketopyrrolopyrrole compounds, indigo compounds, acridine compounds, azine compounds, azomethine compounds, aniline compounds, quinacridone compounds, quinophthalone compounds, quinoneimine compounds, iridium complex compounds, and europium complex compounds. These dyes may be used as a mixture thereof.

The pigments may be either organic or inorganic, including nitroso compounds, nitro compounds, azo compounds, diazo compounds, xanthene compounds, quinoline compounds, anthraquinone compounds, coumarin compounds, phthalocyanine compounds, isoindolinone compounds, isoindoline compounds, quinacridone compounds, anthanthrone compounds, perynone compounds, perylene compounds, diketopyrrolopyrrole compounds, thioindigo compounds, dioxazine compounds, triphenylmethane compounds, quinophthalone compounds, and naphthalenetetracarboxylic acids; metal complex compounds, such as azo dyes and cyanine dyes; lake pigments, carbon black species, such as furnace black, channel black, thermal black, acetylene black, Ketjen black, and lamp black; the carbon blacks recited which are coated with an epoxy resin, the carbon blacks recited which are dispersed in a solvent together with a resin to have 20 to 200 mg/g of the resin adsorbed thereon, the carbon blacks recited which are surface treated with an acid or an alkali; the carbon blacks recited which have an average particle size of 8 nm or greater and a DBP absorption of 90 ml/100 g or less, the carbon blacks recited which have total oxygen amount, which is calculated from CO and $CO_2$ in the volatile matter content at 950° C.; graphite, graphitized carbon black, activated carbon, carbon fiber, carbon nanotube, carbon microcoil, carbon nanohorn, carbon aerogel, fullerene; aniline black, pigment black 7, titanium black; hydrophobic resins, chromium oxide green, Milori blue, cobalt green, cobalt blue, manganese compounds, ferrocyanides, phosphate ultramarine blue, Prussian blue, ultramarine, cerulean blue, viridian, emerald green, lead sulfate, lead yellow, zinc yellow, rouge (red iron (III) oxide), cadmium red, synthetic iron black, and amber. The pigments may be used either individually or as a mixture thereof.

Commercially available pigments may be used as the organic pigments or the inorganic pigments. Examples of them include pigment red 1, 2, 3, 9, 10, 14, 17, 22, 23, 31, 38, 41, 48, 49, 88, 90, 97, 112, 119, 122, 123, 144, 149, 166, 168, 169, 170, 171, 177, 179, 180, 184, 185, 192, 200, 202, 209, 215, 216, 217, 220, 223, 224, 226, 227, 228, 240, and 254; pigment orange 13, 31, 34, 36, 38, 43, 46, 48, 49, 51, 52, 55, 59, 60, 61, 62, 64, 65, and 71; pigment yellow 1, 3, 12, 13, 14, 16, 17, 20, 24, 55, 60, 73, 81, 83, 86, 93, 95, 97, 98, 100, 109, 110, 113, 114, 117, 120, 125, 126, 127, 129, 137, 138, 139, 147, 148, 150, 151, 152, 153, 154, 166, 168, 175, 180, and 185; pigment green 7, 10, and 36; pigment blue 15, 15:1, 15:2, 15:3, 15:4, 15:5, 15:6, 22, 24, 56, 60, 61, 62, and 64; and pigment violet 1, 19, 23, 27, 29, 30, 32, 37, 40, and 50.

The colored photosensitive composition may optionally contain a solvent. Usually, solvents capable of dissolving or dispersing the above described components are used where necessary. Such solvents include ketones, e.g., methyl ethyl ketone, methyl amyl ketone, diethyl ketone, acetone, methyl isopropyl ketone, methyl isobutyl ketone, cyclohexanone, and 2-heptanone; ethers, such as ethyl ether, dioxane, tetrahydrofuran, 1,2-dimethoxyethane, 1,2-diethoxyethane, and dipropylene glycol dimethyl ether; esters, such as methyl acetate, ethyl acetate, n-propyl acetate, isopropyl acetate, n-butyl acetate, cyclohexyl acetate, ethyl lactate, dimethyl succinate, and Texanol; cellosolve solvents, such as ethylene glycol monomethyl ether and ethylene glycol monoethyl ether; alcohols, such as methanol, ethanol, isopropyl alcohol, n-propanol, isobutanol, n-butanol, and amyl alcohol; ether esters, such as ethylene glycol monomethyl acetate, ethylene glycol monoethyl acetate, propylene glycol 1-monomethyl ether 2-acetate (PGMEA), dipropylene glycol monomethyl ether acetate, 3-methoxybutyl acetate, and ethoxyethyl propionate; BTX solvents (benzene, toluene, xylene, etc.); aliphatic hydrocarbons, such as hexane, heptane, octane, and cyclohexane; terpene hydrocarbon oils, such as turpentine oil, D-limonene, and pinene; paraffinic solvents, such as mineral spirit. Swazol #310 (available from Cosmo Matsuyama Oil Co., ltd.), and Solvesso #100 (available from Exxon Chemical); halogenated aliphatic hydrocarbons, such as carbon tetrachloride, chloroform, trichloroethylene, methylene chloride, and 1,2-dichloroethane; halogenated aromatic hydrocarbons, such as chlorobenzene; carbitol solvents; aniline, triethylamine, pyridine, acetic acid, acetonitrile, carbon disulfide, N,N-dimethylformamide, N,N-dimethylacetamide, N-methylpyrrolidone, dimethyl sulfoxide, and water. These solvents may be used either individually or as a mixture of two or more thereof. Preferred of them are ketones and ether esters, particularly propylene glycol 1-monomethyl ether 2-acetate, cyclohexanone, and so on in view of providing good compatibility between a resist and a photopolymerization initiator in the photosensitive composition.

The colored photosensitive composition may further contain an inorganic compound. Examples of the inorganic compound include metal oxides, such as nickel oxide, iron oxide, iridium oxide, titanium oxide, zinc oxide, magnesium oxide, calcium oxide, potassium oxide, silica, and alumina; layered clay minerals, Milori blue, calcium carbonate, magnesium carbonate, cobalt compounds, manganese compounds, glass powder, mica, talc, kaolin, ferrocyanides, various metal sulfates, sulfides, selenides, aluminum silicate, calcium silicate, aluminum hydroxide, platiman, gold, silver, and copper.

In the case when the pigment and/or inorganic compound is/are used in the colored composition, a dispersing agent can be added. Any dispersing agent may be used as long as it is capable of dispersing and stabilize the colorant and/or the inorganic compound, and commercially available dispersing agents, such as BYK series from BYK-Chemie GmbH, can be used. Particularly preferred are polymeric dispersing agents comprising a polyester, polyether, or polyurethane having a basic functional group and dispersing agents having a basic functional group containing a nitrogen atom, the functional group having a nitrogen atom being an amine and/or a quaternary salt thereof, and having an amine value of 1 to 100 mg-KOKHg.

If desired, the colored photosensitive resin composition may contain commonly employed additives, such as thermal polymerization suppressors, including anisole, hydroquinone, pyrocatechol, tert-butyl catechol, and phenothiazine; plasticizers; adhesion accelerators; fillers; defoaming agents; leveling agents; surface modifiers; antioxidants, including phenol antioxidants, phosphite antioxidants, and thioether antioxidants; UV absorbers; dispersing aids; anticoagulants; catalysts; effect enhancers; crosslinking agents; and thickeners.

The colored photosensitive composition may further contain other organic polymers in addition to the ethylenically unsaturated polymerizable compound having an acid value to provide a cured product with improved characteristics. Examples of the other organic polymer include polystyrene, polymethyl methacrylate, methyl methacrylate-ethyl acrylate copolymers, poly(meth)acrylic acid, styrene-(meth) acrylic acid copolymers, (meth)acrylic acid-methyl methacrylate copolymers, ethylene-vinyl chloride copolymers, ethylene-vinyl copolymers, polyvinyl chloride resins, ABS resins, nylon 6, nylon 66, nylon 12, urethane resins, polycarbonates, polyvinyl butyrals, cellulose esters, polyacrylamides, saturated polyesters, phenol resins, phenoxy resins, polyamide-imide resins, polyamic acid resins, and epoxy resins. Preferred of them are polystyrene, (meth)acrylic acid-methyl acrylate copolymers, and epoxy resins.

The colored photosensitive resin composition may furthermore contain a chain transfer agent, a sensitizer, a surfactant, a silane coupling agent, a melamine compound, and so forth.

As the chain transfer agent or the sensitizer, sulfur-containing compounds are generally used, including mercapto compounds, such as thioglycolic acid, thiomalic acid, thiosalicylic acid, 2-mercaptopropionic acid, 3-mercaptopropionic acid, 3-mercaptobutyric acid, N-(2-mercaptopropionyl)glycine, 2-mercaptonicotinic acid, 3-[N-(2-mercaptoethyl)cabamoyl]propionic acid, 3-[N-(2-mercaptoethyl) amino]propionic acid, N-(3-mercaptopropionyl)alanine, 2-mercaptoethanesulfonic acid, 3-mercaptopropanesulfonic acid, 4-mercaptobutanesulfonic acid, dodecyl (4-methylthio)phenyl ether, 2-mercaptoethanol, 3-mercapto-1,2-propanediol, 1-mercapto-2-propanol, 3-mercapto-2-butanol, mercaptophenol, 2-mercaptoethylamine, 2-mercaptoimidazole, 2-mercaptobenzimidazole, 2-mercapto-3-pyridinol, 2-mercaptobenzothiazole, mercaptoacetic acid, trimethylolpropane tris(3-mercaptopropionate), and pentaerythritol tetrakis(3-mercaptopropionate); disulfide compounds obtained by oxidizing the recited mercapto compounds; iodized alkyl compounds, such as iodoacetic acid, iodopropionic acid, 2-iodoethanol, 2-iodoethanesulfouic acid, and 3-iodopropanesulfonic acid, aliphatic polyfunctional thiol compounds, such as trimethylolpropane tris(3-mercaptoisobutyrate), butanediol bis(3-mercaptoisobutyrate), hexanedithiol, decanedithiol, 1,4-dimethylmercaptobenzene, butanediol bisthiopropionate, butanediol bisthioglycolate, ethylene glycol bisthioglycolate, trimethylolpropane tristhioglycolate, butanediol bisthiopropionate, trimethylolpropane tristhiopropionate, trimethylolpropane tristhioglycolate, pentaerythritol tetrakisthiopropionate, pentaerythritol tetrakisthioglycolate, trishydroxyethyl tristhiopropionate, compound C1 shown below, and trimercaptopropionic acid tris(2-hydroxyethyl)isocyanurate; KARENZ MT BDI, PE1 and NR1 Showa Denko.

[Chem. 61]

Compound C1

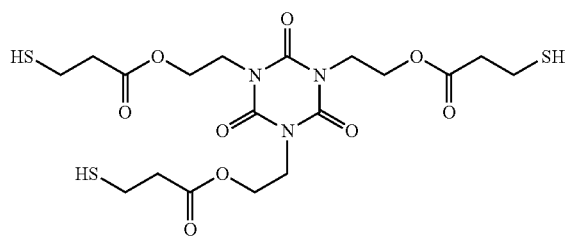

Examples of useful surfactants include fluorine surfactants, such as perfluoroalkyl phosphate esters and perfluoroalkyl carboxylates, anionic surfactants, such as higher aliphatic acid alkali salts, alkyl sulfonates, and alkyl sulfates, cationic surfactants, such as higher amine halogenates and quaternary ammonium salts, nonionic surfactants, such as polyethylene glycol alkyl ethers, polyethylene glycol fatty acid esters, sorbitan fatty acid esters, and fatty acid monoglycerides, amphoteric surfactants, and silicone surfactants. These surfactants may be used in combination.

Examples of useful silane coupling agents include those manufactured by Shin-Etsu Chemical Co., Ltd. Preferred among them are those having an isocyanate group, a methacryloyl group or an epoxy group, such as KBE-9007, KBM-502, and KBE-403.

Examples of useful melamine compounds include nitrogen-containing compounds having active methylol groups ($CH_2OH$) (e.g., (poly)methylolmelamnine, (poly)methylolglycoluril, (poly)methylolbenzoguanamine, and (poly)methylolurea) with all or a part (at least two) of their active methylol groups being etherified with one or more kinds of alkyl groups, including methyl, ethyl, and butyl. The remaining methylol group(s), if any, that are not alkyl-etherified may be condensed intramolecularly or intermolecularly to form an oligomeric component. Specific examples of such melamine compounds are hexamethoxymethylmelamine, hexabutoxymethylmelamine, tetramethoxymethylglycoluril, and tetrabutoxymethylglycoluril, with hexamethoxymethylmelamine and hexabutoxymethylmelamine being preferred.

The colored photosensitive composition can be applied to a supporting substrate, such as soda-lime glass, quartz glass, semiconductor substrates, metals, paper, or plastics, by known means, including spin coating, roll coating, bar coating, die coating, curtain coating, various printing techniques, and dipping. The colored photosensitive composition may be applied once to a carrier such as film and then transferred onto another substrate. The method for the application is not limited.

An active light source that emits light at a wavelength of 300 to 450 nm can be used to cure the colored photosensitive composition, including an ultrahigh pressure mercury lamp, a mercury vapor arc lamp, a carbon arc lamp, or a xenon arc lamp.

A laser direct-write process is beneficial in the interests of productivity, resolution, and pattern position accuracy, in which a laser beam as an exposure light source is directed to the photosensitive resin composition without using a mask to directly write an image based on digital information, e.g., from a computer. A laser beam having a wavelength of 340 to 430 nm is suitably used. Lasers emitting light of from the visible to infrared region are also usable, such as argon ion, helium-neon, YAG, and semiconductor lasers. When these lasers are used, a sensitizing dye that absorbs light of the visible to infrared region is added to the composition.

The colored photosensitive composition (or a cured product thereof) has unlimited application. It finds use in, for example, photocuring paints or varnishes; photocuring adhesives; printed boards; color filters for liquid crystal color displays, such as TV monitors, PC monitors, personal digital assistances, and digital cameras; color filters for CCD image sensors; electrode materials for plasma display panels; powder coatings; printing inks; printing plates, adhesives; compositions for dental use, resins for stereolithography; gel coats; photoresists for electronics; electroplating resists; etching resists; liquid or dry films; soldering resists; resists used in the manufacture of color filters of various displays or in the formation of structures of plasma display panels, electroluminescent displays, and LCDs; encapsulating compositions for electric/electronic components; solder resists; magnetic recording materials; fine machine parts; waveguides; optical switches; plating masks; etching masks; color test systems; glass fiber cable coatings; screen printing stencils; materials for making a three-dimensional object by stereolithography; holographic recording materials; image recording materials; fine electronic circuits; decolorizing materials; decolorizing materials for image recording materials; decolorizing materials for image recording materials using microcapsules; photoresist materials for printed wiring boards; photoresist materials for direct write using UV and visible lasers; and photoresist materials or protective layers used to form dielectric layers in the fabrication of multilayered printed circuit boards.

The colored photosensitive composition is useful in the formation of pixels of color filters, especially in the formation of color filters of image displays, such as LCD panels.

The color filter of displays is preferably formed by the steps of (1) forming a coating film of the colored photosensitive composition on a substrate, (2) irradiating the coating film with active light through a mask having a predetermined pattern, (3) developing the exposed coating film by a developer, and (4) heating the developed film. The colored photosensitive composition of the invention is also applicable to an inkjet printing method that involves no development in the color filter manufacturing.

Novel compounds provided by the present invention will then be described. Unless otherwise described, the description about the latent additive of the invention applies to the novel compounds.

The novel compounds according to the invention are represented by general formulae (2), (6), and (8) shown below, which are included in the latent additive compounds of the invention.

[Chem. 62]

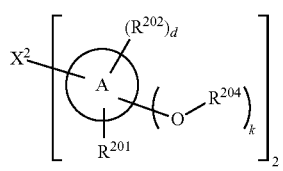

(2)

wherein A represents a 5- or 6-membered aromatic or heterocyclic ring;

$R^{201}$ and $R^{202}$ each independently represent a hydrogen atom, a halogen atom, a cyano group, a hydroxyl group, a nitro group, a carboxyl group, an optionally substituted C1-C40 alkyl group, a C6-C20 aryl group, a C7-C20 arylalkyl group, or a C2-C20 heterocyclic ring-containing group;

d represents an integer of 1 to 3;

k represents an integer of 1 to 3;

$R^{204}$ represents a C1-C20 alkyl group, a C2-C20 alkenyl group, a C6-C20 aryl group, a C7-C20 arylalkyl group, a C2-C20 heterocyclic ring-containing group, or a trialkylsilyl group;

the methylene moiety of the alkyl or arylalkyl group represented by $R^{201}$, $R^{202}$, and $R^{204}$ may be replaced by a combination of one or more groups selected from a carbon-carbon double bond, —O—, —S—, —CO—, —O—CO—, —CO—O—, —O—CO—O—, —O—CO—O—, —S—CO—, —CO—S—, —O—CO—S—, —S—CO—O—, —CO—NH—, —NH—CO—, —NH—CO—O—, —NR'—, >P=O, —S—S—, and —SO$_2$—; R' represents a hydrogen atom or a C1-C8 alkyl group;

a plurality of $R^{202}$'s may be taken together to form a benzene ring or a naphthalene ring;

a plurality of $R^{202}$'s may be the same or different; a plurality of $R^{204}$'s may be the same or different;

$X^2$ represents an oxygen atom, a sulfur atom, a group represented by [Chem. 63] shown below, >C=O, —NH—CO—, —CO—NH—, >NR$^{12}$, >PR$^{12}$, a substituent represented by group selected from general formula (3), general formula (4), or [Chem. 69] shown below; $R^{12}$ represents a hydrogen atom, an optionally substituted C1-C35 aliphatic hydrocarbon group, an optionally substituted C6-C35 aromatic ring-containing hydrocarbon group, or an optionally substituted C2-C35 heterocyclic ring-containing group, the aliphatic hydrocarbon group, aromatic ring-containing hydrocarbon group, and heterocyclic ring-containing group being optionally substituted by a combination of one or more groups selected from a carbon-carbon double bond, —O—, —S—, —CO—, —O—CO—, —CO—O—, —O—CO—O—, —S—CO—, —CO—S—, —O—CO—S—, —S—CO—O—, —CO—NH—, —NH—CO—, —NH—CO—O—, —NR'—, >P=O, —S—S—, and —SO$_2$—; the aromatic or heterocyclic ring may be fused to one or more additional rings; and $X^2$ may be taken together with A to form a ring.

[Chem. 63]

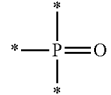

[Chem. 64]

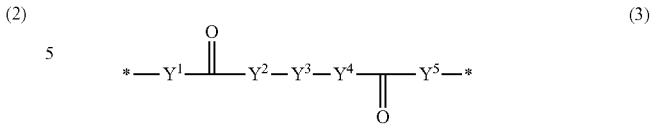

(3)

wherein $Y^1$ and $Y^5$ each independently represent a single bond, a C1-C4 alkylene group; $Y^2$ and $Y^4$ each independently represent an oxygen atom or —NR$^{13}$—; $R^{13}$ represents a hydrogen atom or a C1-C20 aliphatic hydrocarbon group; $Y^3$ represents a single bond, —NR$^{16}$—, a divalent C1-C35 aliphatic hydrocarbon group, a divalent C6-C35 aromatic ring-containing group, or a substituent represented by general formula (5) below, the aliphatic hydrocarbon group and C6-C35 aromatic ring-containing hydrocarbon group being optionally substituted by —COO—, —O—, —OCO—, —NHCO—, —NH—, or —CONH—; $R^{14}$ and $R^{15}$ each independently represent a hydrogen atom, a C1-C8 alkyl group, a C6-C20 aryl group, or a C7-C20 arylalkyl group; and $R^{16}$ represents a hydrogen atom, an optionally substituted C1-C35 aliphatic hydrocarbon group, an optionally substituted C6-C35 aromatic ring-containing hydrocarbon group, or an optionally substituted C2-C35 heterocyclic ring-containing group, the aliphatic hydrocarbon group, aromatic ring-containing hydrocarbon group, and heterocyclic ring-containing group being optionally substituted by a combination of one or more groups selected from a carbon-carbon double bond, —O—, —S—, —CO—, —O—CO—, —CO—, and —SO$_2$—.

[Chem. 65]

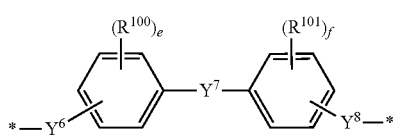

(4)

wherein $Y^6$ and $Y^8$ each independently represent —NR$^{17}$— or an optionally oxygen-interrupted C1-C4 alkylene group; $Y^7$ represents a single bond, —O—, —S—, —SO$_2$—, —CR$^{18}$R$^{19}$—, or any one of the substituents represented by [Chem. 66] to [Chem. 68] shown below; $R^{17}$ represents a hydrogen atom or a C1-C20 aliphatic hydrocarbon group; $R^{18}$ and $R^{19}$ each independently represent a hydrogen atom or an optionally substituted C1-C8 alkyl group; $R^{100}$ and $R^{101}$ each independently represent a hydrogen atom, a halogen atom, a cyano group, a hydroxyl group, a nitro group, a carboxyl group, a C1-C8 alkyl group, or a C1-C8 alkoxy group; e represents a number of 1 to 4; and f represents a number of 1 to 4.

[Chem. 66]

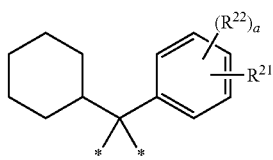

wherein $R^{21}$ represents a hydrogen atom, an optionally substituted phenyl group, or a C3-C10 cycloalkyl group; $R^{22}$ represents a C1-C10 alkyl group, a C1-C10 alkoxy group, a C2-C10 alkenyl group, or a halogen atom, the alkyl, alkoxy, or alkenyl group optionally having a substituent; and a represents an integer of 0 to 5.

[Chem. 67]

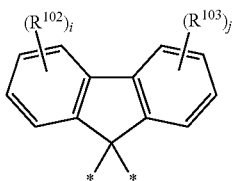

wherein $R^{102}$ and $R^{103}$ each independently represent a hydrogen atom, a halogen atom, a cyano group, a hydroxyl group, a nitro group, a carboxyl group, a C1-C8 alkyl group, or a C1-C8 alkoxy group; i represents a number of 1 to 4; and j represents a number of 1 to 4.

[Chem. 68]

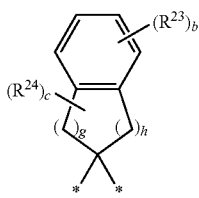

wherein $R^{23}$ and $R^{24}$ each independently represent an optionally substituted C1-C10 alkyl group, an optionally substituted C6-C20 aryl group, an optionally substituted C6-C20 aryloxy group, an optionally substituted C6-C20 arylthio group, an optionally substituted C6-C20 arylalkenyl group, an optionally substituted C7-C20 arylalkyl group, an optionally substituted C2-C20 heterocyclic ring-containing group, or a halogen atom, the methylene moiety of the alkyl and arylalkyl group being optionally replaced by an unsaturated bond, —O—, or —S—; adjacent $R^{23}$'s may be taken together to form a ring; b represents a number of 0 to 4; c represents a number of 0 to 8; and the sum of g and h is 2 to 4.

[Chem. 69]

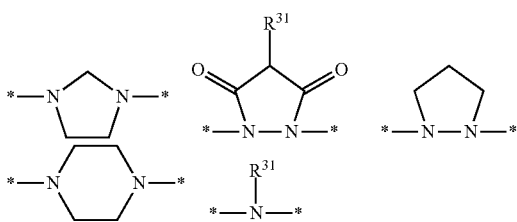

wherein $R^{31}$ represents a hydrogen atom, an optionally substituted C1-C35 aliphatic hydrocarbon group, an optionally substituted C6-C35 aromatic ring-containing hydrocarbon group, or an optionally substituted C2-C35 heterocyclic ring-containing group; the aliphatic hydrocarbon group being optionally substituted by a carbon-carbon double bond, —O—, —S—, —CO—, —O—CO—, —CO—O—, or —SO$_2$—.

[Chem. 70]

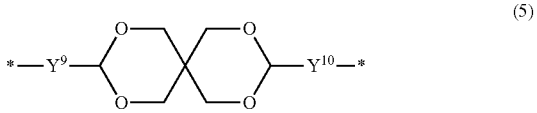

(5)

wherein $Y^9$ and $Y^{10}$ each independently represent a C1-C4 alkylene group.

[Chem. 71]

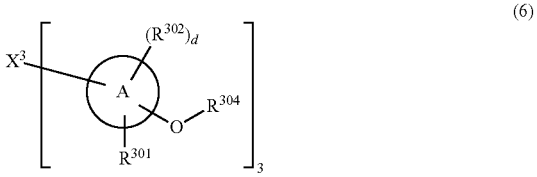

(6)

wherein A represents a 5- or 6-membered aromatic or heterocyclic ring;
$R^{301}$ and $R^{302}$ each independently represent a hydrogen atom, a halogen atom, a cyano group, a hydroxyl group, a nitro group, a carboxyl group, an optionally substituted C1-C40 alkyl group, a C6-C20 aryl group, a C7-C20 arylalkyl group, or a C2-C20 heterocyclic ring-containing group;
d represents an integer of 1 to 3;
k represents an integer of 1 to 3;
$R^{304}$ represents a C1-C20 alkyl group, a C2-C20 alkenyl group, a C6-C20 aryl group, a C7-C20 arylalkyl group, a C2-C20 heterocyclic ring-containing group, or a trialkylsilyl group;
the methylene moiety of the alkyl or arylalkyl group represented by $R^{301}$, $R^{302}$, and $R^{304}$ may be replaced by a combination of one or more groups selected from a carbon-carbon double bond, —O—, —S—, —CO—, —O—CO—, —CO—O—, —O—CO—O—, —O—CO—O—, —S—CO—, —CO—S—, —O—CO—S—, —S—CO—O—, —CO—NH—, —NH—CO—, —NH—CO—O—, —NR'—, >P=O, —S—S—, —SO$_2$—, and a nitrogen atom; R' represents a hydrogen atom or a C1-C8 alkyl group;
a plurality of $R^{302}$'s may be taken together to form a benzene ring or a naphthalene ring;
a plurality of $R^{302}$'s may be the same or different; a plurality of $R^{304}$'s may be the same or different; and
$X^3$ represents a substituent represented by general formula (7);
$X^3$ may optionally be taken together with A to form a ring; and the aromatic or heterocyclic ring may be fused to one or more additional rings.

[Chem. 72]

(7)

wherein $Y^{11}$ represents a trivalent C3-C35 aliphatic hydrocarbon group, a trivalent C3-C35 alicyclic hydrocarbon group, a trivalent C6-C35 aromatic ring-containing hydrocarbon group, or a trivalent C2-C35 heterocyclic ring-containing group; $Z^1$, $Z^2$, and $Z^3$ each independently represent a single bond, —O—, —S—, >CO, —CO—O—, —O—CO—, —SO$_2$—, —SS—, —SO—, >NR$^{32}$, >PR$^{32}$, an optionally substituted C1-C35 aliphatic hydrocarbon group, an optionally substituted C6-C35 aromatic ring-containing hydrocarbon group, or an optionally substituted C2-C35 heterocyclic ring-containing group; and R$^{32}$ represents a hydrogen atom, an optionally substituted C1-C35 aliphatic hydrocarbon group, an optionally substituted C6-C35 aromatic ring-containing hydrocarbon group, or an optionally substituted C2-C35 heterocyclic ring-containing group, the aliphatic hydrocarbon group being optionally substituted by a combination of one or more groups selected from a carbon-carbon double bond, —O—, —S—, —CO—, —O—CO—, —CO—O—, and —SO$_2$—.

[Chem. 73]

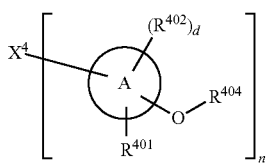

(8)

wherein A represents a 5- or 6-membered aromatic or heterocyclic ring:

R$^{401}$ and R$^{402}$ each independently represent a hydrogen atom, a halogen atom, a cyano group, a hydroxyl group, a nitro group, a carboxyl group, an optionally substituted C1-C40 alkyl group, a C6-C20 aryl group, a C7-C20 arylalkyl group, or a C2-C20 heterocyclic ring-containing group;

d represents an integer of 1 to 3;

k represents an integer of 1 to 3;

R$^{404}$ represents a C1-C20 alkyl group, a C2-C20 alkenyl group, a C6-C20 aryl group, a C7-C20 arylalkyl group, a C2-C20 heterocyclic ring-containing group, or a trialkylsilyl group;

the methylene moiety of the alkyl or arylalkyl group represented by R$^{401}$, R$^{402}$, and R$^{404}$ may be replaced by a combination of one or more groups selected from a carbon-carbon double bond, —O—, —S—, —CO—, —O—CO—, —CO—O—, —O—CO—O—, —O—CO—O—, —S—CO—, —CO—S—, —O—CO—S—, —S—CO—O—, —CO—NH—, —NH—CO—, —NH—CO—O—, —NR'—, >P=O, —S—S—, and —SO$_2$—; R' represents a hydrogen atom or a C1-C8 alkyl group; a plurality of R$^{402}$'s may be taken together to form a benzene ring or a naphthalene ring;

a plurality of R$^{402}$'s may be the same or different; a plurality of R$^{404}$'s may be the same or different;

n represents a number of 4 to 6;

X$^4$ represents a substituent represented by general formula (9) when n is 4, X$^4$ represents a substituent represented by general formula (10) when n is 5, or X$^4$ represents a substituent represented by general formula (11) when n is 6:

X$^4$ may optionally be taken together with A to form a ring; and the aromatic or heterocyclic ring may be fused to one or more additional rings.

[Chem. 74]

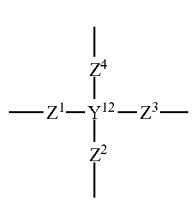

(9)

wherein Y$^{12}$ represents a carbon atom, a tetravalent C1-C35 aliphatic hydrocarbon group, a tetravalent C6-C35 aromatic ring-containing hydrocarbon group, or a tetravalent C2-C35 heterocyclic ring-containing group, the aliphatic hydrocarbon group being optionally substituted by a combination of one or more groups selected from —COO—, —O—, —OCO—, —NHCO—, —NH—, and —CONH—; and $Z^1$, $Z^2$, $Z^3$, and $Z^4$ each independently have the same meaning as $Z^1$ to $Z^3$ in general formula (7).

[Chem. 75]

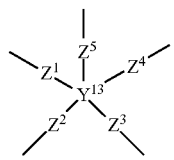

(10)

wherein Y$^{13}$ represent a pentavalent C2-C35 aliphatic hydrocarbon group, a pentavalent C6-C30 aromatic ring-containing hydrocarbon group, or a pentavalent C2-C30 heterocyclic ring-containing group, the aliphatic hydrocarbon group being optionally substituted by a combination of one or more groups selected from —COO—, —O—, —OCO—, —NHCO—, —NH—, and —CONH—; and $Z^1$, $Z^2$, $Z^3$, $Z^4$, and $Z^5$ each independently have the same meaning as $Z^1$ to $Z^3$ in general formula (7).

[Chem. 76]

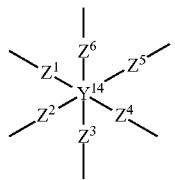

(11)

wherein Y$^{14}$ represents a hexavalent C2-C35 aliphatic hydrocarbon group, a hexavalent C6-C35 aromatic ring-containing hydrocarbon group, or a hexavalent C2-C35 heterocyclic ring-containing group, the aliphatic hydrocarbon group being optionally substituted by a combination of one or more groups selected from —COO—, —O—, —OCO—, —NHCO—, —NH—, and —CONH—; and $Z^1$, $Z^2$, $Z^3$, $Z^4$, $Z^5$, and $Z^6$ each independently have the same meaning as $Z^1$ to $Z^3$ in general formula (7).

EXAMPLES

The present invention will now be illustrated in greater detail with reference to Examples, but it should be understood that the invention is not limited thereto.

Preparation Example 1-1

Synthesis of Compound No. 1

0.01 mol of a phenol compound, 0.05 mol of di-tert-butyl dicarbonate, and 30 g of pyridine were mixed to obtain a mixture, and 0.025 mol of 4-dhnethylaminopyridine was added to the mixture at room temperature in a nitrogen atmosphere. The mixture was stirred at 60° C. for 3 hours. After cooling to room temperature, the reaction mixture was poured into 150 g of ion-exchanged water, and 200 g of chloroform was added thereto to carry out oil-water separation. The organic layer was dried over anhydrous sodium sulfate, and the solvent was removed by evaporation. The residue was crystallized from 100 g of methanol. The resulting white powder crystals were dried under reduced pressure at 60° C. for 3 hours to give a desired product. The resulting white powder crystals were identified to be the desired product by $^1$H-NMR and IR analyses. The melting point of the product was measured. The results obtained are shown in Tables 1 through 3 below.

[Chem. 77]

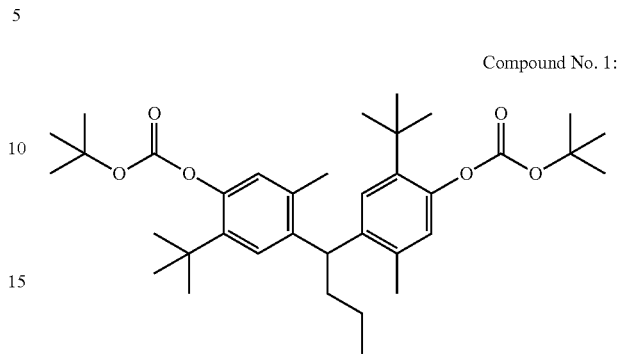

Compound No. 1:

Examples 1-1 to 1-9

Synthesis of Compound Nos. 2 to 10

Compound Nos. 2 to 11 shown below were synthesized in the same manner as in Preparation Example 1-1.

[Chem. 78]

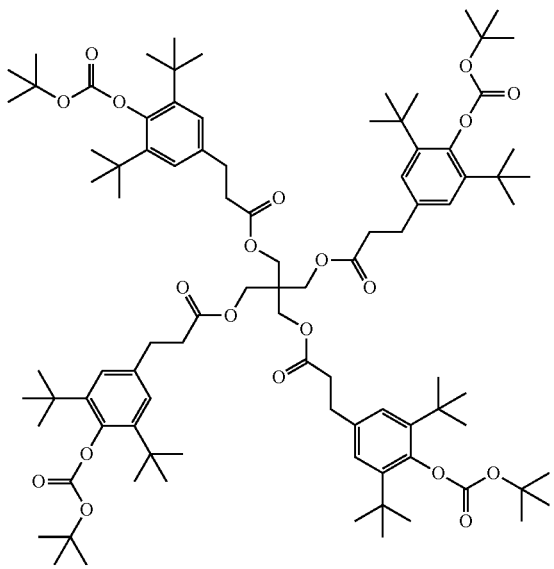

Compound No. 2

[Chem. 79]

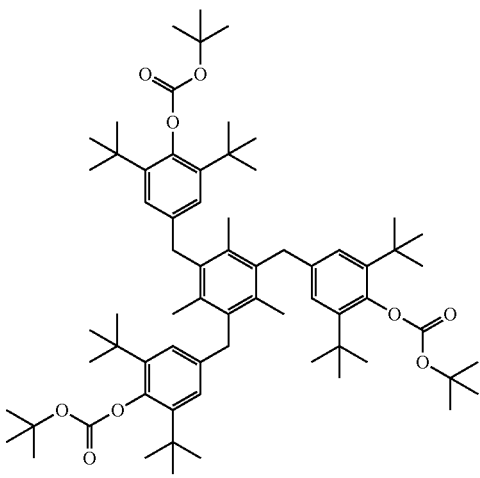

Compound No. 3

-continued
Compound No. 4
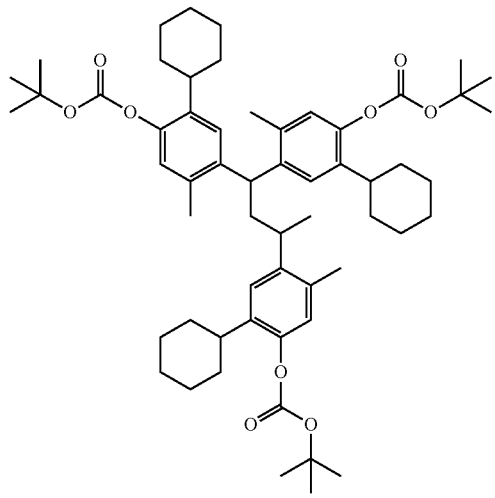
Compound No. 5
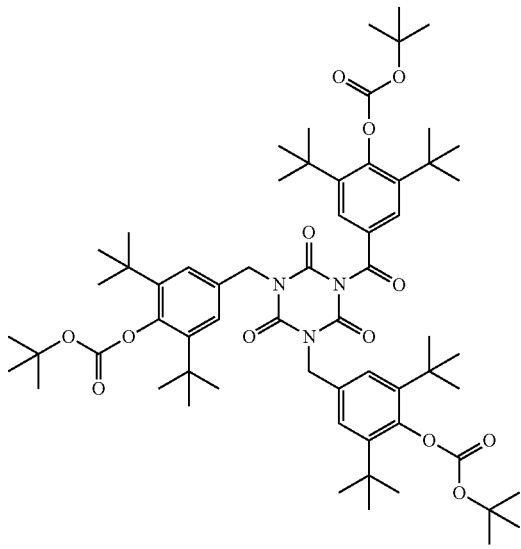
Compound No. 6
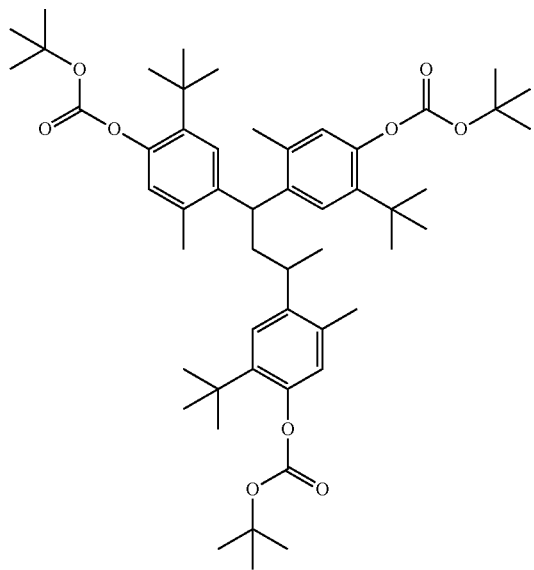
Compound No. 7
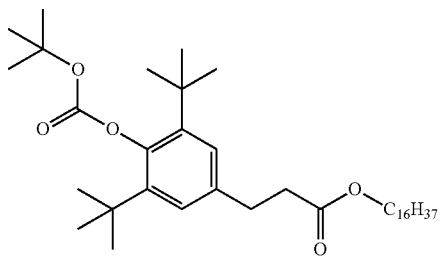

[Chem. 80D]
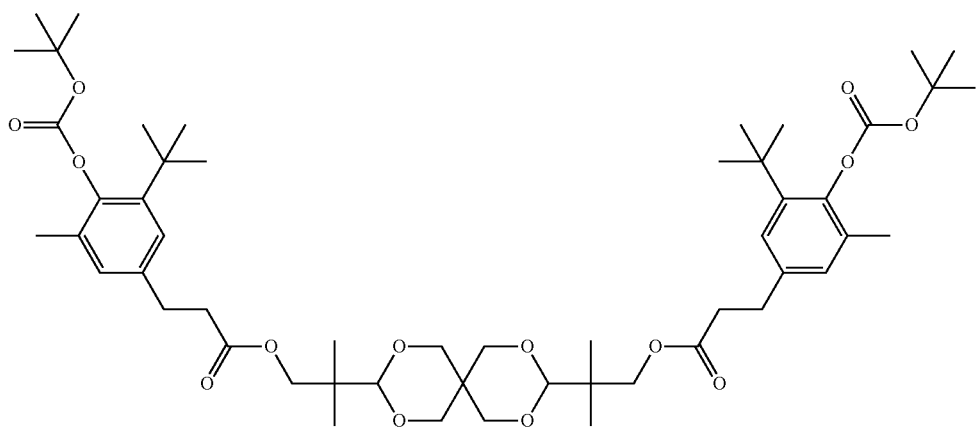
Compound No. 8
[Chem. 80E]
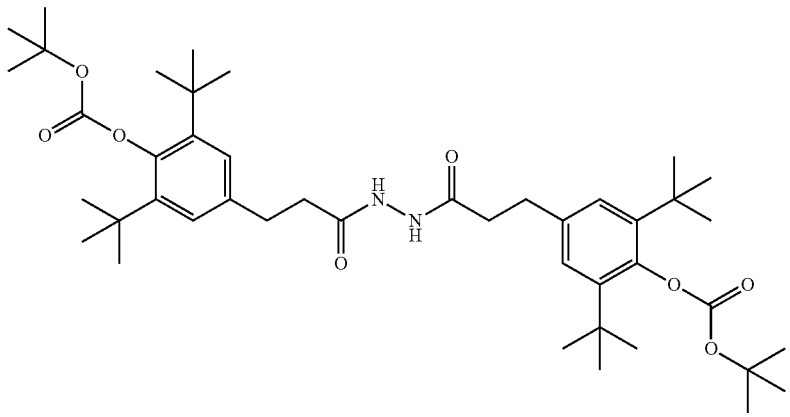
Compound No. 9
[Chem. 80F]
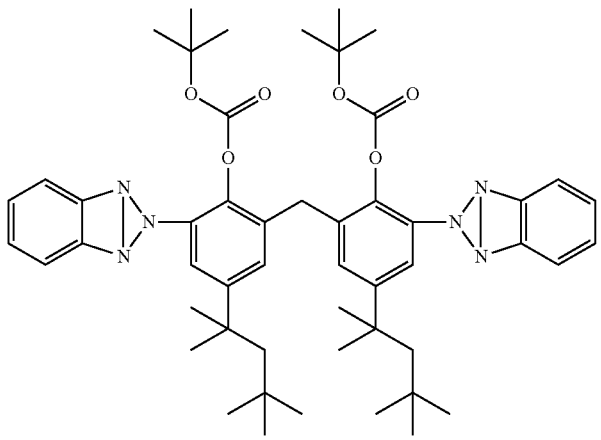
Compound No. 10

[Chem. 80G]

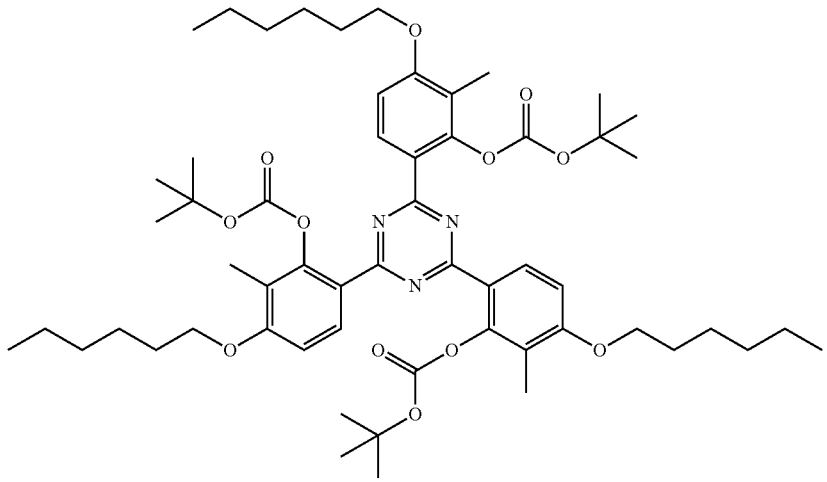

Compound No. 11

TABLE 1

| | Chemical Shift (ppm) (multiplicity, number of protons) |
|---|---|
| Compound No. 1 | 7.21 (s, 2H), 6.78 (s, 2H), 4.18 (d, 1H), 2.22 (s, 6H), 1.85 (q, 2H), 1.54 (s, 18H), 1.32 (q, 2H), 1.28 (s, 18H), 0.91 (t, 3H) |
| Compound No. 2 | 7.11 (s, 8H), 4.15 (s, 8H), 2.89 (t, 8H), 2.64 (t, 8H), 1.52 (s, 36H), 1.35 (s, 72H) |
| Compound No. 3 | 6.98 (s, 3H), 4.05 (s, 3H), 2.20 (s, 9H), 1.51 (s, 27H), 1.26 (s, 54H) |
| Compound No. 4 | 7.24 (s, 1H), 7.11 (s, 1H), 7.00 (s, 1H), 6.78 (s, 1H), 6.76 (s, 1H), 6.74 (s, 1H), 4.02 (t, 1H), 3.00-2.92 (m, 1H), 2.64 (m, 2H), 2.57 -2.51 (m, 1H), 2.23-2.03 (m, 2H), 2.14 (s, 3H), 1.87 (s, 3H), 1.84-1.73 (m, 14H), 1.70 (s, 3H), 1.62-1.47 (m, 2H), 1.55 (s, 9H), 1.54 (s, 9H), 1.53 (s, 9H), 1.39-1.27 (m, 14H), 1.20 (d, 3H) |
| Compound No. 5 | 7.50 (s, 6H), 4.94 (s, 6H), 1.51 (s, 27H), 1.33 (s, 54H) |
| Compound No. 6 | 7.37 (s, 1H), 7.20 (s, 1H), 7.04 (s, 1H), 6.76 (s, 1H), 6.75 (s, 1H), 6.72 (s, 1H), 3.93 (t, 1H), 2.94 (m, 1H), 2.12 (s, 3H), 2.10-2.00 (m, 2H), 1.84 (s, 3H), 1,66 (s, 3H), 1.54 (s, 9H), 1.54 (s, 9H), 1.53 (s, 9H), 1.47 (d, 3H), 1.37 (s, 9H), 1.34 (s, 9H), 1.21 (s, 9H) |
| Compound No. 7 | 7.11 (s, 2H), 4.07 (t, 2H), 2.90 (t, 2H), 2.61 (t, 2H), 1.61-1.60 (m, 8H), 1.53 (s, 8H), 1.35 (s, 18H), 1.31-1.24 (m, 16H), 1.25 (s, 9H), 0.88 (t, 3H) |
| Compound No. 8 | 7.02 (s, 2H), 6.92 (s, 2H), 4.49 (s, 1H), 4.47 (s, 1H), 4.19 (s, 2H), 3.92 (s, 4H), 3.55 (s, 1H), 3.54 (s, 1H), 3.52 (s, 1H), 3.51 (s, 1H), 3.28 (s, 1H), 3.25 (s, 1H), 2.88 (t, 4H), 2.61 (t, 4H), 2.14 (s, 6H), 1.54 (s, 18H), 1.34 (s, 18H), 0.92 (s, 6H), 0.91 (s, 6H) |
| Compound No. 9 | 7.04 (s, 4H), 5.05 (s, 2H), 3.25-3.18 (m, 4H), 2.91-2.87 (m, 4H), 1.45 (s, 18H), 1.43 (s, 36H) |
| Compound No. 10 | 8.01-7.99 (d, 2H), 7.95-7.91 (dd, 4H), 7.44-7.39 (dd, 4H), 7.34-7.32 (d, 2H), 4.17 (s, 2H), 1.73 (s, 4H), 1.47 (s, 18H), 1.35 (s, 12H) |
| Compound No. 11 | 8.52-8.50 (d, 3H), 6.88-6.85 (d, 3H), 4.08-4.03 (t, 6H), 2.19 (s, 9H), 1.85-1.80 (m, 6H), 1.54-1.45 (m, 6H), 1.38-1.32 (m, 12H), 1.29 (s, 18H), 0.94-0.91 (t, 9H) |

$^1$H-NMR (solvent:CDCL$_3$)

TABLE 2

| | IR Absorption Spectrum (cm$^{-1}$) |
|---|---|
| Compound No. 1 | 2956, 2871, 1752, 1500, 1395, 1370, 1246, 1151, 1064, 905, 887, 784, 794 |
| Compound No. 2 | 2962, 1754, 160, 1474, 1456, 1431, 1395, 1368, 1257, 1212, 1154, 1114, 891, 820 |
| Compound No. 3 | 2970, 1753, 1597, 1429, 1395, 1368, 1254, 1146, 1113, 1048, 1018, 889, 863, 819, 783 |

TABLE 2-continued

| | IR Absorption Spectrum (cm$^{-1}$) |
|---|---|
| Compound No. 4 | 2926, 2852, 1758, 1499, 1450, 1370, 1250, 1146, 891, 858, 782 |
| Compound No. 5 | 2965, 1755, 1686,1898, 1449, 1494, 1368, 1324, 1203, 1110, 893, 794, 783, 770, 738, 502 |
| Compound No. 6 | 2962, 1754, 1500, 1454, 1393, 1368, 1244, 1140, 1102, 893, 861, 781 720, 501 |
| Compound No. 7 | 2950, 2918, 2850, 1755, 1737, 1597, 1467, 1427, 1393, 1366, 1254, 1151, 1112, 891, 870, 782, 720 |
| Compound No. 8 | 2972, 2856, 1760, 1734, 1473, 1399, 1371, 1273, 1254, 1169, 1092, 1043, 950, 876, 772, 717, 546 |
| Compound No. 9 | 3618, 2959, 2871, 1592, 1737, 1737, 1718, 1434, 1291, 1276, 1245, 1148, 1106, 1059, 998, 842, 756 |
| Compound No. 10 | 3071, 2958, 1768, 1596, 1565, 1492, 1469, 1429, 1406, 1397, 1371, 1354, 1279, 1255, 1228, 1151, 1133, 1110, 896, 748 |
| Compound No. 11 | 2932, 2871, 1759, 1606, 1585, 1517, 1493, 1469, 1433, 1394, 1369, 1353, 1278, 1149, 1107, 1046, 1015, 895, 876, 807, 768, 620 |

TABLE 3

| | Melting Point (° C.) |
|---|---|
| Compound No. 1 | 164 |
| Compound No. 2 | 155 |
| Compound No. 3 | 156 |
| Compound No. 4 | 209 |
| Compound No. 5 | 186 |
| Compound No. 6 | 218 |
| Compound No. 7 | 61 |
| Compound No. 8 | 224 |
| Compound No. 9 | 153 |
| Compound No. 10 | 12 |
| Compound No. 11 | No Melting Point |

Example 2-1 and Comparative Example 2-1

Preparation of Polymerizable Composition No. 1 and Comparative Polymerizable Composition No. 1

In a 50 ml four-necked flask were put 2.97 g of methyl methacrylate and 0.03 g of azobisisobutyronitrile, and 0.01 g of compound No. 1 (Example 2-1) or comparative compound No. 1 and 7.00 g of toluene were added thereto, followed by stirring at 80° C. for 2 hours. The reaction product was analyzed by GPC to determine the molecular weight. The results are shown in Table 4.

TABLE 4

| Compound | Example 2-1 | Comparative Example 2-1 |
|---|---|---|
| Compound | compound No. 1 | comparative compound No. 1 |
| Average Mol. Wt. (Mw/Mn) | 5.8 × 10$^4$/2.6 × 10$^4$ | N.D. |

Comparative Compound No. 1:

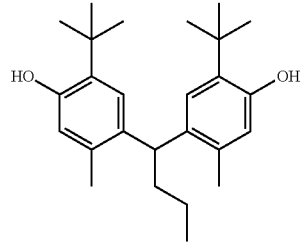

[Chem. 81]

The above results clearly demonstrate that the comparative polymerizable composition containing a compound having a phenol group undergoes polymerization inhibition while the polymerizable composition having the latent additive of the invention does not undergo polymerization inhibition.

Examples 3-1 to 3-8 and Comparative Examples 3-1 to 3-8

Preparation of Colored Photosensitive Compound Nos. 1 to 8 and Comparative Colored Photosensitive Composition Nos. 1 to 8

Step 1: Preparation of Photosensitive Composition Nos. 1 to 8 and Comparative Photosensitive Composition Nos. 1 to 8

SPC-1000 (29% PGMEA solution, available from Showa Denko K.K.) (50.9 g), 11.9 g of Aronix M-450 (from ToaGosei Co. Ltd.), 1.04 g of OXE-01 (from BASF), 34.0 g of PGMEA, 2.9 g of FZ2122 (1% PGMEA solution, from Toray Dow Corning), and 0.81 g of the latent additive shown in Table 5 were mixed and stirred to completely dissolve to prepare photosensitive composition Nos. 1 to 8 and comparative photosensitive composition Nos. 1 to 8.

TABLE 5

| | Latent Additive | Colorant |
|---|---|---|
| Example 3-1 | compound No. 2 | compound No. D-1 |
| Example 3-2 | compound No. 2 | compound No. D-2 |
| Example 3-3 | compound No. 2 | compound No. D-3 |
| Example 3-4 | compound No. 2 | compound No. D-4 |
| Example 3-5 | compound No. 4 | compound No. D-5 |
| Example 3-6 | compound No. 1 | compound No. D-6 |
| Example 3-7 | compound No. 2 | compound No. D-7 |
| Example 3-8 | compound No. 3 | compound No. D-8 |
| Comp. Example 3-1 | none | compound No. D-1 |
| Comp. Example 3-2 | " | compound No. D-2 |
| Comp. Example 3-3 | " | compound No. D-3 |
| Comp. Example 3-4 | " | compound No. D-4 |
| Comp. Example 3-5 | " | compound No. D-5 |
| Comp. Example 3-6 | " | compound No. D-6 |
| Comp. Example 3-7 | " | compound No. D-7 |
| Comp. Example 3-8 | " | compound No. D-8 |

Step 2: Preparation of Colorant Solution. Nos. 1 to 8
A colorant (0.10 g) was dissolved in 1.90 g of PGMEA by stirring.
Step 3: Preparation of Colored Photosensitive Composition Nos. 1 to 8 and Comparative Colored Photosensitive Composition Nos. 1 to 8

Each of the photosensitive composition Nos. 1 to 8 and comparative photosensitive composition Nos. 1 to 8 measuring 2.50 g was uniformly mixed with 1.00 g of one of the colorant solution Nos. 1 to 8 prepared in step 2 according to the latent additive/colorant combination shown in Table 5 to prepare colored photosensitive composition Nos. 1 to 8 and comparative colored photosensitive composition Nos. 1 to 8.

[Chem. 82]

Compound No. D-1

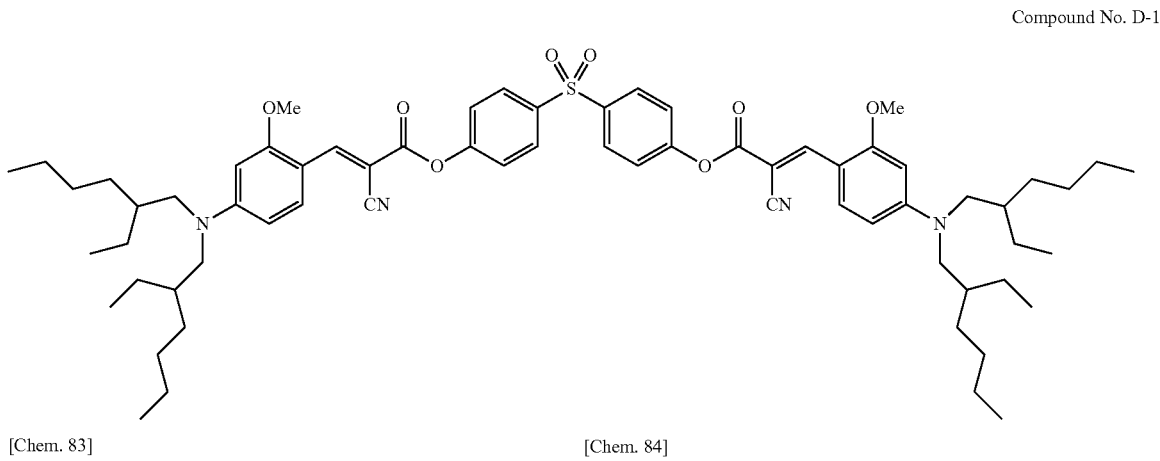

[Chem. 83]

Compound No. D-2

[Chem. 84]

Compound No. D-3

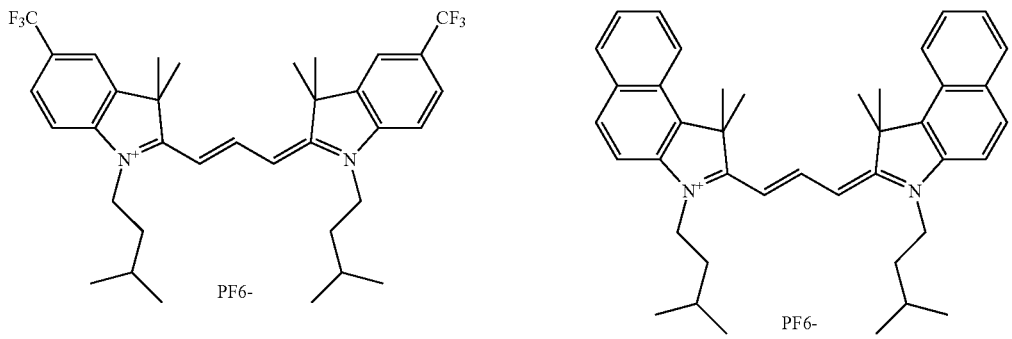

[Chem. 85]

Compound No. D-4

[Chem. 86]

Compound No. D-5

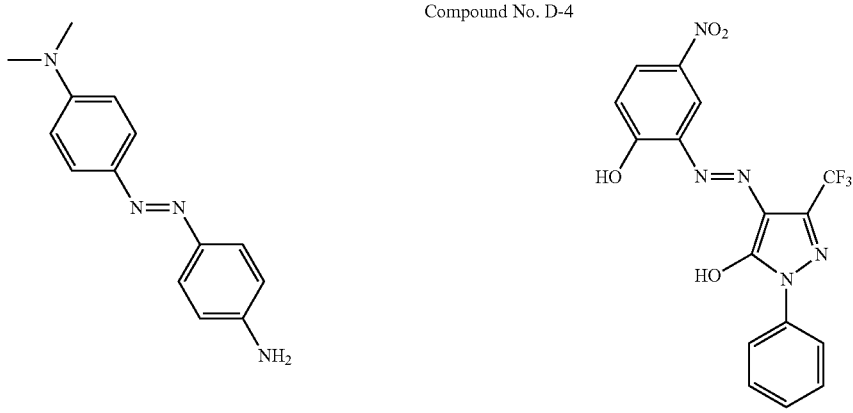

-continued

Compound No. D-6

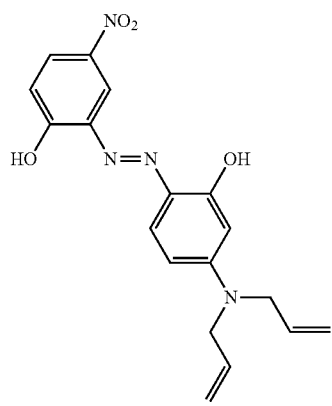

Compound No. D-7

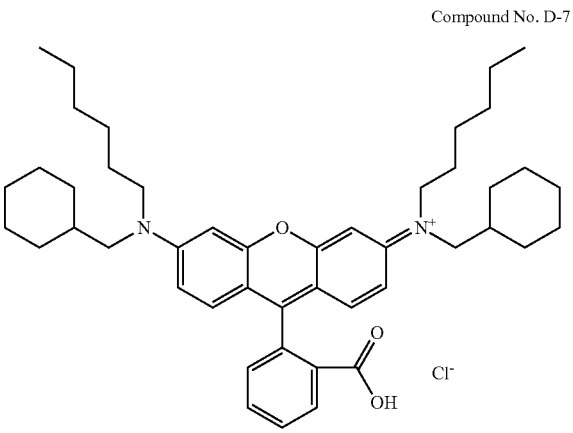

Compound No. D-8

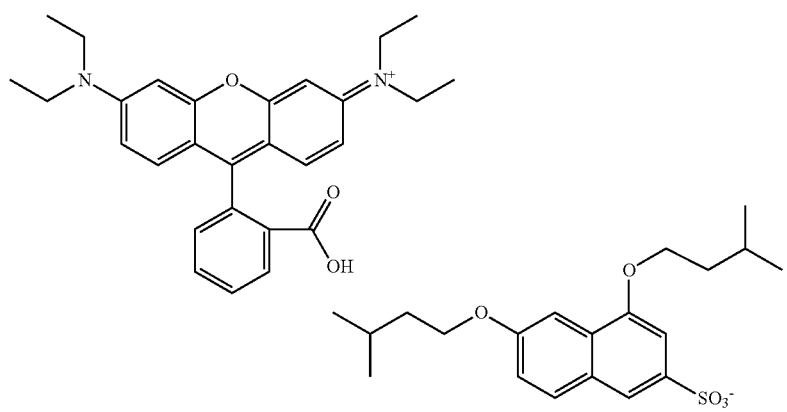

Example 4-1 and Comparative Examples 4-1 and 4-2

Preparation of Photosensitive Composition No. 9 and Comparative Photosensitive Composition Nos. 9 and 10

SPC-1000 (29% PGMEA solution, available from Showa Denko K.K.) (50.9 g), 11.9 g of Aronix M-450 (from ToaGosei Co., Ltd.), 0.3 g of NCI-930 (from ADEKA), 34.0 g of PGMEA, 2.9 g of FZ2122 (1% PGMEA solution, from Toray Dow Corning), and 0.81 g of the additive shown in Table 6 were mixed and stirred to completely dissolve to prepare photosensitive composition No. 9 and comparative photosensitive composition Nos. 9 and 10.

TABLE 6

| | Additive |
|---|---|
| Example 4-1 | compound No. 2 |
| Comparative Example 4-1 | comparative compound No. 2 |
| Comparative Example 4-2 | none |

Comparative Compound No. 2:

TABLE 6-continued

| Additive |
|---|

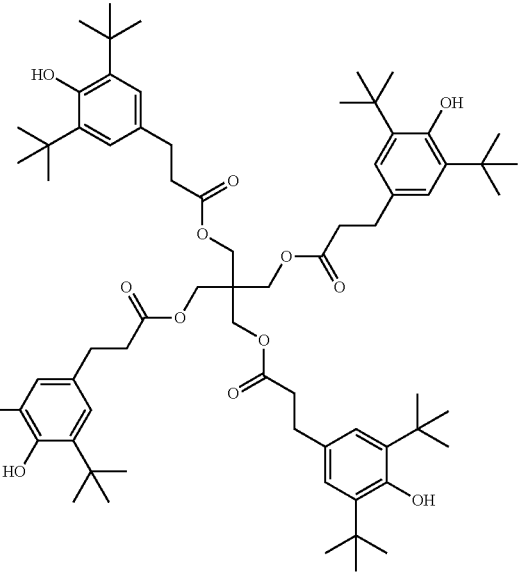

[Chem. 90]

Example 5-1 and Comparative Examples 5-1 and 5-2

Preparation of Thermosetting Composition No. 1 and Comparative Thermosetting Composition Nos. 1 and 2

Resins and an additives were mixed in accordance with the formulation of Table 7 (unit: part by mass), and the mixture was stirred at 50° C. and 300 to 400 rpm for 1 hour to completely dissolve. To the mixture was added 0.75 g of CP-66 (from ADEKA) as a thermal initiator, followed by stirring at 400 to 500 rpm for 1 hour.

TABLE 7

|  |  | Example 5-1 | Compara. Example 5-1 | Compara. Example 5-2 |
|---|---|---|---|---|
| Resin | DCA*[1] | 56 | 56 | 56 |
|  | YX-8000*[2] | 24 | 24 | 24 |
|  | BF-1000*[3] | 20 | 20 | 20 |
| Additive | Compound No. 2 | 1.33 | — | — |
|  | Comparative Compound No. 2 | — | 1 | — |

*[1]: 2,2-Bis(3,4-epoxycyclohexylpropane)
*[2]: Hydrogenated bisphenol A epoxy resin (from Mitsubishi Chemical)
*[3]: Epoxidized polybutadiene (from ADEKA)

Example 6-1 and Comparative Examples 6-1 and 6-2

Preparation of Photocuring Composition No. 1 and Comparative Photocuring Composition Nos. 1 and 2

Step 1: Preparation of Photocuring Composition No. 1 and Comparative Photocuring Composition Nos. 1 and 2

SPC-1000 (29% PGMEA solution, available from Showa Denko K.K.) (49.6 g), 11.5 g of Aronix M-450 (from ToaGosei Co., Ltd.), 1.0 g of OXE-01 (from BASF), 35.0 g of PGMEA, 2.9 g of FZ2122 (1% PGMEA solution, from Toray Dow Corning), and 2.0 g of the additive shown in Table 8 were mixed to prepare photocuring composition No. 1 and comparative photocuring composition Nos. 1 and 2.

TABLE 8

|  | Additive |
|---|---|
| Example 6-1 | compound No. 10 |
| Compara. Example 6-1 | comparative compound No. 3 |
| Compara. Example 6-2 | none |

Comparative Compound No. 3:

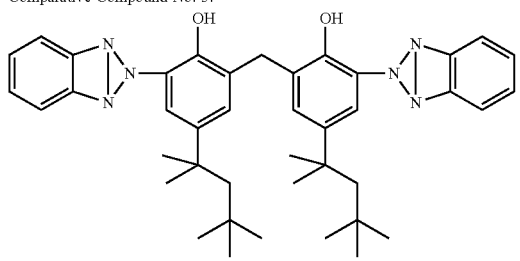

[Chem. 91]

Evaluation Examples 1-1 to 1-8 and Comparative Evaluation Examples 1-1 to 1-8

Baking heat resistance test

Colored photosensitive composition Nos. 1 to 8 and comparative colored photosensitive composition Nos. 1 to 8 prepared above were each applied to a glass plate under conditions of 410 rpm×7 sec and dried on a hot plate (90° C., 90 sec). The resulting coating film was exposed to light (150 mJ/cm$^2$) from an ultrahigh pressure mercury lamp. The exposed film was baked at 230° C. for 30 minutes. The absorbances of the exposed film before and after the baking at a maximal absorption wavelength ($\lambda_{max}$) of the colorant added were determined and expressed relatively taking the absorbance before baking as 100. The closer the pre-baking absorbance to 100, the higher the heat resistance. The results are shown in Table 9.

TABLE 9

|  | Colored Photosensitive Composition | Relative Intensity |
|---|---|---|
| Evaluation Example 1-1 | colored photosensitive composition No. 1 | 91.4 |
| Evaluation Example 1-2 | colored photosensitive composition No. 2 | 74.1 |
| Evaluation Example 1-3 | colored photosensitive composition No. 3 | 16.6 |
| Evaluation Example 1-4 | colored photosensitive composition No. 4 | 49.3 |
| Evaluation Example 1-5 | colored photosensitive composition No. 5 | 13.4 |
| Evaluation Example 1-6 | colored photosensitive composition No. 6 | 31.5 |
| Evaluation Example 1-7 | colored photosensitive composition No. 7 | 18.7 |
| Evaluation Example 1-8 | colored photosensitive composition No. 8 | 97.3 |
| Comparative Evaluation Example 1-1 | comparative colored photosensitive composition No. 1 | 60.2 |
| Comparative Evaluation Example 1-2 | comparative colored photosensitive composition No. 2 | 62.6 |
| Comparative Evaluation Example 1-3 | comparative colored photosensitive composition No. 3 | 14.7 |
| Comparative Evaluation Example 1-4 | comparative colored photosensitive composition No. 4 | 46.1 |
| Comparative Evaluation Example 1-5 | comparative colored photosensitive composition No. 5 | 8.0 |
| Comparative Evaluation Example 1-6 | comparative colored photosensitive composition No. 6 | 23.6 |
| Comparative Evaluation Example 1-7 | comparative colored photosensitive composition No. 7 | 15.7 |
| Comparative Evaluation Example 1-8 | comparative colored photosensitive composition No. 8 | 88.2 |

It is apparent from comparisons between colored photosensitive compositions containing the same colorant that those according to the invention exhibit higher heat resistance than the comparative ones by virtue of the latent additive.

Evaluation Examples 2-1 to 2-3 and Comparative Evaluation Examples 2-1 to 2-6

Measurement of Line Width Sensitivity (Test For Curing Inhibition)

Colored photosensitive composition Nos. 1 to 3 prepared in Examples 3-1 to 3-3, comparative colored photosensitive composition Nos. 1 to 3 prepared in Comparative Examples 3-1 to 3-3, and comparative colored photosensitive composition Nos. 4 to 6 prepared by adding 0.81 g of comparative compound No. 2 to comparative colored photosensitive composition Nos. 1 to 3 were each applied to a glass plate under conditions of 410 rpm×7 sec and dried on a hot plate (90° C., 90 sec). The resulting coating film was exposed to light from an ultrahigh pressure mercury lamp at an exposure energy stepwise increasing from 50 mJ/cm$^2$ to 270 mJ/cm$^2$ by 30 mJ/cm$^2$ in 8 steps through a mask overlaid with a gap of 20 µm. The exposed film was developed with an alkali developer and baked at 230PC for 30 minutes. The developed line width formed under a slit of 20 µm in width at every exposure energy was plotted. The amount of exposure required to form a 20 µn wide line was taken as a line width sensitivity. The results are shown in Table 10. The smaller the value, the higher the sensitivity.

TABLE 10

|  |  | 20 µm Line Width Sensitivity (mJ/cm$^2$) |
|---|---|---|
| Evaluation Example 2-1 | colored photosensitive composition No. 1 | 57 |
| Evaluation Example 2-2 | colored photosensitive composition No. 2 | 60 |
| Evaluation Example 2-3 | colored photosensitive composition No. 3 | 181 |
| Comparative Evaluation Example 2-1 | comparative colored photosensitive composition No. 1 | 57 |
| Comparative Evaluation Example 2-2 | comparative colored photosensitive composition No. 2 | 50 |
| Comparative Evaluation Example 2-3 | comparative colored photosensitive composition No. 3 | 203 |
| Comparative Evaluation Example 2-4 | comparative colored photosensitive composition No. 4 | 138 |
| Comparative Evaluation Example 2-5 | comparative colored photosensitive composition No. 5 | 187 |
| Comparative Evaluation Example 2-6 | comparative colored photosensitive composition No. 6 | ≥1000 |

It is seen from the results in Table 10 that the cured products from comparative colored photosensitive composition Nos. 4 to 6 containing comparative compound No. 2, which is a conventionally used phenol antioxidant, have low line width sensitivity, indicating occurrence of cure inhibition. In contrast, the cured products from colored photosensitive composition Nos. 1 to 3 containing the latent antioxidant of the invention exhibit high line width sensitivity, indicating no occurrence of cure inhibition.

Evaluation Example 3-1 and Comparative Evaluation Examples 3-1 to 3-2

Baking Heat Resistance Test

Photosensitive composition No. 9 and comparative photosensitive composition Nos. 9 and 10 prepared above were evaluated for heat resistance in the same manner as in Evaluation Example 1. The results obtained are shown in Table 11.

Photosensitive composition No. 9 and comparative photosensitive composition Nos. 9 and 10 prepared above were each applied to a glass plate under conditions of 410 rpm×7 sec and dried on a hot plate (90° C., 90 sec). The resulting coating film was exposed to light (150 m/cm$^2$) from an ultrahigh pressure mercury lamp. The exposed film was baked at 230° C. for 90 minutes. The transmittance of the baked film was measured. The closer the transmittance to 100, the higher the heat resistance.

The results are shown in Table 11.

TABLE 11

|  | Photosensitive Composition | Transmittance at 400 nm |
|---|---|---|
| Evaluation Example 3-1 | photosensitive composition No. 9 | 98.7% |
| Comparative Evaluation Example 3-1 | comparative photosensitive composition No. 9 | 98.2% |
| Comparative Evaluation Example 3-2 | comparative photosensitive composition No. 10 | 95.8% |

It is apparent from the results above that the photosensitive composition of the invention has higher heat resistance than the comparative photosensitive compositions by virtue of the latent additive.

Evaluation Example 4-1 and Comparative Evaluation Examples 4-1 and 4-2

Measurement of Line Width Sensitivity

Photosensitive composition No. 9 and comparative photosensitive composition Nos. 9 and 10 prepared above were tested for line width sensitivity in the same manner as in Evaluation Example 2. The results are shown in Table 12.

TABLE 12

|  | Photosensitive Composition | 20 µm Line Width Sensitivity (mJ/cm$^2$) |
|---|---|---|
| Evaluation Example 3-1 | photosensitive composition No. 9 | 46 |
| Comparative Evaluation Example 3-1 | comparative photosensitve composition No. 9 | >80 |
| Comparative Evaluation Example 3-2 | comparative photosensitive composition No. 10 | 46 |

It is seen from the above results that the cured product from comparative photosensitive composition No. 9 containing comparative compound No. 2, which is a conventionally used phenol antioxidant, has low line width sensitivity, indicating occurrence of cure inhibition. In contrast, the cured product from photosensitive composition No. 9 containing the latent antioxidant of the invention exhibits high line width sensitivity, indicating no occurrence of cure inhibition.

Evaluation Example 5-1 and Comparative Evaluation Examples 5-1 and 5-2

Evaluation of Thermal Cure

A glass plate having an untreated PET film stuck thereto was prepared. A 0.5 to 1.0 mm thick spacer of a fluororesin was provided on the glass plate, and a release-treated glass plate was superposed on the glass plate with the spacer in between. Thermosetting composition No. 1 and comparative thermosetting composition Nos. 1 and 2 were each injected into the cell and heated in an oven at 150° C. for 1 hour to post-cure. After cooling, the cured resin film was released from the glass plate and then heated at 2000° C. for 1 hour to perform a heat resistance test. The transmittances of the cured film before and after the heat resistance test were measured using an absorptiometer. The results are shown in Table 13.

TABLE 13

|  | Thermosetting Composition | Transmittance at 400 nm | |
|---|---|---|---|
|  |  | before Heating resistance test | after Heating resistance test |
| Evaluation Example 5-1 | thermosetting composition No. 1 | 85% | 68% |
| Comparative Evaluation Example 5-1 | comparative thermosetting composition No. 1 | 85% | 71% |
| Comparative Evaluation Example 5-2 | comparative thermosetting composition No. 2 | 83% | 53% |

Evaluation Example 6-1 and Comparative Evaluation Examples 6-1 and 6-2

Evaluation of Pot Life

Thermosetting composition No. 1 and comparative thermosetting composition No. 1 were allowed to stand in a cool and dark place. The number of days of storage until the viscosity increased by 30% was taken as a measure of a pot life. The results are shown in Table 14.

TABLE 14

|  | Thermosetting Composition | Pot Life |
|---|---|---|
| Evaluation Example 6-1 | thermosetting composition No. 1 | 2 wks |
| Comparative Evaluation Example 6-1 | comparative thermosetting composition No. 1 | 1 wk |

The results in Table 13 prove that thermosetting composition No. 1 containing the additive of the invention and comparative thermosetting composition No. 1 containing the comparative compound had higher transmittances at 400 nm after the heat resistance test, which indicate higher heat resistance, than comparative thermosetting composition No. 2 containing no additive. The results in Table 14 reveal that, since the phenol group of the additive of the invention is protected, the additive of the invention has a longer pot life and higher storage stability than the comparative compound. The additive of the invention is thus proved suited to be applied to thermosetting compositions.

Evaluation Example 7-1 and Comparative Evaluation Example 7-1

Evaluation of UV Absorber Regeneration by Baking

Photocuring composition No. 1 and comparative photocuring composition No. 2 were each applied to a glass plate under conditions of 410 rpm×7 sec and dried on a hot plate (90° C., 90 sec). The resulting coating film was exposed to light (150 mJ/cm$^2$) from an ultrahigh pressure mercury lamp. The exposed film was baked at 230° C. for 30 minutes. The transmittances of the exposed film before and after the baking at 365 nm were measured. Comparative photocuring composition No. 1 was not evaluated because it did not dissolve and got turbid. The results are shown in Table 15.

TABLE 15

|  | Photocuring Composition | Transmittance at 365 nm (%) | |
|---|---|---|---|
|  |  | before Baking | after Baking |
| Evaluation Example 7-1 | photocuring composition No. 1 | 87.90 | 21.50 |
| Comparative Evaluation Example 7-1 | comparative photocuring composition No. 2 | 87.40 | 94.80 |

The reason why Comparative Evaluation Example 7-1 showed an increase in transmittance after baking is that the photo radical polymerization initiator capable of absorbing light at 365 nm decomposed thermally to lose its absorption at 365 inn. Although thermal decomposition of the photo radical polymerization initiator similarly occurred in Evaluation Examples 7-1, it is apparent that the latent additive of the invention was deprotected upon baking to act as a UV absorber capable of absorbing light of 365 nm.

It is apparent from the above results that the latent additive of the invention in the photocuring composition undergoes deprotection in baking to serve as a UV absorber having a phenol group.

Reference Example

Verification of Deprotection of Latenta Antioxidant by Heating

Five milligrams of compound No. 1 was weighed out and heated on a thermogravimetric analyzer from room temperature up to 230° C. at a rate of 10° C./min and maintained at that temperature for 30 minutes, whereupon a weight loss of 26 mass % was observed. This weight loss corresponds to the t-butoxycarbonyl group and indicates deprotection on heating. Appearance of a phenol group was confirmed by $^1$H-NMR and IR analyses.

TABLE 16

| $^1$H-NMR (solvent: CDCl$_3$) | |
|---|---|
| Chemical Shift (ppm) (multiplicity, number of protons) | |
| before Heating | 7,11 (s, 8H), 4.15 (s, 8H), 2.89 (t, 8H), 2.64 (t. 8H), 1.52 (s, 36H), 1,35 (s, 72H) |
| after Heating | 6.97 (s, 8H), 5.06 (s, 4H), 4.08 (s, SH), 2.84 (t, 8H), 2.60 (t, 8H), 1.35 (s, 72H) |

As shown by the underlined chemical shifts, it is understood that the protons of a t-butoxycarbonyl group disappeared and new protons assigned to a phenol group appeared instead.

TABLE 17

| IR Absorption Spectrum (cm$^{-1}$) | |
|---|---|
| before Heating | 2962, 1754, 1600 (C═O), 1474, 1456, 1431, 1395, 1368, 1257, 1212, 1154, 1114, 891, 820 |
| after Heating | 3642 (OH), 2959, 2873, 1742, 1436, 1391, 1361, 1315, 1234, 1142, 1037, 887, 874, 768 |

As indicated by the underlined wavenumbers, it is seen that the stretching vibration of C═O disappeared and a new stretching vibration of OH appeared.

It is apparent from the above results that the latent additive of the invention becomes a phenolic additive on heating.

It has thus been made clear from the above results that the latent additive of the invention is inactive at room temperature and becomes active on heating to a predetermined temperature and that a cured product of a composition containing the latent additive exhibits excellent heat resistance without suffering from cure inhibition.

The invention claimed is:
1. A composition comprising
a latent additive represented by formula (1):

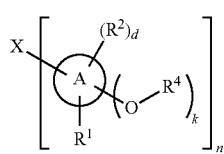

(1)

wherein A represents a benzene ring;
$R^1$ represents a C4-C6 alkyl group;
$R^2$ represents a hydrogen atom, a halogen atom, a cyano group, a hydroxyl group, a nitro group, a carboxyl group, an optionally substituted C1-C40 alkyl group, a C6-C20 aryl group, a C7-C20 arylalkyl group, or a C2-C20 heterocyclic ring-containing group;
$R^4$ represents a C2-C9 alkoxycarbonyl group;
$R^1$ is adjacent to —(O—$R^4$)$_k$;
the methylene moiety of the alkyl or arylalkyl group represented by $R^1$, and $R^2$ may be replaced by a combination of one or more groups selected from a carbon-carbon double bond, —S—, —O—CO—, —CO—O—, —O—CO—O—, —S—CO—, —CO—S—, —S—CO—O—, —O—CO—S—, —CO—NH—, —NH—CO—, —NH—CO—O—, —NR'—, >P=O, —S—S—, and —SO$_2$—;
the methylene moiety of the alkyl or arylalkyl group represented by $R^4$ may be replaced by a combination of one or more groups selected from a carbon-carbon double bond, —O—, —S—, —CO—, —O—CO—, —CO—O—, —O—CO—O—, —O—CO—O—, —S—CO—, —CO—S—, —S—CO—O—, —O—CO—S—, —CO—NH—, —NH—CO—, —NH—CO—O—, —NR'—, >P=O, —S—S—, and —SO$_2$—;
R' represents a hydrogen atom or a C1-C8 alkyl group;
a plurality of $R^2$'s may be taken together to form a benzene ring or a naphthalene ring;
a plurality of $R^2$'s may be the same or different; a plurality of $R^4$'s may be the same or different;
n represents an integer of 1 to 10;
d represents an integer of 1 to 3;
k represents an integer of 1 to 3; and
X represents a single bond, a nitrogen atom, an oxygen atom, a sulfur atom, a phosphorus atom, a group represented by

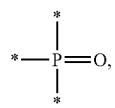

>P=O, >C=O, >NR$^{10}$, >PR$^{10}$, —OR$^{10}$, —SR$^{10}$, —NR$^{10}$R$^{11}$, —PR$^{10}$R$^{11}$, a C1-C120 aliphatic hydrocarbon group, a C6-C35 aromatic ring-containing hydrocarbon group, or a C2-C35 heterocyclic ring-containing group, the aliphatic hydrocarbon group, aromatic ring-containing hydrocarbon group, and heterocyclic ring-containing group having as many valences as n and optionally having a substituent;
$R^{10}$ and $R^{11}$ each represent a hydrogen atom, an optionally substituted C1-C35 aliphatic hydrocarbon group, an optionally substituted C6-C35 aromatic ring-containing hydrocarbon group, or an optionally substituted C2-C35 heterocyclic ring-containing group, the aliphatic hydrocarbon group, aromatic ring-containing group, and heterocyclic ring-containing group being optionally substituted by a combination of one or more groups selected from a carbon-carbon double bond, —O—, —S—, —CO—, —O—CO—, —CO—O—, —O—CO—O—, —O—CO—O—, —S—CO—, —CO—S—, —S—CO—O—, —O—CO—S—, —CO—NH—, —NH—CO—, —NH—CO—O—, —NR'—, >P=O, —S—S—, —SO$_2$—, and a nitrogen atom;
the aromatic or heterocyclic ring may be fused to one or more additional rings;
when X is a nitrogen atom, a phosphorous atom, or the group represented by

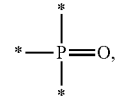

n is 3;
when X is an oxygen atom or a sulfur atom, n is 2;
when X is >C=O, —NH—CO—, —CO—NH—, >NR$^{10}$, or >PR$^{10}$, n is 2; and when X is —OR$^{10}$, —SR$^{10}$, —NR$^{10}$R$^{11}$, or —PR$^{10}$R$^{11}$, n is 1; and
X may be taken together with A to form a ring,
a radical polymerizable organic substance, and
a photo-radical polymerization initiator or a thermal radical polymerization initiator.
2. A compound represented by formula (2):

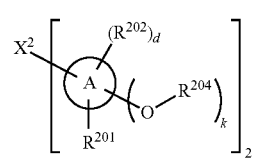

(2)

wherein
A represents a benzene ring;
$R^{201}$ represents a C4-C6 alkyl group;
$R^{202}$ represents a hydrogen atom, a halogen atom, a cyano group, a hydroxyl group, a nitro group, a carboxyl group, an optionally substituted C1-C40 alkyl group, a C6-C20 aryl group, or a C7-C20 arylalkyl group;
d represents an integer of 1 to 3;
k represents an integer of 1 to 3;
$R^{204}$ represents a C2-C9 alkoxycarbonyl group;
$R^{201}$ is adjacent to —(O—$R^{204}$)$_k$;
the methylene moiety of the alkyl or arylalkyl group represented by $R^{201}$ and $R^{202}$ may be replaced by a combination of one or more groups selected from a carbon-carbon double bond, —S—, —O—CO—, —CO—O—, —O—CO—O—, —O—CO—O—, —S—CO—, —CO—S—, —O—CO—S—, —S—CO—O—, —CO—NH—, —NH—CO—, —NH—CO—O—, —NR'—, >P=O, —S—S—, and —SO$_2$—;

the methylene moiety of the alkyl or arylalkyl group represented by R$^{204}$ may be replaced by a combination of one or more groups selected from a carbon-carbon double bond, —O—, —S—, —CO—, —O—CO—, —CO—O—, —O—CO—O—, —O—CO—O—, —S—CO—, —CO—S—, —O—CO—S—, —S—CO—O—, —CO—NH—, —NH—CO—, —NH—CO—O—, —NR'—, >P=O, —S—S—, and —SO$_2$—;

R' represents a hydrogen atom or a C1-C8 alkyl group;

a plurality of R$^{202}$'s may be taken together to form a benzene ring or a naphthalene ring;

a plurality of R$^{202}$'s may be the same or different;

a plurality of R$^{204}$'s may be the same or different;

X$^2$ represents an oxygen atom, a sulfur atom, a group represented by

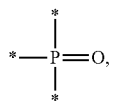

>C=O, —NH—CO—, —CO—NH—, >NR$^{12}$, >PR$^{12}$, a substituent represented by a group selected from formula (3), formula (4), or [Chem. 10] shown below;

R$^{12}$ represents a hydrogen atom, an optionally substituted C1-C35 aliphatic hydrocarbon group, an optionally substituted C6-C35 aromatic ring-containing hydrocarbon group, or an optionally substituted C2-C35 heterocyclic ring-containing group, the aliphatic hydrocarbon group, aromatic ring-containing hydrocarbon group, and heterocyclic ring-containing group being optionally substituted by a combination of one or more groups selected from a carbon-carbon double bond, —O—, —S—, —CO—, —O—CO—, —CO—O—, —O—CO—O—, —O—CO—O—, —S—CO—, —CO—S—, —O—CO—S—, —S—CO—O—, —CO—NH—, —NH—CO—, —NH—CO—O—, —NR'13, >P=O, —S—S—, and —SO$_2$—;

the aromatic or heterocyclic ring may be fused to one or more additional rings; and X$^2$ may be taken together with A to form a ring;

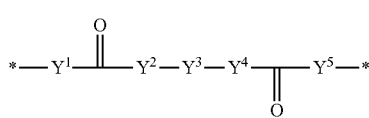

wherein Y$^1$ and Y$^5$ each independently represent a single bond, a C1-C4 alkylene group;

Y$^2$ and Y$^4$ each independently represent an oxygen atom or —NR$^{13}$—;

R$^{13}$ represents a hydrogen atom or a C1-C20 aliphatic hydrocarbon group;

Y$^3$ represents a single bond, —NR$^{16}$—, a divalent C1-C35 aliphatic hydrocarbon group, a divalent C6-C35 aromatic ring-containing group, or a substituent represented by formula (5) below, the aliphatic hydrocarbon group and C6-C35 aromatic ring-containing hydrocarbon group being optionally substituted by —COO—, —O—, —OCO—, 13 NHCO—, —NH—, or —CONH—;

and

R$^{16}$ represents a hydrogen atom, an optionally substituted C1-C35 aliphatic hydrocarbon group, an optionally substituted C6-C35 aromatic ring-containing hydrocarbon group, or an optionally substituted C2-C35 heterocyclic ring-containing group, the aliphatic hydrocarbon group, aromatic ring-containing hydrocarbon group, and heterocyclic ring-containing group being optionally substituted by a combination of one or more groups selected from a carbon-carbon double bond, —O—, —S—, —CO—, —O—CO—, —CO—O—, and —SO$_2$—;

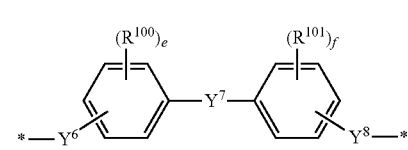

wherein Y$^6$ and Y$^8$ each independently represent —NR$^{17}$— or an optionally oxygen-interrupted C1-C4 alkylene group;

Y$^7$ represents a single bond, —O—, —S—, —SO$_2$—, —CR$^{18}$R$^{19}$—, or any one of the substituents represented by [Chem. 7], [Chem. 8] or [Chem. 9] shown below;

R$^{17}$ represents a hydrogen atom or a C1-C20 aliphatic hydrocarbon group;

R$^{100}$ and R$^{101}$ each independently represent a hydrogen atom, a halogen atom, a cyano group, a hydroxyl group, a nitro group, a carboxyl group, a C1-C8 alkyl group, or a C1-C8 alkoxy group; e represents a number of 1 to 4; and f represents a number of 1 to 4;

[Chem. 7]

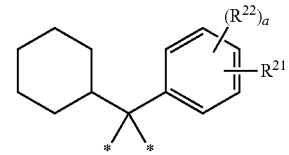

wherein R$^{21}$ represents a hydrogen atom, an optionally substituted phenyl group, or a C3-C10 cycloalkyl group; R$^{22}$ represents a C1-C10 alkyl group, a C1-C10 alkoxy group, a C2-C10 alkenyl group, or a halogen atom, the alkyl, alkoxy, or alkenyl group optionally having a substituent; and a represents an integer of 0 to 5;

[Chem. 8]

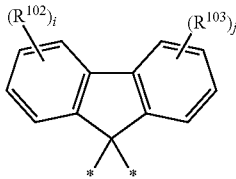

wherein $R^{102}$ and $R^{103}$ each independently represent a hydrogen atom, a halogen atom, a cyano group, a hydroxyl group, a nitro group, a carboxyl group, a C1-C8 alkyl group, or a C1-C8 alkoxy group;
i represents a number of 1 to 4; and j represents a number of 1 to 4;

[Chem. 9]

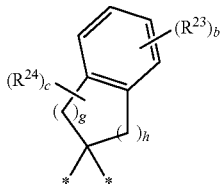

wherein $R^{23}$ and $R^{24}$ each independently represent an optionally substituted C1-C10 alkyl group, an optionally substituted C6-C20 aryl group, an optionally substituted C6-C20 aryloxy group, an optionally substituted C6-C20 arylthio group, an optionally substituted C6-C20 arylalkenyl group, an optionally substituted C7-C20 arylalkyl group, an optionally substituted C2-C20 heterocyclic ring-containing group, or a halogen atom, the methylene moiety of the alkyl and arylalkyl group being optionally replaced by an unsaturated bond, —O—, or —S—;
adjacent $R^{23}$'s may be taken together to form a ring;
b represents a number of 0 to 4;
c represents a number of 0 to 8; and
the sum of g and h is 2 to 4;

[Chem. 10]

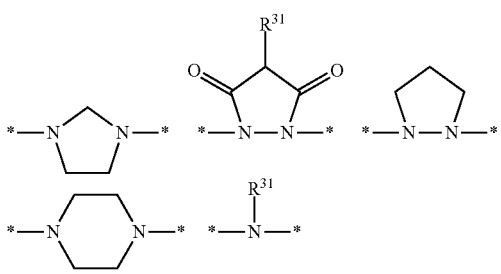

wherein $R^{31}$ represents a hydrogen atom, an optionally substituted C1-C35 aliphatic hydrocarbon group, an optionally substituted C6-C35 aromatic ring-containing hydrocarbon group, or an optionally substituted C2-C35 heterocyclic ring-containing group, the aliphatic hydrocarbon group being optionally substituted by a carbon-carbon double bond, —O—, —S—, —CO—, —O—CO—, —CO—O—, or —SO$_2$—;

[Chem. 11]

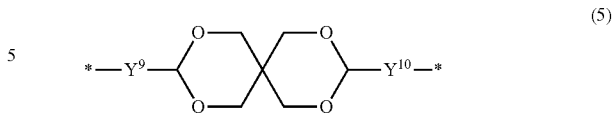

(5)

wherein $Y^9$ and $Y^{10}$ each independently represent a C1-C4 alkylene group.

3. A compound represented by formula (6):

[Chem. 12]

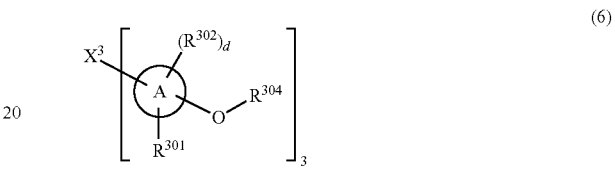

(6)

wherein
A represents a benzene ring;
$R^{301}$ represents a C4-C6 alkyl group;
$R^{302}$ represents a hydrogen atom, a halogen atom, a cyano group, a hydroxyl group, a nitro group, a carboxyl group, an optionally substituted C1-C40 alkyl group, a C6-C20 aryl group, a C7-C20 arylalkyl group, or a C2-C20 heterocyclic ring-containing group;
d represents an integer of 1 to 3;
k represents an integer of 1 to 3;
$R^{304}$ represents a C2-C9 alkoxycarbonyl group;
$R^{301}$ is adjacent to —(O—$R^{304}$);
the methylene moiety of the alkyl or arylalkyl group represented by $R^{301}$ and $R^{302}$ may be replaced by a combination of one or more groups selected from a carbon-carbon double bond, —S—, —O—CO—, —CO—O—, —O—CO—O—, —O—CO—, —S—CO—, —CO—S—, —O—CO—S—, —S—CO—O—, —CO—NH—, —NH—CO—, —NH—CO—O—, —NR'—, >P=O, —S—S—, —SO$_2$—, and a nitrogen atom;
the methylene moiety of the alkyl or arylalkyl group represented by $R^{304}$ may be replaced by a combination of one or more groups selected from a carbon-carbon double bond, —O—, —S—, —CO—, —O—CO—, —CO—O—, —O—CO—O—, —O—CO—, —S—CO—, —CO—S—, —O—CO—S—, —S—CO—O—, —CO—NH—, —NH—CO—, —NH—CO—O—, —NR'—, >P=O, —S—S—, —SO$_2$—, and a nitrogen atom;
R' represents a hydrogen atom or a C1-C8 alkyl group;
a plurality of $R^{302}$'s may be taken together to form a benzene ring or a naphthalene ring;
a plurality of $R^{302}$'s may be the same or different;
a plurality of $R^{304}$'s may be the same or different; and
$x^3$ represents a substituent represented by formula (7);
$x^3$ may optionally be taken together with A to form a ring, and the aromatic or heterocyclic ring may be fused to one or more additional rings,

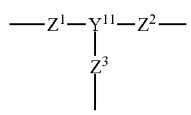
(7)

wherein Y¹¹ represents a trivalent C3-C35 aliphatic hydrocarbon group, a trivalent C3-C35 alicyclic hydrocarbon group, a trivalent C6-C35 aromatic ring-containing hydrocarbon group, or a trivalent C2-C35 heterocyclic ring-containing group;

$Z^1$, $Z^2$, and $Z^3$ each independently represent a single bond, —O—, —S—, >CO, —CO—O—, —O—CO—, —SO$_2$—, —SS—, —SO—, >NR$^{32}$, >PR$^{32}$, an optionally substituted C1-C35 aliphatic hydrocarbon group, an optionally substituted C6-C35 aromatic ring-containing hydrocarbon group, or an optionally substituted C2-C35 heterocyclic ring-containing group; and $R^{32}$ represents a hydrogen atom, an optionally substituted C1-C35 aliphatic hydrocarbon group, an optionally substituted C6-C35 aromatic ring-containing hydrocarbon group, or an optionally substituted C2-C35 heterocyclic ring-containing group, the aliphatic hydrocarbon group being optionally substituted by a combination of one or more groups selected from a carbon-carbon double bond, —O—, —S—, —CO—, —O—CO—, —CO—O—, and —SO$_2$—.

4. A compound represented by formula (8):

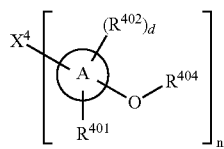
(8)

wherein

A represents a benzene ring;

$R^{401}$ represents a C4-C6 alkyl group;

$R^{402}$ represents a hydrogen atom, a halogen atom, a cyano group, a hydroxyl group, a nitro group, a carboxyl group, an optionally substituted C1-C40 alkyl group, a C6-C20 aryl group, a C7-C20 arylalkyl group, or a C2-C20 heterocyclic ring-containing group;

d represents an integer of 1 to 3;

k represents an integer of 1 to 3;

$R^{404}$ represents a C2-C9 alkoxycarbonyl group;

$R^{401}$ is adjacent to —(O—R$^{404}$);

the methylene moiety of the alkyl or arylalkyl group represented by $R^{401}$ and $R^{402}$ may be replaced by a combination of one or more groups selected from a carbon-carbon double bond, —S—, —O—CO—, —CO—O—, —O—CO—O—, —O—CO—O—, O—CO—O—, —O—O—O—, —S—CO—, —CO—S—, —O—CO—S—, —S—CO—O—, —CO—NH—, —NH—CO—, —NH—CO—O—, —NR'—, >P═O, —S—S—, and —SO$_2$—;

the methylene moiety of the alkyl or arylalkyl group represented by $R^{404}$ may be replaced by a combination of one or more groups selected from a carbon-carbon double bond, —O—, —S—, —CO—, —O—CO—, —CO—O—, —O—CO—O—, —O—CO—O—, —S—CO—, —CO—S—, —O—CO—S—, —S—CO—O—, —CO—NH—, —NH—CO—, —NH—CO—O—, —NR'—, >P═O, —S—S—, and —SO$_2$—;

R' represents a hydrogen atom or a C1-C8 alkyl group;

a plurality of $R^{402}$'s may be taken together to form a benzene ring or a naphthalene ring;

a plurality of $R^{402}$'s may be the same or different; a plurality of $R^{404}$'s may be the same or different;

n represents a number of 4 to 6;

$X^4$ represents a substituent represented by formula (9) when n is 4, $X^4$ represents a substituent represented by formula (10) when n is 5, or $X^4$ represents a substituent represented by formula (11) when n is 6;

$X^4$ may optionally be taken together with A to form a ring; and the aromatic or heterocyclic ring may be fused to one or more additional rings;

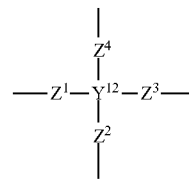
(9)

wherein $Y^{12}$ represents a carbon atom, a tetravalent C1-C35 aliphatic hydrocarbon group, a tetravalent C6-C35 aromatic ring-containing hydrocarbon group, or a tetravalent C2-C35 heterocyclic ring-containing group, the aliphatic hydrocarbon group being optionally substituted by a combination of one or more groups selected from —COO—, —O—, —OCO—, —NHCO—, —NH—, and —CONH—; and $Z^1$, $Z^2$, $Z^3$, and $Z^4$ each independently represents a single bond, —O—, —S—, >CO, —CO—O—, —O—CO—, —SO$_2$—, —SS—, —SO—, >NR$^{32}$, >PR$^{32}$, an optionally substituted C1-C35 aliphatic hydrocarbon group, an optionally substituted C6-C35 aromatic ring-containing hydrocarbon group, or an optionally substituted C2-C35 heterocyclic ring-containing group;

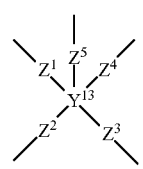
(10)

wherein $Y^{13}$ represents a pentavalent C2-C35 aliphatic hydrocarbon group, a pentavalent C6-C30 aromatic ring-containing hydrocarbon group, or a pentavalent C2-C30 heterocyclic ring-containing group, the aliphatic hydrocarbon group being optionally substituted by a combination of one or more groups selected from —COO—, —O—, —OCO—, —NHCO—, —NH—, and —CONH—; and $Z^1$, $Z^2$, $Z^3$, $Z^4$, and $Z^5$ each independently represents a single bond, —O—, —S—, >CO, —CO—O—, —O—CO—, —SO$_2$—, —SS—, —SO—, >NR$^{32}$, >PR$^{32}$, an optionally substituted C1-C35 aliphatic hydrocarbon group, an optionally substituted C6-C35 aromatic ring-containing hydrocarbon group, or an optionally substituted C2-C35 heterocyclic ring-containing group;

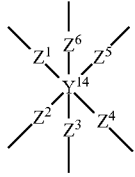
(11)

wherein $Y^{14}$ represents a hexavalent C2-C35 aliphatic hydrocarbon group, a hexavalent C6-C35 aromatic ring-containing hydrocarbon group, or a hexavalent C2-C35 heterocyclic ring-containing group, the aliphatic hydrocarbon group being optionally substituted by a combination of one or more groups selected from —COO—, —O—, —OCO—, —NHCO—, —NH—, and —CONH—; and $Z^1$, $Z^2$, $Z^3$, $Z^4$, $Z^5$, and $Z^6$ each independently represents a single bond, —O—, —S—, >CO, —CO—O—, —O—CO—, —SO$_2$—, —SS—, —SO—, >NR$^{32}$, >PR$^{32}$, an optionally substituted C1-C35 aliphatic hydrocarbon group, an optionally substituted C6-C35 aromatic ring-containing hydrocarbon group, or an optionally substituted C2-C35 heterocyclic ring-containing group.

5. A composition comprising the compound according to claim 2, a radical polymerizable organic substance, and a photo-radical polymerization initiator or a thermal radical polymerization initiator.

6. A composition comprising the compound according to claim 3, a radical polymerizable organic substance, and a photo-radical polymerization initiator or a thermal radical polymerization initiator.

7. A composition comprising the compound according to claim 4, a radical polymerizable organic substance, and a photo-radical polymerization initiator or a thermal radical polymerization initiator.

* * * * *